(12) United States Patent
McGuigan et al.

(10) Patent No.: US 8,933,053 B2
(45) Date of Patent: Jan. 13, 2015

(54) PHOSPHORAMIDATE DERIVATIVES OF 5-FLUORO-2'-DEOXYURIDINE FOR USE IN THE TREATMENT OF CANCER

(75) Inventors: Christopher McGuigan, Cardiff (GB); Jan Balzarini, Heverlee (BE); Magdalena Slusarczyk, Cardiff (GB); Blanka Gonczy, Cardiff (GB); Paola Murziani, Cardiff (GB)

(73) Assignee: NuCana BioMed Limited, Camberley (GB)

( * ) Notice: Subject to any disclaimer, the term of this patent is extended or adjusted under 35 U.S.C. 154(b) by 0 days.

(21) Appl. No.: 14/000,682

(22) PCT Filed: Feb. 29, 2012

(86) PCT No.: PCT/GB2012/050457
§ 371 (c)(1),
(2), (4) Date: Nov. 14, 2013

(87) PCT Pub. No.: WO2012/117246
PCT Pub. Date: Sep. 7, 2012

(65) Prior Publication Data
US 2014/0057866 A1     Feb. 27, 2014

(30) Foreign Application Priority Data

Mar. 1, 2011  (GB) .................................. 1103582.1
Apr. 1, 2011  (GB) .................................. 1105660.3

(51) Int. Cl.
| A61K 31/7072 | (2006.01) |
| A61K 45/06 | (2006.01) |
| C07H 19/10 | (2006.01) |
| C07F 9/6584 | (2006.01) |
| C07F 9/655 | (2006.01) |
| C07F 9/6558 | (2006.01) |

(52) U.S. Cl.
CPC ............. *A61K 31/7072* (2013.01); *A61K 45/06* (2013.01); *C07F 9/65844* (2013.01); *C07H 19/10* (2013.01); *C07F 9/65515* (2013.01); *C07F 9/65586* (2013.01)
USPC ............................................. 514/51; 536/26.8

(58) Field of Classification Search
USPC ........................................... 514/51; 536/26.8
See application file for complete search history.

(56) References Cited

U.S. PATENT DOCUMENTS

2003/0109697 A1   6/2003   Shepard
2013/0252918 A1   9/2013   McGuigan

FOREIGN PATENT DOCUMENTS

| DE | 279248 | 8/1996 |
| GB | 1 377 027 | 12/1974 |
| WO | WO99/37753 | 7/1999 |
| WO | WO0107454 | 2/2001 |
| WO | WO03000713 | 1/2003 |
| WO | WO2005/012327 | 2/2005 |
| WO | WO2005012327 | 2/2005 |
| WO | WO2007056596 | 7/2007 |
| WO | WO2008121634 | 10/2008 |
| WO | WO2012/048013 | 4/2012 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
International Search Report; PCT/GB2012/050457; Apr. 19, 2012; M. Ebhard; 3 pp.
McGuigan et al.; Phosphoramidate ProTides of the Anticancer Agent FUDR Successfully Deliver the Preformed Bioactive Monophosphate in Cells and Confer Advantage over the Parent Nucleoside; *Journal of Medicinal Chemistry*; vol. 54, No. 2; Oct. 27, 2011; pp. 7247-7258.
Vande Voorde et al.; The Cytostatic Activity of NUC-3073, a Phosphoramidate Prodrug of 5-fluoro-2'-deoxyuridine, is Independent of Actifation by Thymidine Kinase and Insensitive to Degradation by Phosphorolytic Enzymes; *Biochemical Pharmacology*; vol. 82, No. 5; Sep. 1, 2011; pp. 441-452.
UK Search Report, GB1103582.1, dated Jun. 15, 2011.
Agarwal R.P., Han T., Fernandez M., Collateral resistance of a dideoxycytidineresistant cell line to 5-fluoro-2'-deoxyuridine. Biochem. Biophys. Res. Commun. 1999; 262:657-60.

(Continued)

*Primary Examiner* — Kristin Vajda
(74) *Attorney, Agent, or Firm* — Fish & Richardson P.C.

(57) ABSTRACT

Phosphoramidate derivatives of 5-fluoro-2'-deoxyuridine are disclosed for use in the treatment of cancer, especially in the treatment of cancer where the patient shows resistance, for example, in a patient with cells with a lowered level of nucleoside transporter proteins and/or with nucleoside kinase-deficient cells and/or with mycoplasma-infected cells and/or with cells with a raised level of thymidylate synthase.

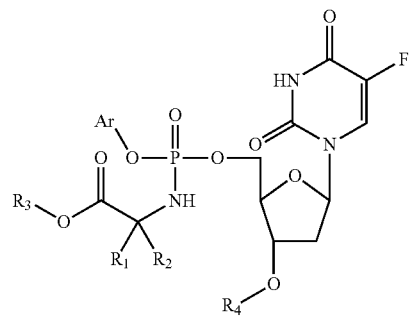

32 Claims, 14 Drawing Sheets

(56) References Cited

OTHER PUBLICATIONS

Ayusawa D., Koyama H., Iwata K., Seno T., Single-step selection of mouse FM3A cell mutants defective in thymidylate synthetase. Somatic Cell Genet. 1980; 6:261-70.

Ayusawa D., Koyama H., Seno T., Resistance to methotrexate in thymidylate synthetase-deficient mutants of cultured mouse mammary tumor FM3A cells. Cancer Res. 1981; 41:1497-501.

Balzarini J., De Clercq E., Torrence P.F., Mertes M.P., Park J.S., Schmidt CL., Shugar D., Barr P.J., Jones A.S., Verhelst G., Walker RT., Role of thymidine kinase in the inhibitory activity of 5-substituted-2'-deoxyuridines on the growth of human and murine tumor cell lines. Biochem Pharmacol. 1982:31:1089-1095.

Balzarini J. and De Clercq E., Strategies for the measurement of the inhibitory effects of thymidine analogs on the activity of thymidylate synthase in intact murine leukemia L1210 cells. Biochem. Biophys Acta 1984; 785:36-45.

Beck A., Etienne M.C., Cheradame S., Fischel J.L., Formento P., Renee N., Milano G., A role for dihydropyrimidine dehydrogenase and thymidylate synthase in tumour sensitivity to fluorouracil. Eur J Cancer 1994; 30A:1517-22.

Bronckaers A., Balzarini I., Liekens S., The cytostatic activity of pyrimidine nucleosides is strongly modulated by Mycoplasma hyorhinis infection: Implications for cancer therapy. Biochem Pharmacol 2008; 76:188-97.

Bronckaers A., Gago F., Balzarini J., Liekens S., The dual role of thymidine phosphorylase in cancer development and chemotherapy. Med Res Rev 2009; 29:903-53.

Chan P.J., Seraj I.M., Kalugdan TH., King A., Prevalence of mycoplasma conserved DNA in malignant ovarian cancer detected using sensitive PCR-ELISA Gynecol Oncol 1996;63:258-60.

Charron J. and Langelier Y, Analysis of deoxycytidine (dC) deaminase activity in herpes simplex virus-infected or HSV TK-transformed cells: association with mycoplasma contamination but not with virus infection. J Gen Virol 1981; 57:245-50.

Ciaparrone M., Quirino M., Schinzari G., Zannoni G., Corsi D.C., Vecchio FM., Cassano A., La Tone G., Barone C. Predictive role of thymidylate synthase, dihydropyrimidine dehydrogenase and thymidine phosphorylase expression in colorectal cancer patients receiving adjuvant 5-fluorouracil. Oncology 2006; 70:366-77.

Ciccolini J., Evrard A., Cuq P. Thymidine phosphorylase and fluoropyrimidines efficacy: a Jekyll and Hyde story. Curr Med Chem Anticancer Agents 2004; 4:71-81.

Congiata C., Brancale A., Mason M.D., Jiang W.G., McGuigan C., Novel potential anticancer naphthyl phosphoramidates of BVdU: separation of diastereoisomers and assignment of the absolute configuration of the phosphorus center. J. Med. Chem. 2006; 49:452-5.

de Bruin M., van Capel T., Smid K., van der Born K., Fukushima M., Hoekman K., Pinedo H.M,., Peters GI., Role of platelet derived endothelial cell growth factor thymidine phosphorylase in fluoropyrimidine sensitivity and potential role of deoxyribose-1-phosphate. Nucleosides Nucleotides Nucleic Acids 2004; 23:1485-90.

Galmarini C,M., Mackey I.R., Dumontet C., Nucleoside analogues and nucleobases in cancer treatment. Lancet Oncol 2002; 3:415-24.

Harris S.A., McGuigan C., Andrei G., Snoeck R., De CE., Balzarini J., Synthesis and antiviral evaluation of phosphoramidate derivatives of (E)-5-(2-bromovinyl)-2'deoxyuridine. Antivir Chem Chemother 2001; 12:293-300.

Hatse S., De C.E., Balzarini J., Role of antimetabolites of purine and pyrimidine nucleotide metabolism in tumor cell differentiation. Biochem Pharmacol 1999; 58:539-55.

Hecker S.J. and Erion M.D., Prodrugs of phosphates and phosphonates. J. Med. Chem. 2008; 51:2328-45.

Huang S., Li J.Y., Wu I., Meng L., Shou CC., Mycoplasma infections and different human carcinomas. World J Gastroenterol 2001; 7:266-9.

Ishikawa T., Utoh M., Sawada N., Nishida M., Fukase Y, Sekiguchi F., Ishitsuka H., Tumor selective delivery of 5-fluorouracil by capecitabine, a new oral fluoropyrimidine carbamate, in human cancer xenografts. Biochem Pharmacol 1998; 55:1091-7.

Jette L., Bissoon-Haqqani S., Le FB., Maroun JA., Birnboim H.C., Resistance of colorectal cancer cells to 5-FUdR and 5-FU caused by Mycoplasma infection. Anticancer Res 2008; 28:2175-80.

Kamoshida S., Shiogama K. Shimomura R. Inada K. Sakurai Y, Ochiai M., Matuoka H., Maeda K. Tsutsumi Y., Immunohistochemical demonstration of fluoropyrimidine-metabolizing enzymes in various types of cancer. Oncol Rep. 2005.14:1223-30.

Kidder M., Chan P.I., Seraj I,M., Patton W,C., King A Assessment of archived paraffinembedded cervical condyloma tissues for mycoplasma-conserved DNA using sensitive PCR-ELISA Gynecol Oncol 1998; 71:254-257.

Kinsella A.R and Smith D., Tumor resistance to anti metabolites. Gen Pharmacol 1998; 30:623-6.

Koopman M., Venderbosch S., Nagtegaal ID., van Krieken J.H., Punt C.J. A review on the use of molecular markers of cytotoxic therapy for colorectal cancer, what have we learned? Eur J Cancer 2009; 45: 1935-49.

Kosaka T., Usami K. Ueshige N., Sugaya J. Nakano Y, Takashima S. Effects of thymidine phosphorylase levels in cancer, background mucosa, and regional lymph nodes on survival of advanced gastric cancer patients receiving postoperative fluoropyrimidine therapy. Oncol Rep 2004; 12:1279-86.

Lackey et al., Enzyme-catalyzed therapeutic agent (ECTA) design: activation of the antitumor ECTA compound NB1011 by thymidylate synthase, Biochemical Pharmacology 61 (2001) pp. 179-189.

Liekens S., Bronckaers A., Balzarini J., Improvement of purine and pyrimidine antimetabolite-based anticancer treatment by selective suppression of mycoplasma-encoded catabolic enzymes. Lancet Oncol. 2009; 10:628-35.

Longley D.B., Harkin D.P., Johnston P.G., 5-fluorouracil: mechanisms of action and clinical strategies. Nat Rev Cancer 2003; 3:330-8.

McGuigan, C.; Pathiran'a, R. N.; Balzarini, J.; De Clercq, E. Intracellular delivery of bioactive AZT nucleotides by aryl phosphate derivatives of AZT. Med. Chem. 1993, 36, 1048.

McGuigan, C.; Cahard, D.; Hendrika, D.; Sheeka, M.; De Clercq, E.; Balzarini, J. Aryl phosphora' midate derivatives of d4T have improved anti-HIV efficacy in tissue vulture and may act by the generation of a novel intracellular metabolite. J. Med. Chem. 1996, 39, 1748.

McGuigan, C.; Tsang, H. W.,; Cahardr, D. Turner, K.; Velazquez, S.; Salgado, A; Bidois, L.; Naesens, L.; De Clercq, E.; Balzarini, J. Phosphoramidate derivatives of d4T as inhibitors of HIV: The effect of amino acid variation. Antiviral Res. 1997, 35, 195.

McGuigan, Christopher, Thiery, Jean-Christophe, Daverio, Felice. Davies, Gaynor, Mason, Malcolm, Anti-cancer ProTides: tuning the activity of BVDU phosphoramidates related to thymectacin, Bioorganic & Medicinal Chemistry, 2005, vol. 13(9) pp. 3219-3227.

McGuigan C, Gilles A, Madela K, Aljarah M, Holl S, Jones S, Vernachio J, Hutchins J, Ames B, Bryant KD, Gorovits E, Ganguly B, Hunley D, Hall A, Kolykhalov A, Liu Y, Muhammad J, Raja N, Walters R, Wang J, Chamberlain S, Henson G, Phosphoramidate ProTides of 2'-C-methylguanosine as highly potent inhibitors of hepatitis C virus. Study of their in vitro and in vivo properties. J Med Chem 2010;53:4949-57.

Mehellou, J.; Balzarini, J.; McGuigan, C.; Aryloxy phosphoramidate triesters: a technology for delivering mono-phosphorylated nucleosides and sugars into cells. Chem. Med. Chem., 2009, 4, 11, 1779.

Mehellou, Y.,; Valente, R.; Mottram, H.; Walsby, E.; Mills, K. I.; Balzarini, J.; Mcgugan, C. Phosphoramidates of 2'-B-d-arabinouridine (AraU) as phosphate prodrugs: design, synthesis, in vitro activity and metabolism. Bioorg. Med. Chern. 2010, 18, 2439.

Moertel C.G., Chemotherapy for colorectal cancer. N Engl J Med 1994; 330:1136-42.

Murakami Y, Kazuno H., Emura T., Tsujimoto H., Suzuki N., Fukushima M., Different mechanisms of acquired resistance to fluorinated pyrimidines in human colorectal cancer cells. Int J Oncol, 2000; 17:277-83.

(56) References Cited

OTHER PUBLICATIONS

Neale G.A., Mitchell A., Finch L.R., Enzymes of pyrimidine deoxyribonucleotide metabolism in *Mycoplasma mycoides* subsp. *mycoides*. J Bacteriol 1983; 156:1001-5.
Pehlivan M., Pehlivan S., Onay H., Koyuncuoglu M., Kirkali Z, Can mycoplasmamediated oncogenesis be responsible for formation of conventional renal cell carcinoma? Urology 2005; 65:411-414.
Peters G.J. and Kohne C.H., Resistance to anti metabolites. In: Fluoropyrimidines as Antifolate Drugs in Cancer Therapy. Jackman AL (ed). Humana Press Inc. 20 1999; pp. 101-145.
Razin S., The mycoplasmas. Microbiol Rev 1978; 42:414-70.
Razin S., Yogev D., Naot Y, Molecular biology and pathogenicity of mycoplasmas. Microbiol Mol Biol. Rev 1998; 62:1094-156.
Sasaki H., Igaki H., Ishizuka T., Kogoma Y, Sugimura T., Terada M., Presence of *Streptococcus* DNA sequence in surgical specimens of gastric cancer. Jpn J Cancer Res 1995; 86:791-4.
Seno T., Ayusawa D., Shimizu K., Koyama H., Takeishi K., Hori T., Thymineless death and genetic events in mammalian cells. Basic Life Sci 1985; 31:241-63.
Sinigaglia F. and Talmadge K.W., Inhibition of [3H]thymidine incorporation by *Mycoplasma arginini*-infected cells due to enzymatic cleavage of the nucleoside. Eur J Immunol 985; 15:692-6, 1985.
Sotos G.A., Grogan L., Allegra C.J., Preclinical and clinical aspects of biomodulation of 5-fluorouracil. Cancer Treat Rev 1994; 20:11-49.
Tanaka F., Fukuse T., Wada H., Fukushima M., The history, mechanism and clinical use of oral 5-fluorouracil derivative chemotherapeutic agents. Curr Pharm Biotechnol. 2000; 1:137-64.
Tham T.N., Ferris S., Kovacic R., Montagnier L., Blanchard A., Identification of *Mycoplasma pirum* genes involved in the salvage pathways for nucleosides. J Bacteriol. 1993; 175:5281-5.
Walko C.M. and Lindley C., Capecitabine: a review. Clin Ther 2005; 27:23-44.
Yang H., Qu L., Ma H., Chen L., Liu W, Liu C., Meng L., Wu J., Shou C., *Mycoplasma hyorhinis* infection in gastric carcinoma and its effects on the malignant phenotypes of gastric cancer cells. BM.C. Gastroenterol. 2010;10:132.
Balzarini, J. et al, Proc. Natl. Acad. Sci. U.S.A. 1996, 93, pp. 7295-7299.
Birkus, G. et al, Antimicrob. Agents Chemother. 2004, 51, pp. 543-550.
Cahard, D. et al, Mini-Rev. Med. Chem. 2004, 4, pp. 371-382.
Cahard, D. et al, "Aryloxy Phosphoramidate Triesters as Pro-Tides," Mini-Reviews in Medicinal Chemistry, 2004, 4, pp. 371-382.
CAS Abstract accession No. 1995:297145 of Antiviral Chemistry & Chemotherapy, 1995, vol. 6(1), Nillroth et al., pp. 50-64.
CAS Abstract accession No. 1997:432895 of Drug Design and Discovery 1995 vol. 13 (1) Nillroth et al pp. 43-54.
Congiatu, C. et al, Nucleosides, Nucleotides and Nucleic Acids (2005) 24:5-7, 485-489.
Dang, Q. et al, J. Am. Chem. Soc. 2007,129, pp. 15494-15502.
Derudas, M. et al, J. Med. Chem. 2009, 52, pp. 5520-5530.
English Abstract for DD279248 published Aug. 20, 1996, WPI Accession No. 1990-327965 [199044].
Ensminger, W. D. et al, Semin. Oncol. 1983, 10, pp. 176-182.
Grem, J. L., Invest. New Drugs 2000, 18, pp. 299-313.
Heidelberger, C. et al, Nature 1957,179, pp. 663-666.
Holland, J. F.; Frei, E.; Pizzorno, G.; Diasio, R. B.; Cheng, Y. C.: "*Cancer Medicine*" 7th Ed. BC Decker: Hamilton, Ontario, Canada, 2006.
Homsi, J. et al, Cancer Control 2006, 13, pp. 42-47.
International Search Report and Written Opinion in International Application No. PCT/GB2012/050457, dated Apr. 19, 2013, 14 pp.
International Preliminary Report on Patentability in International Application No. PCT/GB2012/050457, dated Sep. 9, 2013, 7 pp.
International Search Report issued in PCT/GB2011/001446 on Jan. 26, 2012.
Jones, B. C. et al, "Synthesis and anti-HIV activity of some novel phosphorodiamidate derivatives of 3'-asido-3'-deoxythymidine (AZT)," Antiviral Chemistry & Chemotherapy (1991) 2(1) pp. 35-39.
Lee, W. A. et al, Antimicrob Agents Chemother. 2005, 49, pp. 1898-1906.
Malet-Martino, M. et al, Oncologist, 2002, 7, pp. 288-323.
McGuigan, C. et al, Bioorg. Med. Chem. 2005, 13, pp. 3219-3227.
McGuigan, C. et ai, Bioorg. Med. Chem. Lett. 2010, 20 pp. 4850-4854.
McGuigan, C. et al, J. Med. Chem. 2005, 48, pp. 3504-3515.
Nillroth et al, "Specific interaction between HIV-1 proteinase and 5'-phosphate peptidomimetic derivatives of nucleoside analogs," Drug Design and Discovery 1995 vol. 13(1), pp. 43-54.
Nillroth et al, "The use of 5'-phosphate derivatives of nucleoside analogues as inhibitors of HIV-1 replication," Antiviral Chemistry & Chemotherapy 1995 vol. 6(1), pp. 50-64.
Parker, W. B., Chem. Rev. 2009, 109, pp. 2880-2893.
Pegram, M. et al, Eur. J. Cancer 2002, 38 (Suppl. 7) S34.
Pehlivan, M. et al, Lung Cancer 2004, 45, pp. 129-130.
Saboulard, D. et al, Mol. Pharmacol. 1999, 56, pp. 693-704.
Sobrero, A. F. etal, Cancer Res. 1985, 45, pp. 3155-3160.
UK Search Report issued in GB1016855.7 on Jan. 26, 2011.
Vail, D. M. et al, 2007 MCR Annual Meeting Los Angeles CA, "Efficacy and safety profile of GS-9219, a novel guanine nucleotide analog prodrug, for the treatment of lymphoid malignancies using pet dogs with spontaneous non-Hodgkin's lymphoma as a model," Apr. 18, 2007.
Wagner, C. R. et al, "Pronucleotides: Toward the In Vivo Delivery of Antiviral and Anticancer Nucleotides," Med. Res. Rev. 2000, 20, pp. 417-451.
Walsby, E. et al, Blood, 2005, 106(11), pp. 941A-942A and Abstract 3369.
Written Opinion in International Application No. PCT/GB2012/050457, dated Sep. 1, 2013, 6 pp.
Yagil, E. et al, J. Bacteriol. 1971, 108 (2), pp. 760-764.
Zhang, Z G, Semin. Oncol. 1992, 19 (2 Suppl. 3) pp. 4-9.

\* cited by examiner

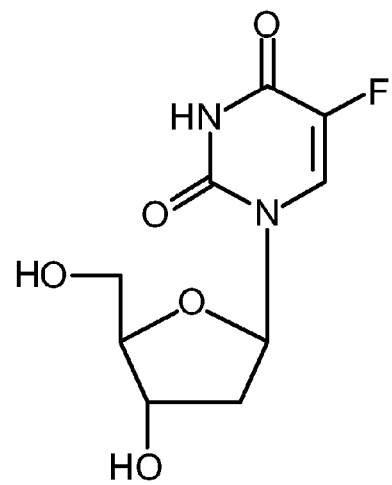
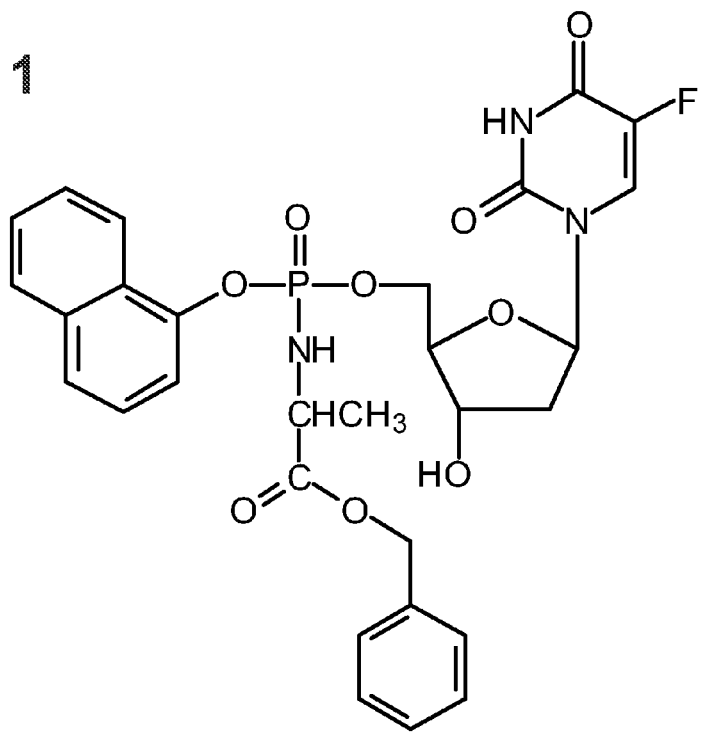
FIG. 1

*E. coli* TP

Human TP

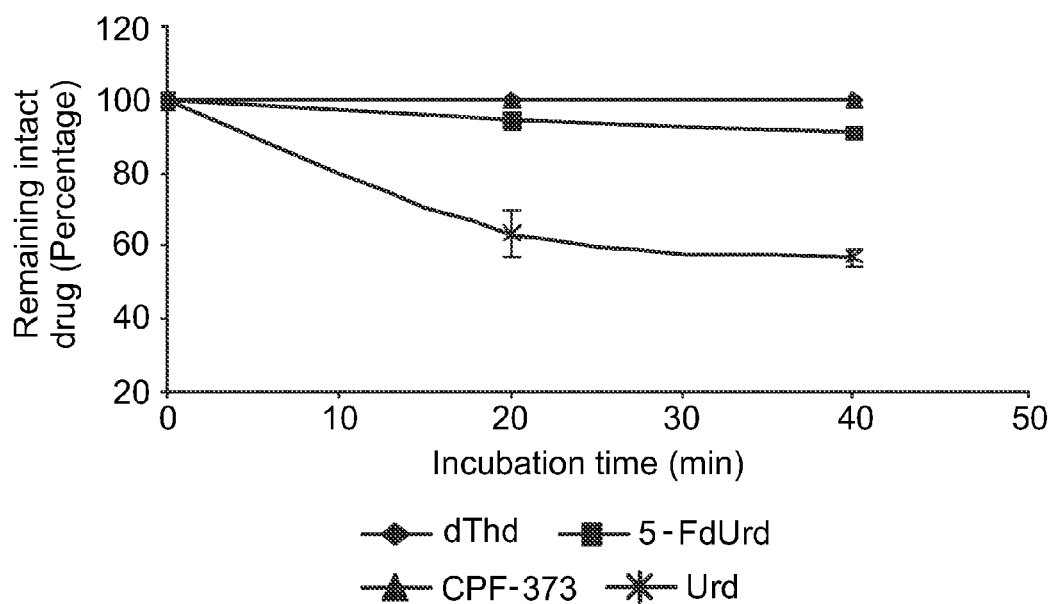

Inhibition of TS in L1210/0 cells by 5-FdUrd
(substrate: [5-³H]dUrd)

Inhibition of TS in L1210/0 cells by CPF-373
(substrate: [5-³H]dUrd)

Inhibition of TS in L1210/0 cells by 5-FdUrd
(substrate: [5-$^3$H]dCyd)

Inhibition of TS in L1210/0 cells by CPF-373
(substrate: [5-$^3$H]dCyd)

Inhibition of TS in L1210/TK cells by 5-FdUrd
(substrate: [5-$^3$H]dCyd)

Inhibition of TS in L1210/TK cells by CPF-373
(substrate: [5-$^3$H]dCyd)

a: esterase or carboxypeptidase-type enzyme  b: spontaneous
c: spontaneous   d: phosphoramidase-type enzyme

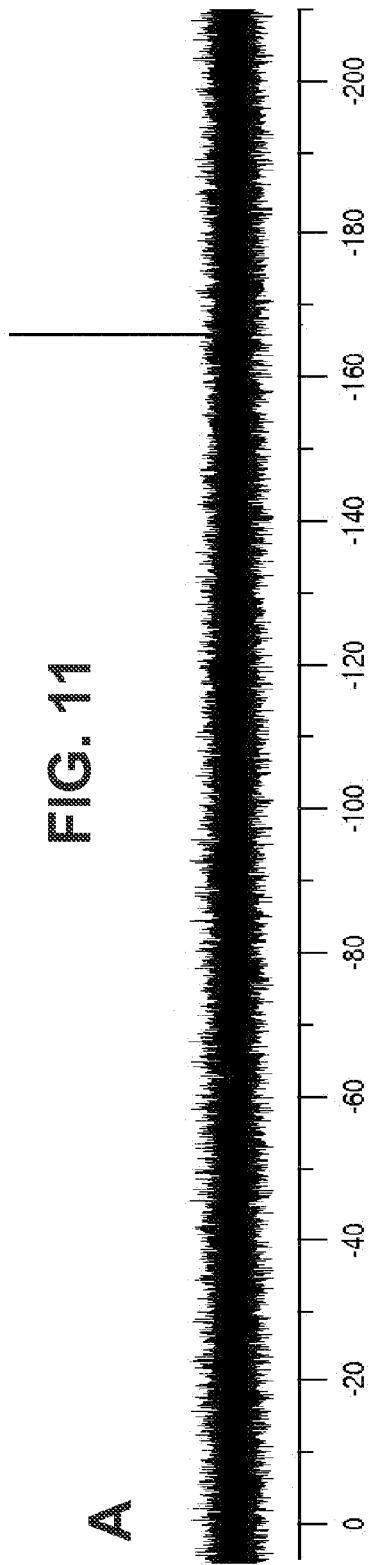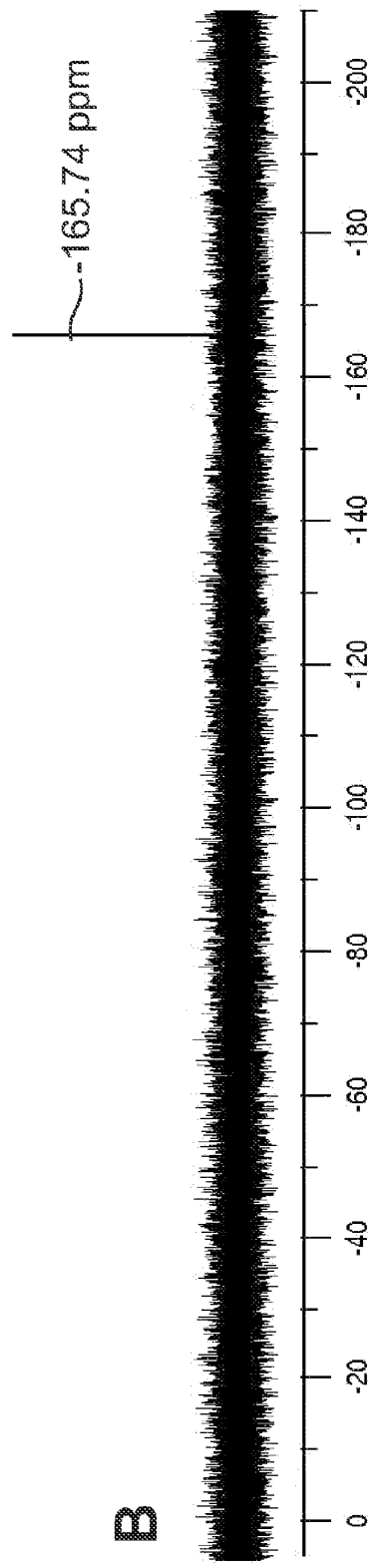
FIG. 11

PHOSPHORAMIDATE DERIVATIVES OF 5-FLUORO-2'-DEOXYURIDINE FOR USE IN THE TREATMENT OF CANCER

CROSS-REFERENCE TO RELATED APPLICATIONS

This application is a 35 USC 371 national stage application of International App. No. PCT/GB2012/050457, filed Feb. 29, 2012, which claims priority to GB 1103582.1, filed Mar. 1, 2011, and GB 1105660.3, filed Apr. 1, 2011.

The present invention relates to chemical compounds useful in the treatment of cancer.

In 1957, the antitumour activity of 5-Fluorouracil (5FU) was discovered. More than fifty years since it was first synthesised, 5FU remains widely used in the treatment of solid tumours including breast, gastrointestinal system, head, neck and ovary and in particular of colorectal cancer, as approved by FDA in 1962. The fluoropyrimidine 5-fluorouracil (5FU) and 5-fluoro-2'-deoxyuridine (5-FdUrd) are used in combination with folic acid as standard treatment for a variety of carcinomas, as stomach, colon and breast. Moreover, a combination of 5FU with leucovorin (LV) is considered as standard chemotherapy for colon cancer. The drug 5FU is usually administered by intravenous bolus or by continuous infusion.

The antitumour activity of 5FU is comparable to that of its analogue 5-FdUrd, which partly acts as prodrug of 5FU. 5-FdUrd was approved by FDA in 1970, and has been used extensively for the clinical treatment of carcinoma of the ovary, breast and gastrointestinal tract. Moreover due to extensive hepatic extraction 5-FdUrd is a useful drug for hepatic arterial chemotherapy of liver metastases thereby it is more efficiently metabolized by the liver than 5FU.

A problem exists, however, in that activity of both the agents 5FU and 5-FdUrd can be impaired by the development of resistance in tumour cells. Treatment of cancer with 5FU has also been found to cause neurotoxic and cardiotoxic side effects. Toxicity also derives from the lack of selectivity of 5FU towards tumours.

It is an object of the present invention to provide compounds derived from 5-fluoro-2'-deoxyuridine that show an enhanced activity and/or reduced toxicity in their treatment of cancer, compared to that shown by 5-fluoracil or 5-fluoro-2'-deoxyuridune per se.

It is a further object of the present invention to provide compounds derived from 5-fluoro-2'-deoxyuridine that show a low level of resistance in tumour cells, in particular a resistance in tumour cells that is less than that shown by 5FU or by 5-FdUrd.

According to the present invention there is provided a compound of formula (I):

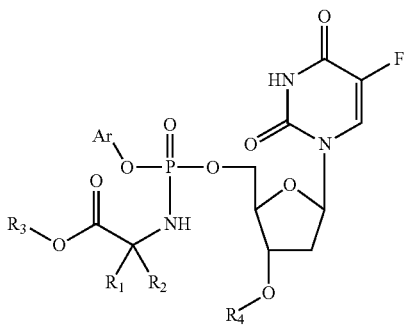

wherein

Ar is a fused bicyclic aryl moiety or a monocyclic aryl moiety, either of which aryl moieties is carbocyclic or heterocyclic and is optionally substituted;

$R_3$ is alkyl, which is optionally substituted;

$R_4$ is H or alkoyl; and $R_1$ and $R_2$ are independently selected from the group consisting of H and alkyl or $R_1$ and $R_2$ together form an alkylene chain so as to provide, together with the C atom to which they are attached, a cyclic system, or one of $R_1$ and $R_2$ comprises an alkylene chain attached to N, the H atom attached to N is absent and one of $R_1$ and $R_2$ comprises H or alkyl, any of which alkyl moieties or alkylene chains may be substituted; or a pharmaceutically acceptable derivative or metabolite of formula I, wherein the compound is not a compound having, in combination, Ar as unsubstituted phenyl, $R_3$ as $CH_3$, $R_4$ as H and one of $R_1$ and $R_2$ as H and one of $R_1$ and $R_2$ as $CH_3$.

It has been found that the compounds of the present invention show activity that renders them useful in the prophylaxis or treatment of cancer in *homo sapiens*. In particular, the present compounds exhibit beneficial properties which indicate their ability to treat cancer in patients whilst showing reduced resistance in tumour cells. Notably, compounds of the present invention can show a cytoactivity comparable to or better than that of 5-fluoracil, but with a resistance that is comparable to or less than that of each of 5-fluoracil and 5-fluoro-2'-deoxyuridine.

By "resistance" in the present application is meant a low or diminished response to therapy. Resistance can be innate or acquired. An innate resistance is a reduced responsiveness relative to other specimens or patients. An acquired resistance is a reduced effectiveness over the course of time in a given patient, whether or not acquired in conjunction with therapy comprising the administration to the patient of a drug regime to treat cancer, for example, a drug regime comprising 5FU and/or 5-FdUrd. Each of innate resistance and acquired resistance can correspond to the downregulation or low activity of transporter proteins, including nucleoside transporter proteins, or necessary anabolic enzymes or the upregulation of catabolic enzymes.

Although the applicant does not wish to be bound by any theory, it is postulated, as discussed further below, that causes of resistance in tumour cells to the activity of 5FU and/or 5-FdUrd could be: a) deletion of activating kinase as thymidine kinase (TK), a key enzyme required for the initial phosphorylation step from 5-FdUrd to 5-FdUMP; b) overproduction of thymidylate synthase (TS); and/or c) deficient transport into target cells.

Surprisingly it has now been found that compounds of the present invention can show significant cytostatic activity in cells with a lowered level of nucleoside transporter proteins and/or with nucleoside kinase-deficient cells and/or in mycoplasma-infected cells.

The beneficial property of compounds of the present invention to retain marked cytostatic activity in nucleoside kinase-deficient cells may confer in vivo a clinical advantage in cellular environments lacking in nucleoside kinases or having decreased levels of nucleoside kinases and thus unable to efficiently activate 5-FdUrd.

*Mycoplasma*-infected cells greatly reduce the activity of nucleosides such as 5-FdUrd due, it is believed, to the overproduction of thymidylate synthase (TS). The presently proposed use of the present compounds in mycoplasma-infected cells thus, it is postulated, derives from the beneficial property of the present compounds to act additionally as a TS inhibitor and so permit the present compounds to retain their cytostatic activity in mycoplasma-infected cells. The prodrugs comprising the compounds of the present invention, due to their lipophylic nature may be taken up by the target cells in an at least partially nucleoside transport carrier-independent way, and thus, may circumvent potential resistance mechanisms due to lowered levels of nucleoside or nucleobases transport carriers in the target cell membrane.

Additionally, the prodrugs comprising the compounds of the present invention are surprisingly insensitive to the action of the catabolic enzyme Thymidine Phosphorylase (TP) that is often upregulated in tumours, and thus, the prodrugs would be more independent of the presence of this catabolic enzyme than 5-FdUrd.

It has been observed that mycoplasma infection of cells can greatly reduce the activity of nucleosides, including 5-FdUrd. Administration of a TP inhibitor restores the cytostatic activity of 5-FdUrd in mycoplasma-infected cell cultures, providing evidence of the deteriorating role of TP in the eventual cytostatic activity of 5-FdUrd. This may be a limitation in patients that are mycoplasma infected. Unlike 5-FdUrd, the 5-FdUrd prodrugs of the present invention can retain high activity in these mycoplasma-infected cells.

The present compounds thus have the potential to overcome many of the limitations of 5-FU and 5-FdUrd.

5-Fluorouracil (5FU) is one of the first examples of an anticancer drug. The design of 5-FU was based on the available biochemical information: a fluorine atom and a hydrogen atom have a similar size, however a carbon-fluorine bond is much stronger than a carbon-hydrogen bond. Thymidylate synthase acts by replacing the 5-hydrogen of deoxyuridine monophosphate with a methyl group obtained from methylene tetrahydrofolate to make thymidylate. 5FU exerts its cytotoxic effect through three different pathways. The nucleobase 5FU and the deoxyribonucleoside 5-FdUrd enter cells through facilitated nucleoside transport systems. One of the mechanisms of action of these agents is inhibition of the enzyme thymidylate synthase (TS). The nucleobase 5FU is converted to the deoxynucleoside 5-fluoro-2'-deoxyuridine (5-FdUrd) by thymidine phosphorylase. Subsequent phosphorylation of the deoxynucleoside 5-FdURd by thymidine kinase results in formation of the cytotoxic nucleotide 5-fluoro-2'-deoxyuridine-5'-monophosphate (5-FdUMP). In the presence of the reduced folate, 5,10-methylene-tetrahydrofolate (mTHF), the nucleotide (5-FdUMP) inhibits thymidylate synthase (TS) due to the inability of the enzyme to remove the 5-fluorine atom. Thus, the first and the foremost important mechanism of action of 5FU and FDUR is inhibition of the enzyme thymidylate synthase (TS). Thymidylate synthase (TS) has two substrates for (dUMP and mTHF), both of which bind in the catalytic site to enable the synthesis of dTMP. 5-FdUMP forms a covalent ternary complex with thymidylate synthase (TS), inhibiting this enzyme activity and leading to depletion of deoxythymidine triphosphate, necessary for DNA synthesis. Alternatively, (5-FdUMP) is synthesized after conversion of 5FU to 5-FUMP by OPRT, to fluorouridine diphosphate (FUDP), fluorodeoxyuridine diphosphate (5-FdUDP) by ribonucleotide reductase (RR) and eventually to 5'-FdUMP. It has been observed that after drug exposure to 5FU or 5-FdUrd, the cells develop resistance to these chemotherapeutic agents. The overexpression of thymidylate synthase (TS) reduces the therapeutic effect of TS inhibitory drug leading to resistance. It was observed that some individuals are more resistant to TS targeted therapy than others. Secondly, the deoxynucleoside 5-fluoro-2'-deoxyuridine (5-FdUrd) can be converted to its triphosphate 5-FdUTP form which in turn can be incorporated into DNA causing cell damage. Thirdly, 5FU may also inhibit RNA synthesis by its conversion to FUMP by OPRT and subsequently, in two steps, to fluorouridine triphosphate (FUTP) that is incorporated into RNA. This is believed to be another potential action of 5FU.

The molecule 5FU thus does not result in an optimal TS inhibitory drug because it is inefficiently converted to 5-FdUMP due to the several metabolic steps required for metabolic activation of 5FU. Further resistance can occur if the cell produces excess quantities of dUMP to compete with the drug for the active site.

5-FdUrd is a relatively good substrate for thymidine kinase, which converts it directly to 5-FdUrd . in vitro, studies, in several cancer cell lines have demonstrated that 5-FdUrd is about 5000 fold more potent as inhibitor of cell growth than 5FU. Furthermore, the prodrug 5-FdUrd shows no significant conversion to ribonucleotide metabolites at cytotoxic concentrations. in vivo studies showed that a significant amount of 5-FdUrd is degraded to its relative base 5FU by thymidine phosphorylase, enzyme for which 5-FdUrd shows a good affinity. This rapid phosphorolytic cleavage of 5-FdUrd to 5FU in vitro, and in vivo represents a major obstacle in delivering intact 5-FdUrd to cells for enhanced cytotoxic action. In addition, the degradation of 5-FdUrd in rat intestinal homogenates and in humans, after oral administration, suggests that 5-FdUrd would scarcely be absorbed as intact 5-FdUrd.

According to a further aspect of the present invention, the compound of the present invention is provided for use in a method of prophylaxis or treatment of cancer in *homo sapiens*. Suitably, the cancer is selected from the group comprising leukemia, pancreatic, prostate, lung, breast and cervical cancer.

In particular, the compound of the present invention is for use in a method of prophylaxis or treatment of cancer in a patient who has developed or has the potential to develop resistance in tumour cells with respect to the activity of 5-fluoracil or 5-fluoro-2'-deoxyuridine in the prophylaxis or the treatment of cancer. For example, the compound of the present invention can be for use in a method of prophylaxis or treatment of cancer in a patient with cells with a lowered level of nucleoside transporter proteins and/or with nucleoside kinase-deficient cells and/or with mycoplasma-infected cells, particularly where the cancer is leukemia. The compound of the present invention can instead of or as well as be for use in a method of prophylaxis or treatment of cancer in a patient who has cells with a raised level of thymidylate synthase (TS).

According to a further aspect of the present invention, there is provided a method of prophylaxis or treatment of cancer comprising administering to a *homo sapiens* patient in need of such treatment an effective dose of a compound of the present invention. Suitably the cancer is selected from the group comprising leukemia, pancreatic, prostate, lung, breast and cervical cancer.

In particular, the present invention comprises a method for treating a patient who has developed or has the potential to develop resistance in tumour cells with respect to the activity of 5-fluoracil or 5-fluoro-2'-deoxyuridine in a method of prophylaxis or treatment of cancer. For example, the method of the present invention can comprise treating a patient with cells with a lowered level nucleoside transporter proteins and/or with nucleoside kinase-deficient cells and/or with mycoplasma-infected cells, particularly where the cancer is leukemia. The method of the present invention for treating a patient can instead of or as well as be for treating a patient that has cells with a raised level of thymidylate synthase (TS).

"Tumour" or "tumour cell" as used in the present application, unless otherwise indicated, refers to both solid tumours and cancers such as leukemia.

Compounds of the present invention can be used for treating a patient with cancer either alone de novo or in conjunction with other cancer therapy. For example, compounds of the present invention can be used in a cancer treatment regime in conjunction with other anti-cancer drugs, such as 5-FU and/or 5-FdUrd either, with or without leucovorin (LV), and/or other anti-cancer drugs. Alternatively, compounds of the present invention can be used where a patient has failed to respond to other anti-cancer drugs, such as for example 5FU and/or 5-FdUrd either with or without leucovorin (LV), or where the patient has shown resistance to other anti-cancer drugs, such as for example 5-FU and/or 5-FdUrd either with or without leucovorin (LV).

Compounds of the present invention where Ar is 1-naphthyl, whether substituted or unsubstituted, are particularly suitable for use in the above uses and methods of the present invention, particularly in a patient who has developed, or who has the potential to develop, resistance in tumour cells, such as, for example, a patient with cells with a lowered level of nucleoside transporter cells and/or with kinase-deficient cells and/or with mycoplasma-infected cells and/or a patient who has cells with a raised level of thymidylate synthase (TS).

According to a further aspect of the present invention, there is provided a pharmaceutical composition comprising a compound of the present invention in combination with a pharmaceutically acceptable carrier, diluent or excipient.

According to another aspect of the present invention, there is provided a method of preparing a pharmaceutical composition comprising the step of combining a compound of the present invention with a pharmaceutically acceptable excipient, carrier or diluent.

According to another aspect of the present invention, there is provided a process for the preparation of a compound of the present invention comprising reacting a compound of formula (II)

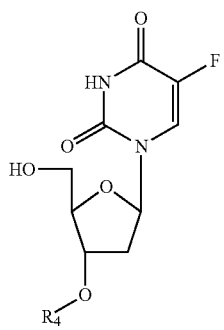

with a compound of formula (III)

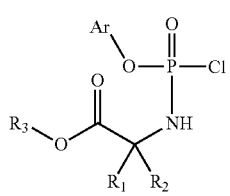

wherein Ar, $R_3$, $R_4$, $R_1$ and $R_2$ have the meanings described above and in claim 1.

The group Ar comprises a substituted or unsubstituted aryl group, wherein the term "aryl group" and the possible substitution of said group is as defined herein. Suitably, Ar is a 5 to 14 membered aromatic ring moiety. Preferably, Ar is carbocyclic. Alternatively, the one or two rings may include 1, 2, 3 or 4 heteroatoms, preferably 1, selected, independently, from O, S and N. Preferably, Ar is a fused carbobicyclic aryl moiety. More preferably, Ar is naphthyl, even more preferably 1-naphthyl i.e. naphthyl linked to P via 0 bonded at the 1-naphthyl position. Suitably, Ar can alternatively be phenyl.

One, two, three or four substituents, which may be the same or different, may be present on Ar and are selected from the group comprising halogen, which may —F, —Cl, —Br or —I; —$NO_2$; —$NH_2$; optionally substituted —$C_{1-3}$alkyl; optionally substituted —$C_{1-3}$alkoxy, preferably methoxy (—$OCH_3$); optionally substituted —$SC_{1-3}$alkyl; —CN; optionally substituted —$COC_{1-3}$alkyl; and optionally substituted —$CO_2C_{1-3}$alkyl; where said optionally substituted groups may be substituted with one or more up to six, preferably three, members independently selected from the group comprising halogen, which may be F, Cl, Br and I, and $NO_2$. Particularly preferred substituents on Ar are electron withdrawing groups such as halogen (preferably chlorine or fluorine), trihalomethyl (preferably trifluoromethyl), cyano and nitro groups.

The substituents may be at any position on the Ar aryl moiety. Where Ar is 1-naphthyl, a single substituent at any of positions 2, 3, 4, 5, 6, 7 or 8 is preferred. Where Ar is phenyl, a single substituent at the 2 (ortho) or 4 (para) position is preferred, more preferred at the 4 position. For example, where Ar is a substituted phenyl, Ar can be 3,5-dichlorophenyl, p-trifluoromethyl-phenyl, p-cyano-phenyl, or p-nitro-phenyl.

Suitably, $R_3$ is a $C_{1-16}$ primary, secondary or tertiary alkyl group and can include carbocyclic moieties; a $C_{5-7}$cyclic alkyl group; or a $C_{1-6}$alkyl$C_{5-11}$aryl group. More suitably, $R_3$ is a $C_{1-10}$ alkyl group or $C_{1-3}$alkyl$C_{5-7}$ aryl group such as benzyl (—$CH_2$—$C_6H_5$). A cyclic alkyl group can be carbocyclic or can contain, in total, one, two or three ring heteroatoms selected independently from O, N and S. Preferably $R_3$ is unsubstituted. Where substituted, substituents are set out below.

Suitably $R_4$ is H or alkoyl i.e. alkyl-C(=O)—, where alkyl is $C_1$ to $C_{10}$.

When $R_1$ and/or $R_2$ is alkyl, they are each independently suitably selected from $C_1$ to $C_{16}$, more suitably from $C_1$ to $C_6$. When $R_1$ and $R_2$ together comprise an alkylene chain, the chain is suitably $C_1$ to $C_6$ and may contain unsaturation and, in total, one, two or three heteroatoms in the chain independently selected from O, N and S. When one of $R_1$ and $R_2$ is attached to N, the total ring size including N and the C atom to which $R_1$ and $R_2$ are attached suitably comprises 4 to 7 members, more suitably 5 members. Any alkyl or alkylene chain comprising $R_1$ and/or $R_2$ can be substituted with one or more substituents set out herein.

When $R_1$ and $R_2$ are different, the C atom to which they are attached is chiral. Preferably, the stereochemistry at an asymmetric centre —$CR_1R_2$ corresponds to an L-amino acid. The stereochemistry at an asymmetric centre —$CR_1R_2$ can, however, correspond to a D-amino acid. Alternatively, mixtures of compounds can be employed having asymmetric centres corresponding to L and D amino acids.

Suitably, $R_1$ and $R_2$ can correspond to the moieties attached to the alpha C atom in a naturally occurring alpha amino acid. By "naturally occurring alpha amino acid" is meant Alanine, Arginine, Asparagine, Aspartic Acid, Cysteine, Cystine, Glycine, Glutamic Acid, Glutamine, Histidine, Hydroxylysine, Hydroxyproline, Isoleucine, Leucine, Lysine, Methionine, Phenylalanine, Proline, Serine, Threonine, Tryptophan, Tyrosine and Valine. One of $R_1$ and $R_2$ can thus be H and one of $R_1$ and $R_2$ can thus be H or alkyl selected from the following moieties or $R_1$ and $R_2$ together can form an alkylene chain selected from the following moieties:

| | |
|---|---|
| $CH_3$— | as present in Alanine |
| $H_2NC(=NH)NH[CH_2]_3$— | as present in Arginine |
| $NH_2C(O)CH_2$— | as present in Aspargine |
| $HO_2CH_2$— | as present in Asparctic Acid |
| $HSCH_2$— | as present in Cysteine |
| $HO_2CH(NH_2)CH_2SSCH_2$— | as present in Cystine |
| H— | as present in Glycine |
| $HO_2CH_2CH_2$— | as present in Glutamic Acid |
| $H_2N(O)CCH_2CH_2$— | as present in Glutamine |
| $C_3N_2HCH_2$— | as present in Histidine |
| $H_2NCH_2CH(OH)CH_2CH_2$— | as present in Hydroxylysine |
| —$CH_2CH(OH)CH_2$— | as present in Hydroxyproline |
| $CH_3CH_2CH(CH_3)$— | as present in Isoleucine |
| $(CH_3)_2CHCH_2$— | as present in Leucine |
| $H_2NCH_2(CH_2)_3$— | as present in Lysine |
| $CH_3SCH_2CH_2$— | as present in Methionine |
| $PhCH_2$— | as present in Phenylalanine |
| —$CH_2CH_2CH_2$— | as present in Proline |
| $OHCH_2$— | as present in Serine |
| $CH_3CH(OH)$— | as present in Threonine |
| $C_8NH_6CH_2$— | as present in Tryptophan |
| $HOC_6H_4CH_2$— | as present in Tyrosine |
| $(CH_3)_2CH$— | as present in Valine. |

By "a pharmaceutically acceptable derivative" is meant any pharmaceutically acceptable salt, ester, salt of such ester, hydrate, solvate, or crystalline form or metabolite or any other compound which upon administration to a recipient is capable of providing (directly or indirectly) a compound of formula (I).

Reference in the present specification to an alkyl group means a branched or unbranched, cyclic or acyclic, saturated or unsaturated (e.g. alkenyl or alkynyl) hydrocarbyl radical. Where cyclic, the alkylene group is preferably $C_3$ to $C_{12}$, more preferably $C_5$ to $C_{10}$, more preferably $C_5$ to $C_7$. Where acyclic, the alkyl group is preferably $C_1$ to $C_{16}$, more preferably $C_1$ to $C_6$.

Reference in the present specification to an aryl group means an aromatic group containing, suitably, 5 to 14 ring atoms. For example Ar is phenyl or naphthyl. The aromatic group may be a heteroaromatic group containing one, two, three or four, preferably one, heteroatoms selected, independently, from the group consisting of O, N and S. Examples of such heteroaromatic groups include pyridyl, pyrrolyl, furanyl and thiophenyl.

The alkyl and aryl groups may be substituted or unsubstituted. Where substituted, there will generally be one to three substituents present, preferably one substituent. Substituents may include halogen atoms, by which is meant F, Cl, Br and I atoms, and halomethyl groups such as $CF_3$ and $CCl_3$; oxygen containing groups such as oxo, hydroxy, carboxy, carboxy$C_{1-16}$alkyl, alkoxy, alkoyl, alkoyloxy, aryloxy, aryloyl and aryloyloxy; nitrogen containing groups such as amino, $C_{1-6}$alkylamino, di$C_{1-6}$alkylamino, cyano, azide and nitro; sulphur containing groups such as thiol, $C_{1-6}$alkylthiol, sulphonyl and sulphoxide; heterocyclic groups which may themselves be substituted; alkyl groups as defined above, which may themselves be substituted; and aryl groups as defined above, which may themselves be substituted, such as phenyl and substituted phenyl. Substituents on said heterocyclic, alkyl and aryl groups are as defined immediately above. Substituents in $R_1$ and/or $R_2$ include moieties to provide compounds in which $R_1$ and $R_2$ correspond to the moieties attached to the alpha C atom in a natural occurring alpha amino acid.

Reference in the present specification to alkoxy and aryloxy groups means, respectively, alkyl-O— (for example where alkyl is $C_1$ to $C_{16}$, preferably $C_1$ to $C_6$) and aryl-O— (for example where aryl is a 5 to 14 membered aromatic mono- or bifused ring moiety, optionally containing 1, 2, 3 or 4 heteroatoms selected, independently, from O, S and N, preferably aryl is phenyl).

Reference in the present specification to alkoyl and aryloyl groups means, respectively, alkyl-CO— (for example where alkyl is $C_1$ to $C_{16}$, preferably $C_1$ to $C_6$) and aryl-CO— (for example where aryl is a 5 to 14 membered aromatic mono or bifused ring moiety, optionally containing 1, 2, 3 or 4 heteroatoms selected, independently, from O, S and N, preferably aryl is phenyl).

Reference in the present specification to alkoyloxy and aryloyloxy means, respectively, alkyl-CO—O (for example where alkyl is $C_1$ to $C_{16}$, preferably $C_1$ to $C_6$) and aryl-CO—O (for example where aryl is a 5 to 14 membered mono- or bifused aromatic ring system, optionally containing 1, 2, 3 or 4 heteroatoms selected, independently, from O, S and N, preferably aryl is phenyl).

Reference in the present specification to heterocyclic groups means groups containing one or more, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

In one embodiment of the present invention, Ar is suitably naphthyl, especially 1-naphthyl i.e. naphthyl linked to P via O bonded at the 1-naphthyl position.

In another embodiment of the present invention, Ar is suitably phenyl.

In one embodiment of the present invention, Ar is substituted. Suitable substituents are set out herein.

In one embodiment of the present invention, Ar is unsubstituted 1-naphthyl.

In one embodiment of the present invention, Ar is unsubstituted phenyl.

In one embodiment of the present invention, $R_4$ is selected from the group consisting of H and acetyl ($CH_3C(=O)$—), especially $R_4$ is H.

In one embodiment of the present invention, $R_3$ is selected from the group consisting of benzyl and members of the group comprising $C_1$ to $C_{10}$ alkyls, especially $R_3$ is selected from n-propyl, n-butyl, n-pentyl and n-hexyl, more especially $R_3$ is n-pentyl.

In one embodiment of the present invention, $R_1$ and $R_2$ correspond to the moieties attached to the alpha C atom in a naturally occurring alpha amino acid, as set out herein. A particularly suitable naturally occurring alpha amino acid is L-alanine such that suitably one of $R_1$ and $R_2$ is H, one of $R_1$ and $R_2$ is $CH_3$ and the C atom to which they are attached has L chirality. In other embodiments, $R_1$ and $R_2$ correspond to the moieties attached to the alpha C atom in a non-naturally occurring alpha amino acid, for example $R_1$ and $R_2$ are both suitably $CH_3$.

The specific features mentioned in the above embodiments are specifically disclosed to be combined together in any and all combinations in compounds of the present invention.

Particularly suitable compounds of the present invention are compounds where Ar is 1-naphthyl, $R_3$ is benzyl, one of $R_1$ and $R_2$ is H, one of $R_1$ and $R_2$ is methyl and the C atom to which $R_1$ and $R_2$ are attached has L-chirality and compounds where Ar is 1-naphthyl, $R_3$ is n-pentyl, one of $R_1$ and $R_2$ is H, one of $R_1$ and $R_2$ is methyl and the C atom to which $R_1$ and $R_2$ are attached has L-chirality. For each compound, $R_4$ is most suitably H.

Conventional treatment of cancer using chemotherapeutics is largely based on the use of nucleoside analogues. These molecules are designed to mimic natural pyrimidine and purine nucleosides. After uptake by the cell, they are phosphorylated by cellular enzymes such as (deoxy)cytidine kinase (dCK), thymidine kinase (TK) and/or nucleo(s)(t)ide kinases. These antimetabolites can subsequently interfere with the de novo synthesis of DNA/RNA precursors to eventually inhibit DNA/RNA synthesis resulting in cytotoxic/static activity (Hatse et al., 1999; Galmarini et al., 2002).

Fluoropyrimidine-based antimetabolites such as fluorouracil (5-FU), capecitabine and 5-fluoro-2'-deoxyuridine (5-FdUrd) are mainly used in the treatment of colon, breast and ovarian carcinoma (de Bruin et al., 2006; Ishikawa et al., 1998; Walko et al., 2005). Intracellularly, these drugs are metabolised to 5-FdUMP, which forms a stable inhibitory complex with thymidylate synthase (TS) and the reduced co-substrate 5,10-methylenetetrahydrofolate, thereby blocking binding of the normal substrate dUMP to the enzyme (Beck et al., 1994; Tanaka et al., 2000; Longley et al, 2003). TS is the enzyme responsible for the conversion of dUMP to TMP and is therefore indispensible for cell proliferation, making it an interesting target for drug design. Among the fluoropyrimidines mentioned above, 5-FdUrd requires only one metabolic conversion, a phosphorylation catalysed by TK to generate 5-FdUMP (Longley et al., 2003). This obligatory phosphorylation is often the rate-limiting step in the metabolism of many anti-cancer drugs (including 5-FdUrd), and is therefore still one of the limiting factors for the therapeutic use of nucleoside analogues. Hence, different strategies to improve the antitumour efficacy of nucleoside analogues have been investigated (Galmarini et al., 2002).

The charged nature of nucleoside monophosphates under physiological conditions results in poor, if any, penetration across the cell membrane (Mehellou et al., 2009). Therefore, the direct administration of phosphorylated molecules to circumvent the first phosphorylation step has little therapeutic advantage. Hence, different strategies for bypassing the rate-limiting phosphorylation using various types of nucleoside 5'-monophosphate prodrugs for more efficient drug-delivery have been explored (Hecker & Erion, 2008). The administration of lipophilic phosphoramidate nucleotide prodrugs (ProTides) has proved successful for several molecules with antiviral/cancer activity (Harris et al., 2001; Congiatu et al., 2006; McGuigan et al., 2010). By masking the charges of the phosphate motif, good passive membrane diffusion of the prodrugs can be accomplished after which the prodrug is rapidly converted intracellularly into the nucleoside monophosphate by enzymatic cleavage (Mehellou et al., 2009).

Mycoplasmas are the smallest self-replicating organisms on earth and are characterized by the lack of a cell wall and a strongly reduced genome (600-1,200 kb). Many of these bacteria have a parasitic lifestyle and reside in the human body causing asymptomatic infections (Razin et al., 1998). It was shown that these prokaryotes tend to preferentially colonize tumour tissue: Huang et al. (2001) reported that 39.7-56% of human gastric, colon, oesophageal, lung and breast cancers are infected with mycoplasmas compared to 20.9-30% in non-tumourigenic tissue. Pehlivan et al. (2005) found >80% of kidney tissue samples of patients suffering renal cell carcinoma to be infected with mycoplasmas compared to 14% in control tissue samples. Chan et al. (1996) reported a 59% infection rate in ovarian cancer tissues and other studies also report a high mycoplasma infection rate in gastric (Sasaki et al., 1995, Yang et al., 2010) and cervical condyloma tissues (Kidder et al., 1998). Due to their reduced set of genes, mycoplasmas lack the pathway for de novo pyrimidine and purine synthesis and therefore express a wide array of salvage nucleo(s)(t)ide-metabolizing enzymes, such as thymidine phosphorylase (TP), deoxycytidine deaminase, etc. (Razin, 1978; Charron & Langelier, 1981; Neale et al., 1983; Tham et al., 1993). Already in 1985 it was observed that mycoplasma-encoded enzymes (e.g. TP), present in contaminated cell cultures, lead to decreased dTTP incorporation in lymphocytes (Sinigaglia & Talmadge, 1985). Recently, it has been demonstrated that these enzymes, in particular the mycoplasma-encoded thymidine phosphorylase, also interfere with the cytostatic activity of several chemotherapeutics, including 5-trifluorothymidine, in vitro (Bronckaers et al., 2008; Jetté et al., 2008; Liekens et al., 2009). Therefore it has been hypothesized that the elimination of mycoplasmas by antibiotics or suppression of mycoplasma-encoded enzymes in human tumour tissue may optimize treatment of cancer patients using purine and pyrimidine antimetabolites (Liekens et al., 2009).

The present invention is derived from the development and assessment of TK-independent phosphoramidate prodrugs of 5-FdUrd and provides compounds that can also be insensitive to the TP-dependent inactivation of its free nucleoside analogue. Compounds of the present invention can thus provide mycoplasma-insensitive nucleoside analogue prodrugs which may optimize treatment of cancer patients using a pyrimidine antimetabolite. From among the presently synthesized phosphoramidate prodrugs of 5-FdUrd, CPF-373 (identified below and mentioned above as a particularly suitable compound of the invention with $R_4$ as H) was chosen for further in depth studies. This molecule contains a naphthyl and benzylalaninyl group to mask the charged 5'-phosphate on 5-FdUMP.

Various mechanisms of tumour cell resistance towards fluoropyrimidines such as 5FU, 5-FdUrd and trifluorothymidine (TFT) have been described, including a decreased activity of crucial drug-activating enzymes (e.g. TK and orotate phosphoribosyltransferase), an increased activity of drug-inactivating enzymes (i.e. thymidine phosphorylase) and/or an upregulation of the target enzymes (e.g. TS) (Agarwal et al., 1999; Murakami et al., 2000; Kosaka et al., 2004). Also, high TP levels found in several types of cancer tissue were reported to be predictive of a poorer prognosis upon treatment with fluoropyrimidines (Kamoshida et al., 2005; Ciaparrone et al., 2006; Koopman et al., 2009), although other studies have not confirmed these findings (Ciccolini et al., 2004; Koopman et al., 2009). The present invention derives from the development of a prodrug for 5-FdUrd, to circumvent possible resistance mechanisms and susceptibility to degradation by catabolic enzymes, present in the tumour micro-environment.

Compounds embodying the present invention, for example CPF-373, are phosphoramidate prodrugs of 5-FdUrd and are described herein and can fulfil these aims. After uptake into the tumour cells, CPF-373, for example, generates 5-FdUMP intracellularly upon enzymatic cleavage. Stability studies and enzymatic/serum studies by $^{31}P$ NMR technology revealed that the prodrug CPF-373, for example, is fully stable in acid and alkaline conditions, but subject to hydrolysis in the presence of serum or carboxypeptidase Y, resulting in the formation of the nucleoside 5'-phosphoramidate derivative. Whereas TK is a key enzyme in the activation of 5-FdUrd, CPF-373, for example, was found to be much less dependent on TK to exert its cytostatic action in both murine (L1210) and human (CEM) cell cultures. Due to the lipophilic nature of ProTides, these molecules can deliver nucleoside-monophosphates directly into the intact tumour cell after conversion to their nucleoside phosphoramidate derivative by enzymes such as carboxyesterases or carboxypeptidases (i.e. carboxypeptidase Y), eliminating the need for an initial phosphorylation by specific nucleoside kinases such as TK. In this regard, CPF-373, for example, may be an adequate tool for the treatment of tumour cells with a modified TK activity (be it acquired or inherent). Also, since TK expression is S-phase-dependent, it is expected that CPF-373, for example, can also efficiently deliver 5-FdUMP in tumour cells that are not in the S-phase of their replication cycle. TS activity studies revealed that, CPF-373, for example, was able to inhibit TS in both wild-type and TK-deficient tumour cell lines, pointing again to an efficient intracellular delivery of the 5'-monophosphate of 5-FdUrd, and its virtual independence of cellular TK for metabolic activation.

Compounds of the present invention, such as CPF-373, are unlikely to be inactivated by catabolic enzymes involved in nucleoside metabolism. Indeed, whereas 5-FdUrd is highly susceptible to enzymatic hydrolysis by TP resulting in the formation of 5-FU and 2-deoxyribose-1-phosphate, its prodrug, for example CPF-373, is not a substrate for prokaryotic (i.e. *E. coli*) or mammalian (i.e. human erythrocyte) TP. Also, uridine phosphorylase does not recognize, for example CPF-373, as a substrate, whereas 5-FdUrd is (poorly, but measurably) hydrolyzed by this enzyme. Several studies revealed that many tumour cells have elevated levels of TP, which also acts as an angiogenic factor (Koopman et al., 2009; Bronckaers et al., 2009). Moreover, there are several reports on the preferential colonization of tumour tissue by mycoplasmas (Sasaki et al., 1995; Chan et al., 1996; Huang et al., 2001; Pehlivan et al., 2005) which interfere with the cytostatic activity of several conventional chemotherapeutics in vitro through its encoded TP (Bronckaers et al., 2008; Jetté et al., 2008; Liekens et al., 2009). The present observations that 5-FdUrd, but not, for example, CPF-373, markedly loses cytostatic activity when the tumour cells are infected by (TP-expressing) mycoplasmas, is in full agreement with these observations. Therefore, the administration of a TP-insensitive anti-cancer prodrug such as CPF-373, demonstrated to be chemically stable at extreme pH conditions, may further improve cancer chemotherapy. In conclusion, ProTides, such as CPF-373, provide an interesting new approach towards the development of more resilient anti-cancer drugs. For instance CPF-373 may have at least several advantages over its parent drug 5-FdUrd: it exerts its cytostatic activity independent of TK and it is resistant to metabolic breakdown by TP, an enzyme that is often upregulated in tumours or may be externally expressed by mycoplasma infection of the tumour tissue.

The compound having formula I or the pharmaceutical composition according to the present invention can be administered to a *homo sapiens* patient by any suitable means.

The medicaments employed in the present invention can be administered by oral or parenteral routes, including intravenous, intramuscular, intraperitoneal, subcutaneous, transdermal, airway (aerosol), rectal, vaginal and topical (including buccal and sublingual) administration.

For oral administration, the compounds of the invention will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while cornstarch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In general a suitable dose will be in the range of 0.1 to 300 mg per kilogram body weight of the recipient per day. A preferred lower dose is 0.5 mg per kilogrm body weight of recpient per day, a more preferred lower dose is 6 mg per kilogram body weight of recipient per day, an even more preferred lower dose is 10 mg per kilogram body weight per recipient per day. A suitable dose is preferably in the range of 6 to 150 mg per kilogram body weight per day, and most preferably in the range of to 100 mg per kilogram body weight per day. The desired dose is preferably presented as two, three, four, five or six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Examples of the present invention will now be described, by way of example only, with reference to the accompanying drawings comprising FIGS. 1 to 11, wherein:

FIG. 1 shows structural formula of 5-FdUrd and its phosphoramidate prodrug CPF-373;

Figure 10A:
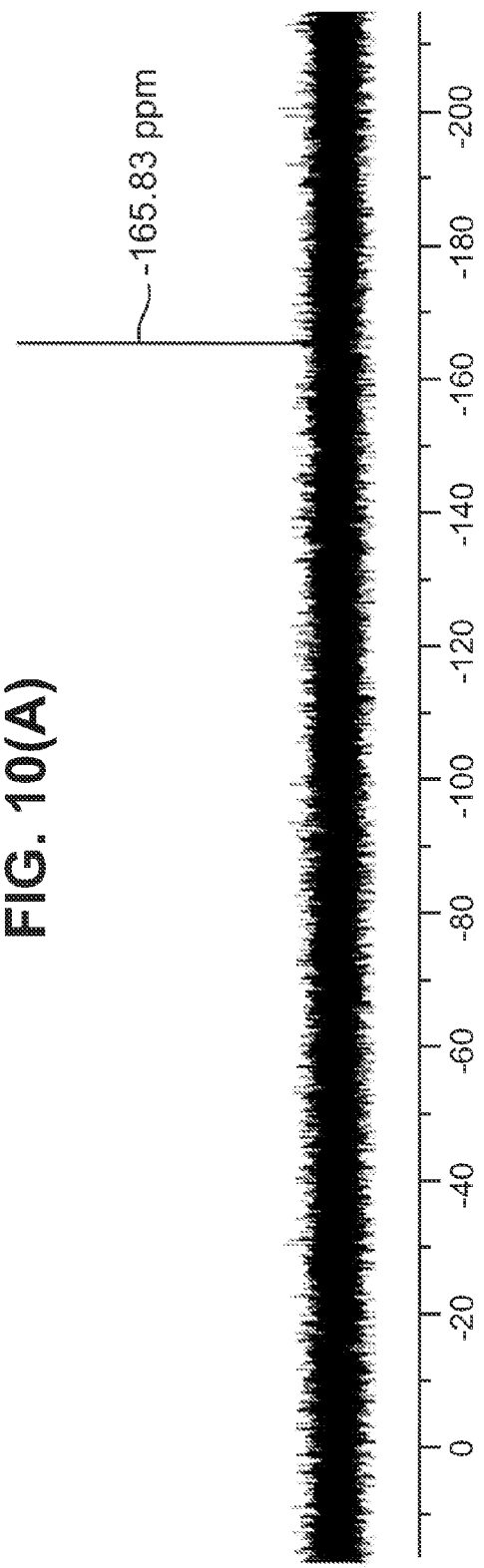
Figure 10B:

FIG. 10 shows spectra of nucleoside and base in potassium phosphate buffer (205 nM) by $^{19}$F NMR: a) 5-FdUrd submitted to the phosphorylase assay in absence of enzyme (A); b) Result after the addition of enzyme (TP) (B); and FIG. 11 shows spectra of prodrug compound CPF-373 in phosphorylase assay: a) prodrug CPF-373 under conditions of the assay in absence of the enzyme (TP) (A); b) prodrug CPF-373 submitted to the action of thymidine phosphorylase (TP) (B).

COMPOUND SYNTHESIS

With reference to FIG. 1 and Schemes 1 to 3 below, compounds of the present invention, as exemplified by the compound CPF-373 (1), have been synthesized using phosphorochloridate chemistry, which phosphorochloridate chemistry has previously been reported by McGuigan et al. (1993, 1996, 1997). For example, arylphosphorodichlorophosphate (2) has been prepared coupling 1-naphthol (3) with phosphorus oxychloride (4) in the presence of Et$_3$N (Scheme 1) and this was allowed to react with L-alanine benzyl ester tosylate (5) in the presence of Et$_3$N to generate the phosphorochloridate derivative (6) (Scheme 2). The nucleoside 5-FdUrd (7) was converted to the 5' ProTide by coupling with the phosphorochloridate derivative (6) in THF, in the presence of N-methyl imidazole (NMI) to give the target compound CPF-373 (1) (Scheme 3). The sample was obtained as a mixture of two diastereoisomers as confirmed by the presence of two peaks in the $^{31}$P NMR.

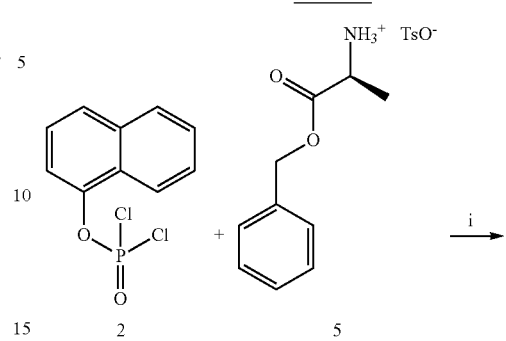

Scheme 2.

Reagents and Conditions: (i) dry Et$_3$N, CH$_2$Cl$_2$, -78° C., 1 h then R.T., 3 h.

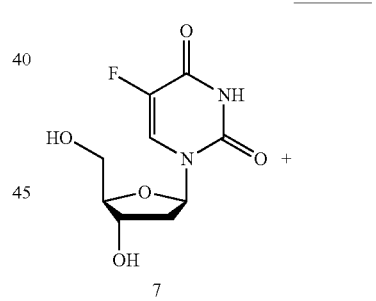

Scheme 3.

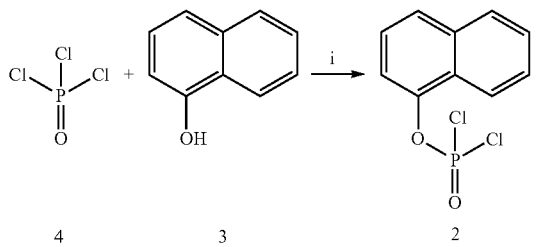

Scheme 1.

Reagents and Conditions: (i) 1-naphthol (3), phosphorus oxychloride (4), dry Et$_2$O, dry Et$_3$N, -78° C., 30 min. then R.T., 3 h.

-continued

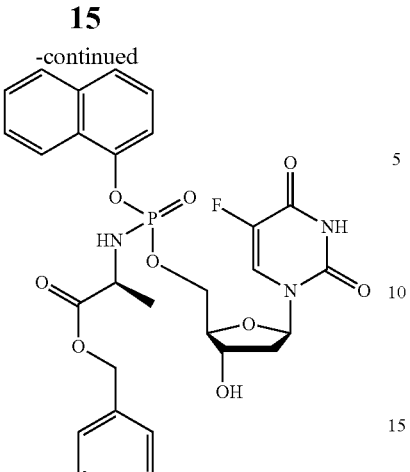

1

Reagents and Conditions: (i) NMI, dry THF, 10 min., then phosphorochloridate (6), R.T., overnight.

Anhydrous solvents were obtained from Aldrich and used without further purification. All reactions were carried out under an argon atmosphere. Reactions were monitored with analytical TLC on Silica Gel 60-F254 precoated aluminium plates and visualised under UV (254 nm) and/or with $^{31}$P NMR spectra. Column chromatography was performed on silica gel (35-70 μM). Proton ($^{1}$H), carbon ($^{13}$C), phosphorus ($^{31}$P) and fluorine ($^{19}$F) NMR spectra were recorded on a Bruker Avance 500 spectrometer at 25° C. Spectra were auto-calibrated to the deuterated solvent peak and all $^{13}$C NMR and $^{31}$P NMR were proton-decoupled. Analytical HPLC was conducted by Varian Prostar (LC Workstation-Varian prostar 335 LC detector) using Varian Polaris C18-A (10 μM) as an analytic column.

Low and High resolution mass spectra were performed as a service by Birmingham University, using electrospray (ES). CHN microanalysis was performed as a service by MEDAC Ltd., Surrey.

Standard Procedure A: Synthesis of Dichlorophosphate (2).

Phosphorus oxychloride (1.0 equiv) was added to a solution of 1-naphthol (1.0 equiv) in diethyl ether under argon atmosphere, then anhydrous triethylamine (1.0 equiv) was added dropwise at –78° C. and the resulting reaction mixture was stirred for 1 h. Subsequently the reaction mixture was allowed to slowly warm up to room temperature for 3 h. Formation of the desired compound was monitored by $^{31}$P NMR. The resulting mixture was filtered and then evaporated in vacuo under nitrogen to afford the crude colourless oil as product, which was used without further purification in the next step.

Synthesis of 1-Naphthyl dichlorophosphate (2)

Prepared according to Standard Procedure A, from 1-naphthol (3.00 g, 20.81 mmol), phosphorus oxychloride (1.94 mL, 20.81 mmol), triethylamine (2.9 mL, 20.81 mmol) and anhydrous diethyl ether (70 mL). After 1 h at –78° C. the reaction was left to rise to room temperature and stirred for 3 h. The crude product was obtained as an oil. The resulting mixture was filtered and then evaporated in vacuo, after purification by column chromatography eluting with hexane-EtOAc, (1:1) to afford a colorless oil (4.59 g, 84%) [$R_f$=0.93 (hexane-EtOAc, 1:1)], $^{31}$P NMR (202 MHz, CDCl$_3$): δ$_P$ 5.07; $^{1}$H NMR (500 MHz, CDCl$_3$): δ$_H$ 7.52-7.71 (m, 4H, ArH), 7.86-7.89 (m, 1H, ArH), 7.95-7.98 (m, 1H, ArH), 8.16-8.19 (m, 1H, ArH).

Standard Procedure B: Synthesis of Phosphorochloridate (6).

A solution of aryl phosphorodichloridate (1.0 equiv.) and appropriate amino acid ester salt (1.0 equiv.) in dichloromethane under argon atmosphere was added dropwise to anhydrous triethylamine (2.0 equiv.) at –78° C. After 1 h the reaction mixture was allowed to slowly warm to room temperature for 3 h and the formation of the desired compound was monitored by $^{31}$P NMR. The reaction mixture was concentrated under reduced pressure, the residue was redissolved in diethyl ether, filtered and evaporated in vacuo under nitrogen to afford a crude colourless oil, which in some cases was used without further purification in the next step. The aryl phosphorochloridate synthesized was purified by column chromatography eluting with hexane-EtOAc, (7:3) to afford the title compound as a colorless oil.

Synthesis of 1-Naphthyl(benzyl-L-alaninyl)phosphorochloridate (6)

The phosphorochloridate was prepared using 1-naphthyl dichlorophosphate (2.50 g, 9.57 mmol), L-alanine benzyl ester tosylate salt (3.36 g, 9.57 mmol), dry triethylamine (2.66 mL, 19.14 mmol) and dry dichloromethane (35.7 mL) according to the general procedure B. Purification by column chromatography eluting with hexane-EtOAc, (7:3) afforded the title compound as a colourless oil (1.82 g, 47%) [$R_f$=0.90 (hexane-EtOAc, 7:3)], $^{31}$P NMR (202 MHz, CDCl$_3$, mixture of diastereoisomers): δ$_P$ 7.92, 8.14 (Int.: 1.00:1.00); $^{1}$H NMR (500 MHz, CDCl$_3$, mixture of diastereoisomers with a ratio of 1:1): δ$_H$ 1.42-1.45 (m, 3H, CHCH$_3$), 4.20-4.23 (m, 1H, CHCH$_3$), 4.78-4.81 (m, 1H, NH), 5.09 (s, 2H, OCH$_2$Ph), 7.09-7.73 (m, 11H, ArH), 7.97-8.12 (m, 1H, ArH).

Standard Procedure C: Synthesis of the Nucleoside Phosphoramidate (1).

A solution of the appropriate nucleoside (1.0 equiv.) in dry THF (10 mL) was added to NMI (5.0 equiv.) at room temperature under argon atmosphere. After 10 min the reaction mixture was added dropwise to a solution of phosphorochloridate (3.0 equiv) in anhydrous THF. The reaction was stirred at room temperature overnight and evaporated in vacuo. The oil obtained was dissolved in CH$_2$Cl$_2$, washed twice with H$_2$O, then with HCl 0.5 M or in alternative the crude product was washed with diethyl ether. Then the crude product was purified by column chromatography on silica, eluting with CH$_2$Cl$_2$-MeOH as a gradient to afford the phosphoramidate.

Synthesis of 5-Fluoro-2'deoxyuridine-5'-O-[α-naphthyl(benzyl-L-alaninyl)]phosphate (1)

The phosphoramidate was prepared using 5-Fluoro-2'deoxyuridine (0.25 g, 1.01 mmol), NMI (0.40 mL, 5.07 mmol) and 1-naphthyl (benzyl-L-alaninyl) phosphorochloridate (0.82 g, 3.04 mmol) according to the general procedure C. Purification by gradient column chromatography eluting with CH$_2$Cl$_2$ until CH$_2$Cl$_2$-MeOH (95:5) afforded the title compound as a colourless solid (47.0 mg, 8%) [$R_f$=0.19 (CH$_2$Cl$_2$-MeOH, 95:5)], (Found: MNa$^+$, 636.1520. C$_{29}$H$_{29}$N$_3$O$_9$FNaP requires [MNa$^+$], 636.1523); $^{31}$P NMR (202 MHz, MeOD, mixture of diastereoisomers): δ$_P$ 4.24, 4.59; $^{19}$F NMR (470 MHz, MeOD): δ$_F$ –167.36, –167.18; $^{1}$H NMR (500 MHz, MeOD): δ$_H$ 1.34-1.38 (m, 3H, CHCH$_3$), 1.67-1.79 (m, 1H, H-2'), 2.08-2.17 (m, 1H, H-2'), 4.03-4.15 (m, 2H, CHCH$_3$, H-4'), 4.24-4.36 (m, 3H, CH$_2$OP, H-3'), 5.08 (d, 1H, J=12.0 Hz, OCHHPh), 5.13 (d, 1H, J=12.0 Hz, OCHHPh), 6.09-6.16 (m, 1H, H-1'), 7.27-7.45 (m, 6H, ArH), 7.47-7.55 (m, 3H, ArH), 7.67-7.72 (m, 2H, ArH, H-6), 7.86-7.90 (m, 1H, ArH), 8.12-8.18 (m, 1H, ArH); $^{13}$C NMR (125 MHz, MeOD): δ$_C$ 20.3 (d, $^{3}J_{C-P}$=7.6 Hz, CH$_3$), 20.5

(d, $^3J_{C\text{-}P}$=6.5 Hz, CH$_3$), 40.8 (CH$_2$), 40.9 (CH$_2$), 51.8 (CH), 51.9 (CH), 67.6 (d, $^2J_{C\text{-}P}$=5.3 Hz, CH$_2$), 67.8 (d, $^2J_{C\text{-}P}$=5.2 Hz, CH$_2$), 68.0 (CH$_2$), 68.1 (CH$_2$), 72.0 (CH), 72.1 (CH), 86.7 (d, $^3J_{C\text{-}P}$=8.1 Hz, CH), 86.8 (d, $^3J_{C\text{-}P}$=8.1 Hz, CH), 86.9 (CH), 87.0 (CH), 116.2 (d, $^3J_{C\text{-}P}$=3.3 Hz, CH), 116.5 (d, $^3J_{C\text{-}P}$=3.5 Hz, CH), 122.6 (CH), 125.3 (CH), 125.4 (CH), 125.6 (CH), 125.7 (CH), 126.2 (CH), 126.5 (CH), 126.6 (CH), 127.6 (CH), 127.7 (CH), 127.8 (C), 127.9 (C), 128.0 (CH), 128.1 (CH), 128.9 (CH), 129.0 (CH), 129.4 (CH), 129.5 (CH), 129.6 (CH), 129.7 (CH), 136.2 (C), 137.1 (C), 137.2 (C), 141.6 (d, $^1J_{C\text{-}F}$=233.8 Hz, C), 141.7 (d, $^1J_{C\text{-}F}$=233.9 Hz, C), 147.8 (d, $^2J_{C\text{-}P}$=7.7 Hz, C), 147.9 (d, $^2J_{C\text{-}P}$=7.4 Hz, C), 150.5 (d, $^4J_{C\text{-}F}$=4.0 Hz, C), 159.3 (d, $^2J_{C\text{-}F}$=26.1 Hz, C), 174.6 (d, $^3J_{C\text{-}P}$=5.0 Hz, C), 174.9 (d, $^3J_{C\text{-}P}$=4.3 Hz, C), m/z (ES) 636 (MH$^+$, 100%), Reverse HPLC eluting with (H$_2$O/MeOH from 100/0 to 0/100) in 45 min., showed two peaks of the diastereoisomers with $t_R$ 34.23 min. and $t_R$ 34.59 min. Anal. Calcd for C$_{29}$H$_{29}$FN$_3$O$_9$P: C, 56.77; H, 4.76; N, 6.85. Found: C, 56.57; H, 5.06; N, 6.72.

Radioactive Pyrimidine Deoxynucleosides

[5-$^3$H]dCyd (radiospecificity: 22 Ci/mmol) and [5-$^3$H] dUrd (radiospecificity: 15.9 Ci/mmol) were obtained from Moravek Biochemicals Inc. (Brea, Calif.).

Standard Procedure D: Synthesis of Phosphoramidates (NMI Method)

To a stirring solution of 5-F-dUrd (1.0 eq.) in anhydrous THF, an appropriate phosphorochloridate (3.0 eq.) dissolved in anhydrous THF was added dropwise under an Ar atmosphere. To that reaction mixture at −78° C. was added dropwise over 5 minutes NMI (5.0 eq.). After minutes, the reaction mixture was let to rise to room temperature and stirred overnight. The solvent was removed under vacuum and the residue was re-dissolved in DCM and washed with 0.5 M HCl three times. The organic layer was dried over MgSO$_4$, filtered, reduced to dryness and purified by column chromatography with gradient of eluent (DCM/MeOH 99:1 to 97:3 to 95:5).

Standard Procedure E: Synthesis of Phosphoramidates (tBuMgCl Method)

To a stirring solution of 5-FdUrd (1.0 eq.) dissolved in anhydrous THF, tBuMgCl (1.1 mol eq. 1M solution in THF) was added dropwise under an Ar atmosphere, followed by addition (after 30 min.) of the appropriate phosphorochloridate (2.0 mol eq.) dissolved in anhydrous THF. The resulting reaction mixture was stirred at room temperature overnight. The solvent was removed under reduced pressure and the residue was purified by column chromatography using gradient of eluent (DCM/MeOH 99:1 to 97:3 to 95:5)

5-Fluoro-2'-deoxyuridine-5'-O-[phenyl(benzoxy-L-alaninyl)]phosphate (CPF381)

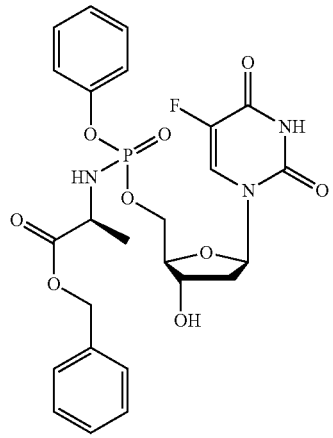

The phosphoramidate was prepared using 5-fluoro-2'-deoxyuridine (0.40 g, 1.62 mmol), tert-butylmagnesium chloride in tetrahydrofuran ($^t$BuMgCl) (1.0 M, 2.43 mL, 2.43 mmol) and phenyl(benzoxy-L-alaninyl)phosphorochloridate (1.08 g, 3.20 mmol) according to general procedure E. Purification by gradient column chromatography on silica, eluting with CH$_2$Cl$_2$ until CH$_2$Cl$_2$-MeOH (95:5) afforded the title compound as a colourless solid (71.0 mg, 8%) [R$_f$=0.35 (CH$_2$Cl$_2$-MeOH, 95:5)], (Found: MNa$^+$, 586.1360. C$_{25}$H$_{27}$N$_3$O$_9$NaPF requires [MNa$^+$], 586.1367); $^{31}$P NMR (202 MHz, MeOD): $\delta_P$ 3.74, 4.14; $^{19}$F NMR (470 MHz, MeOD): $\delta_F$ −167.57, −167.46; $^1$H NMR (500 MHz, MeOD): $\delta_H$ 1.35 (d, 3H, J=7.4 Hz, CHCH$_3$, one diast.), 1.37 (d, 3H, J=6.9 Hz, CHCH$_3$, one diast.), 1.96-2.32 (m, 2H, H-2'), 3.95-4.08 (m, 2H, CHCH$_3$, H-4'), 4.23-4.34 (m, 3H, CH$_2$OP, H-3'), 5.13 (br d, 1H, J=12.3 Hz, OCHHPh), 5.16 (br d, 1H, J=12.3 Hz, OCHHPh, one diast.), 5.17 (br d, 1H, J=12.2 Hz, OCHHPh, one diast.), 6.16-6.22 (m, 1H, H-1'), 7.17-7.25 (m, 3H, ArH), 7.26-7.40 (m, 7H, ArH), 7.81-7.85 (m, 1H, H-6); $^{13}$C NMR (125 MHz, MeOD): $\delta_C$ 20.2 (d, $^3J_{C\text{-}P}$=7.5 Hz, CH$_3$), 20.4 (d, $^3J_{C\text{-}P}$=6.2 Hz, CH$_3$), 40.6 (CH$_2$), 40.9 (CH$_2$), 51.6 (CH), 51.8 (CH), 67.5 (d, $^2J_{C\text{-}P}$=5.3 Hz, CH$_2$), 67.6 (d, $^2J_{C\text{-}P}$=5.5 Hz, CH$_2$), 68.0 (CH$_2$), 71.8 (CH), 71.9 (CH), 86.6 (d, $^3J_{C\text{-}P}$=8.0 Hz, CH), 86.8 (d, $^3J_{C\text{-}P}$=8.3 Hz, CH), 86.9 (CH), 87.0 (CH), 121.4 (d, $^3J_{C\text{-}P}$=5.1 Hz, CH), 121.5 (d, $^3J_{C\text{-}P}$=5.6 Hz, CH), 125.5 (d, $^5J_{C\text{-}P}$=3.2 Hz, CH), 125.8 (d, $^5J_{C\text{-}P}$=3.2 Hz, CH), 126.3 (CH), 129.0 (CH×2), 129.3 (CH×2), 129.6 (CH×2), 130.8 (CH×2), 140.9 (C), 141.6 (d, $^1J_{C\text{-}F}$=233.6 Hz, C), 141.7 (d, $^1J_{C\text{-}F}$=233.6 Hz, C), 150.7 (d, $^4J_{C\text{-}F}$=5.7 Hz, C), 152.1 (d, $^2J_{C\text{-}P}$=6.5 Hz, C), 159.2 (d, $^2J_{C\text{-}F}$=26.3 Hz, C), 174.6 (d, $^3J_{C\text{-}P}$=4.9 Hz, C), 174.7 (d, $^3J_{C\text{-}P}$=4.9 Hz, C), m/z (ES) 586 (MNa$^+$, 100%); Reverse-phase HPLC eluting with H$_2$O/MeOH from 100/0 to 0/100 in 45 minutes, 1 ml/min, $\lambda$=275 nm, showed one peak of the mixture of diastereoisomers with $t_R$ 25.08 min. (97%).

5-Fluoro-2'-deoxyuridine-5'-O-[phenyl(methoxy-L-alaninyl)]phosphate (CPF382)

Reference Example

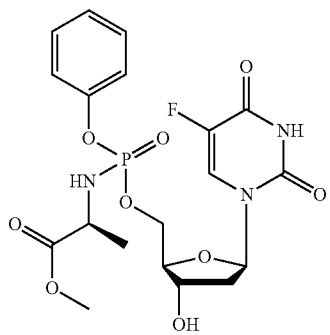

The phosphoramidate was prepared using 5-fluoro-2'-deoxyuridine (0.25 g, 1.01 mmol), N-methylimidazole (NMI) (0.40 mL, 5.07 mmol) and phenyl(methoxy-L-alaninyl)phosphorochloridate (0.84 g, 3.04 mmol) according to general procedure D. Purification by gradient column chromatography eluting with CH$_2$Cl$_2$ until CH$_2$Cl$_2$-MeOH (95:5) afforded the title compound as a colourless solid (16.0 mg, 4%) [R$_f$=0.30 (CH$_2$Cl$_2$-MeOH, 95:5)], (Found: MNa$^+$, 510.1045. C$_{19}$H$_{23}$N$_3$O$_9$NaPF requires [MNa$^+$], 510.1054);

$^{31}$P NMR (202 MHz, MeOD): $TM_P$ 3.79, 4.09; $^{19}$F NMR (470 MHz, MeOD): $TM_F$ −167.78, −167.72; $^{1}$H NMR (500 MHz, MeOD): $TM_H$ 1.34 (d, 3H, J=7.1 Hz, CHCH$_3$, one diast.), 1.36 (d, 3H, J=7.1 Hz, CHCH$_3$, one diast.), 2.02-2.16 (m, 1H, H-2'), 2.25-2.34 (m, 1H, H-2'), 3.69 (s, 3H, OCH$_3$, one diast.), 3.70 (s, 3H, OCH$_3$, one diast.), 3.93-4.02 (m, 1H, CHCH$_3$), 4.08-4.13 (m, 1H, H-4'), 4.27-4.45 (m, 3H, CH$_2$OP, H-3'), 6.20-6.29 (m, 1H, H-1'), 7.18-7.28 (m, 3H, ArH), 7.35-7.40 (m, 2H, ArH), 7.85 (d, 1H, $^3J_{H-F}$=6.4 Hz, H-6); $^{13}$C NMR (125 MHz, MeOD): $TM_C$ 20.2 (d, $^3J_{C-P}$=7.5 Hz, CH$_3$), 20.5 (d, $^3J_{C-P}$=6.7 Hz, CH$_3$), 40.8 (CH$_2$), 40.9 (CH$_2$), 51.5 (CH$_3$), 51.6 (CH$_3$), 52.7 (CH), 52.8 (CH), 67.5 (d, $^2J_{C-P}$=5.5 Hz, CH$_2$), 67.6 (d, $^2J_{C-P}$=5.1 Hz, CH$_2$), 72.0 (CH), 72.1 (CH), 86.7 (d, $^3J_{C-P}$=8.2 Hz, CH), 86.8 (d, $^3J_{C-P}$=8.2 Hz, CH), 86.9 (CH), 87.0 (CH), 121.2 (d, $^3J_{C-P}$=4.5 Hz, CH), 121.4 (d, $^3J_{C-P}$=4.7 Hz, CH), 125.6 (d, $^5J_{C-P}$=2.9 Hz, CH), 125.9 (d, $^5J_{C-P}$=2.9 Hz, CH), 126.2 (CH), 130.8 (CH), 130.9 (CH), 141.6 (d, $^1J_{C-F}$=233.8 Hz, C), 141.7 (d, $^1J_{C-F}$=233.9 Hz, C), 150.6 (d, $^4J_{C-F}$=3.6 Hz, C), 152.1 (d, $^2J_{C-P}$=6.8 Hz, C), 152.2 (d, $^2J_{C-P}$=6.8 Hz, C), 159.4 (d, $^2J_{C-F}$=26.0 Hz, C), 175.2 (d, $^3J_{C-P}$=4.8 Hz, C), 175.5 (d, $^3J_{C-P}$=3.7 Hz, C), m/z (ES) 510 (MNa$^+$, 100%); Reverse-phase HPLC eluting with H$_2$O/MeOH from 100/0 to 0/100 in 45 minutes, 1 ml/min, ⌊=275 nm, showed two peaks of the diastereoisomers with $t_R$ 23.11 min. and $t_R$ 24.11 min. (74%:24%).

5-Fluoro-2'-deoxyuridine-5'-O-[phenyl(ethoxy-L-alaninyl)]phosphate (CPF383)

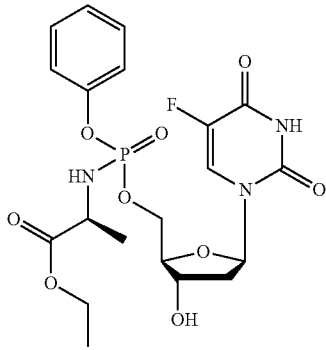

The phosphoramidate was prepared using 5-fluoro-2'deoxyuridine (0.10 g, 0.40 mmol), N-methylimidazole (NMI) (0.16 mL, 2.03 mmol) and phenyl(ethoxy-L-alaninyl)phosphorochloridate (0.35 g, 1.21 mmol) according to general procedure D. Purification by gradient column chromatography eluting with CH$_2$Cl$_2$ until CH$_2$Cl$_2$-MeOH (95:5) afforded the title compound as a colourless solid (10.0 mg, 5%) [R$_f$=0.11 (CH$_2$Cl$_2$-MeOH, 95:5)], (Found: MNa$^+$, 524.1202. C$_{20}$H$_{25}$N$_3$O$_9$NaPF requires [MNa$^+$], 524.1210); $^{31}$P NMR (202 MHz, MeOD): $TM_P$ 3.83, 4.11; $^{19}$F NMR (470 MHz, MeOD): $TM_F$ −167.67, −167.61; $^{1}$H NMR (500 MHz, MeOD): $TM_H$ 1.25 (t, 3H, J=7.1 Hz, CH$_2$CH$_3$, one diast.), 1.26 (t, 3H, J=7.1 Hz, CH$_2$CH$_3$, one diast.), 1.34 (d, 3H, J=7.2 Hz, CHCH$_3$, one diast.), 1.36 (d, 3H, J=7.2 Hz, CHCH$_3$, one diast.), 2.02-2.15 (m, 1H, H-2'), 2.24-2.34 (m, 1H, H-2'), 3.90-4.00 (m, 1H, CHCH$_3$,), 4.08-4.19 (m, 3H, CH$_2$CH$_3$, H-4'), 4.27-4.45 (m, 3H, CH$_2$OP, H-3'), 6.20-6.28 (m, 1H, H-1'), 7.18-7.28 (m, 3H, ArH), 7.34-7.39 (m, 2H, ArH), 7.85 (d, 1H, $^3J^{H-F}$=6.4 Hz, H-6); $^{13}$C NMR (125 MHz, MeOD): $TM_C$ 14.4 (CH$_3$), 15.4 (CH$_3$), 20.3 (d, $^3J_{C-P}$=7.6 Hz, CH$_3$), 20.5 (d, $^3J_{C-P}$=6.5 Hz, CH$_3$), 40.8 (CH$_2$), 40.9 (CH$_2$), 51.6 (CH), 51.7 (CH), 62.4 (CH$_2$), 62.5 (CH$_2$), 67.5 (d, $^2J_{C-P}$=5.4 Hz, CH$_2$), 67.6 (d, $^2J_{C-P}$=5.4 Hz, CH$_2$), 72.0 (CH), 72.1 (CH), 86.7 (d, $^3J_{C-P}$=8.1 Hz, CH), 86.8 (d, $^3J_{C-P}$=8.3 Hz, CH), 86.9 (CH), 87.0 (CH), 121.3 (d, $^3J_{C-P}$=4.8 Hz, CH), 121.4 (d, $^3J_{C-P}$=4.6 Hz, CH), 125.6 (d, $^5J_{C-P}$=4.6 Hz, CH), 125.8 (d, $^5J_{C-P}$=4.8 Hz, CH), 126.3 (CH), 130.8 (CH), 130.9 (CH), 141.6 (d, $^1J_{C-F}$=233.7 Hz, C), 141.8 (d, $^1H_{C-F}$=233.8 Hz, C), 150.8 (br C), 152.0 (d, $^2J_{C-P}$=7.1 Hz, C), 152.1 (d, $^2J_{C-P}$=7.1 Hz, C), 159.6 (d, $^2J_{C-F}$=26.0 Hz, C), 174.8 (d, $^3J_{C-P}$=5.4 Hz, C), 175.1 (d, $^3J_{C-P}$=4.4 Hz, C), m/z (ES) 524 (MNa$^+$, 100%); Reverse-phase HPLC eluting with H$_2$O/MeOH from 100/0 to 0/100 in 45 minutes, 1 ml/min, ⌊=275 nm, showed two peaks of the diastereoisomers with $t_R$ 25.63 min. and $t_R$ 26.40 min. (71%:27%).

5-Fluoro-2'deoxyuridine-5'-O-[phenyl(isopropoxy-L-alaninyl)]phosphate (CPF-384)

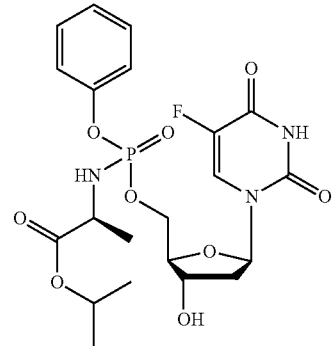

The phosphoramidate was prepared using 5-fluoro-2'-deoxyuridine (0.25 g, 1.01 mmol), N-methylimidazole (NMI) (0.40 mL, 5.07 mmol) and phenyl(isopropoxy-L-alaninyl)phosphorochloridate (0.93 g, 3.04 mmol) according to general procedure D. Purification by gradient column chromatography eluting with CH$_2$Cl$_2$ until CH$_2$Cl$_2$-MeOH (95:5) afforded the title compound as a colourless solid (31.0 mg, 6%) [R$_f$=0.21 (CH$_2$Cl$_2$-MeOH, 95:5)], (Found: MNa$^+$, 538.1370. C$_{21}$H$_{27}$N$_3$O$_9$NaPF requires [MNa$^+$], 538.1367); $^{31}$P NMR (202 MHz, MeOD): $TM_P$ 3.87, 4.13; $^{19}$F NMR (470 MHz, MeOD): $TM_F$ −167.64, −167.56; $^{1}$H NMR (500 MHz, MeOD): $TM_H$ 1.22-1.26 (m, 6H, CH(CH$_3$)$_2$), 1.33 (d, 3H, J=7.1 Hz, CHCH$_3$, one diast.), 1.35 (d, 3H, J=7.1 Hz, CHCH$_3$, one diast.), 2.00-2.15 (m, 1H, H-2'), 2.23-2.34 (m, 1H, H-2'), 3.88-3.96 (m, 1H, CHCH$_3$), 4.08-4.14 (m, 1H, H-4'), 4.27-4.45 (m, 3H, CH$_2$OP, H-3'), 4.98 (hept, 1H, J=6.1 Hz, CH(CH$_3$)$_2$), 6.20-6.29 (m, 1H, H-1'), 7.17-7.29 (m, 3H, Ar—H), 7.34-7.40 (m, 2H, Ar—H), 7.84 (d, 1H, $^3J_{H-F}$=6.4 Hz, H-6); $^{13}$C NMR (125 MHz, MeOD): $TM_C$ 20.3 (d, $^3J_{C-P}$=7.6 Hz, CH$_3$), 20.5 (d, $^3J_{C-P}$=6.4 Hz, CH$_3$), 21.9 (CH$_3$×2), 22.0 (CH$_3$×2), 40.8 (CH$_2$), 40.9 (CH$_2$), 51.7 (CH), 51.8 (CH), 67.5 (d, $^2J_{C-P}$=5.4 Hz, CH$_2$), 67.6 (d, $^2J_{C-P}$=5.2 Hz, CH$_2$), 70.2 (CH), 70.3 (CH), 72.0 (CH), 72.1 (CH), 86.6 (d, $^3J_{C-P}$=8.2 Hz, CH), 86.8 (d, $^3J_{C-P}$=8.2 Hz, CH), 86.9 (CH), 87.0 (CH), 121.2 (d, $^3J_{C-P}$=4.7 Hz, CH), 121.4 (d, $^3J_{C-P}$=4.9 Hz, CH), 125.6 (d, $^5J_{C-P}$=7.1 Hz, CH), 125.9 (d, $^5J_{C-P}$=7.1 Hz, CH), 126.3 (CH), 130.8 (CH), 130.9 (CH), 141.8 (d, $^1J_{C-F}$=234.5 Hz, C), 141.9 (d, $^1J_{C-F}$=234.4 Hz, C), 150.7 (d, $^4J_{C-F}$=3.7 Hz, C), 152.0 (d, $^3J_{C-P}$=6.2 Hz, C), 152.1 (d, $^3J_{C-P}$=6.2 Hz, C), 159.3 (d, $^2J_{C-F}$=26.3 Hz, C), 159.4 (d, $^2J_{C-F}$=26.0 Hz, C), 174.3 (d, $^3J_{C-P}$=5.6 Hz, C), 174.6 (d, $^3J_{C-P}$=4.6 Hz, C), m/z (ES) 538 (MNa$^+$, 100%); Reverse-phase HPLC eluting with H$_2$O/MeOH from 100/0 to 0/100 in 45 minutes, 1 ml/min, ⌊=275 nm, showed two peaks of the diastereoisomers with $t_R$ 28.93 min. and $t_R$ 29.45 min. (44%:52%).

5-Fluoro-2'deoxyuridine-5'-O-[phenyl(cyclohexoxy-L-alaninyl)]phosphate (CPF508)

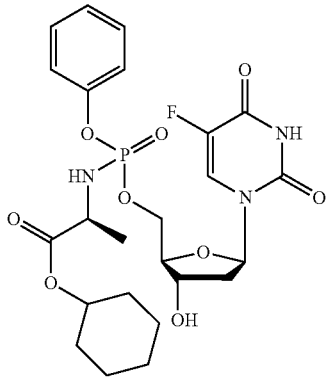

The phosphoramidate was prepared using 5-fluoro-2'-deoxyuridine (0.30 g, 1.21 mmol), N-methylimidazole (NMI) (0.48 mL, 6.09 mmol) and 1-naphthyl(cyclohexoxy-$_L$-alaninyl)phosphorochloridate (1.026 g, 3.65 mmol) according to general procedure D. Purification by gradient column chromatography eluting with $CH_2Cl_2$ until $CH_2Cl_2$-MeOH (95:5) afforded the title compound as a colourless solid (6.7 mg, 3%) [$R_f$=0.45 ($CH_2Cl_2$-MeOH, 95:5)]; (Found: MNa$^+$, 565.48. $C_{24}H_{31}N_3O_9$NaPF requires [MNa$^+$], 565.49); $^{31}$P NMR (202 MHz, MeOD): $^{TM}{}_P$ 3.86, 4.15; $^{19}$F NMR (470 MHz, MeOD): $^{TM}{}_F$ −167.68, −167.62; $^1$H NMR (500 MHz, MeOD): $^{TM}{}_H$ 1.26-1.40 (m, 3H, CHCH$_3$), 1.41-1.50 (m, 4H, CH(CH$_2$)$_5$), 1.52-1.61 (m, 1H, CH(CH$_2$)$_5$), 1.70-1.88 (m, 5H, CH(CH$_2$)$_5$), 2.00-2.14 (m, 1H, H-2'), 2.23-2.34 (m, 1H, H-2'), 3.90-3.98 (m, 1H, CHCH$_3$), 4.07-4.14 (m, 1H, H-4'), 4.29-4.39 (m, 2H, CH$_2$OP), 4.40-4.45 (m, 1H, H-3'), 4.72-4.78 (m, 1H, CH(CH$_2$)$_5$), 6.20-6.28 (m, 1H, H-1'), 7.18-7.29 (m, 3H, ArH), 7.34-7.39 (m, 2H, ArH), 7.85 (d, 1H, $^3J_{H-F}$=6.6 Hz, H-6); $^{13}$C NMR (125 MHz, MeOD): $^{TM}{}_C$ 20.3 (d, $^3J_{C-P}$=7.3 Hz, CH$_3$), 20.6 (d, $^3J_{C-P}$=6.5 Hz, CH$_3$), 24.6 (CH$_2$), 26.4 (CH$_2$), 32.3 (CH$_2$), 32.4 (CH$_2$), 40.9 (CH$_2$), 51.7 (CH), 51.9 (CH), 67.5 (d, $^2J_{C-P}$=5.3 Hz, CH$_2$), 67.7 (d, $^2J_{C-P}$=5.3 Hz, CH$_2$), 72.0 (CH), 72.1 (CH), 74.9 (CH), 86.6 (d, $^3J_{C-P}$=8.5 Hz, CH), 86.8 (d, $^3J_{C-P}$=8.5 Hz, CH), 86.9 (CH), 87.0 (CH), 121.3 (CH), 121.4 (CH), 121.5 (CH), 121.6 (CH), 125.6 (CH), 125.7 (CH), 125.8 (CH), 125.9 (CH), 126.3 (CH), 130.1 (CH), 141.5 (d, $^1J_{C-F}$=234.0 Hz, C), 150.7 (d, $^4J_{C-P}$=4.0 Hz, C), 152.0 (d, $^2J_{C-P}$=7.2 Hz, C), 152.1 (d, $^2J_{C-P}$=7.2 Hz, C), 159.4 (d, $^2J_{C-F}$=26.3 Hz, C), 174.3 (d, $^3J_{C-P}$=4.6 Hz, C), 174.5 (d, $^3J_{C-P}$=4.3 Hz, C); m/z (ES) 565 (MNa$^+$, 100%); Reverse-phase HPLC eluting with H$_2$O/MeOH from 100/0 to 0/100 in 45 minutes, 1 ml/min, $\lfloor$=275 nm, showed two peaks of the diastereoisomers with $t_R$ 30.00 min. and $t_R$ 30.45 min. (33%:65%).

5-Fluoro-2'deoxyuridine-5'-O-[p-nitro-phenyl(ethoxy-L-alaninyl)]phosphate (CPF430)

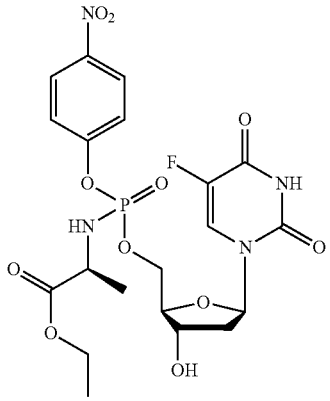

The phosphoramidate was prepared using 5-fluoro-2'-deoxyuridine (0.25 g, 1.01 mmol), N-methylimidazole (NMI) (0.40 mL, 5.07 mmol) and p-nitro-phenyl(ethoxy-L-alaninyl)phosphorochloridate (1.02 g, 3.04 mmol) according to general procedure D. Purification by gradient column chromatography eluting with $CH_2Cl_2$ until $CH_2Cl_2$-MeOH (95:5) afforded the title compound as a colourless solid (77.0 mg, 14%) [$R_f$=0.24 ($CH_2Cl_2$-MeOH, 95:5)], (Found: MNa$^+$, 569.1066. $C_{20}H_{24}N_4O_{11}$NaPF requires [MNa$^+$], 569.1061); $^{31}$P NMR (202 MHz, MeOD): $^{TM}{}_P$ 3.63, 3.67; $^{19}$F NMR (470 MHz, MeOD): $^{TM}{}_F$ −167.89, −167.82; $^1$H NMR (500 MHz, MeOD): $^{TM}{}_H$ 1.24 (t, 3H, J=7.0 Hz, CH$_2$CH$_3$), 1.25 (t, 3H, J=7.0 Hz, CH$_2$CH$_3$), 1.36-1.40 (m, 3H, CHCH$_3$), 2.16-2.25 (m, 1H, H-2'), 2.30-2.38 (m, 1H, H-2'), 3.95-4.00 (m, 1H, CHCH$_3$), 4.09-4.19 (m, 3H, CH$_2$CH$_3$, H-4'), 4.32-4.48 (m, 3H, CH$_2$OP, H-3'), 6.21-6.29 (m, 1H, H-1'), 7.46 (d, 1H, J=8.7 Hz, ArH), 7.49 (d, 1H, J=8.7 Hz, ArH), 7.85 (d, 1H, $^3J_{H-F}$=6.6 Hz, H-6), 7.87 (d, 1H, $^3J_{H-F}$=6.6 Hz, H-6), 8.29 (d, 2H, J=8.7 Hz, ArH); $^{13}$C NMR (125 MHz, MeOD): $^{TM}{}_C$ 14.5 (CH$_3$), 14.6 (CH$_3$), 20.3 (d, $^3J_{C-P}$=7.5 Hz, CH$_3$), 20.4 (d, $^3J_{C-P}$=6.4 Hz, CH$_3$), 40.8 (CH$_2$), 51.6 (CH), 51.7 (CH), 62.5 (CH$_2$), 67.8 (d, $^2J_{C-P}$=5.5 Hz, CH$_2$), 68.0 (d, $^2J_{C-P}$=5.2 Hz, CH$_2$), 71.8 (CH×2), 86.4 (CH), 86.5 (CH), 87.0 (d, $^3J_{C-P}$=7.5 Hz, CH), 122.1 (d, $^3J_{C-P}$=5.2 Hz, CH), 122.5 (d, $^3J_{C-P}$=5.0 Hz, CH), 125.7 (CH), 126.0 (CH), 126.6 (CH), 141.3 (d, $^1J_{C-F}$=233.6 Hz, C), 141.5 (d, $^1J_{C-F}$=233.7 Hz, C), 146.2 (C), 150.6 (d, $^4J_{C-P}$=4.6 Hz, C), 156.9 (d, $^2J_{C-P}$=2.6 Hz, C), 157.0 (d, $^2J_{C-P}$=2.6 Hz, C), 159.3 (d, $^2J_{C-F}$=26.3 Hz, C), 174.6 (d, $^3J_{C-P}$=4.6 Hz, C), 174.9 (d, $^3J_{C-P}$=3.7 Hz, C), m/z (ES) 569 (MNa$^+$, 100%); Reverse-phase HPLC eluting with H$_2$O/MeOH from 100/0 to 0/100 in 45 min., 1 ml/min, $\lfloor$=275 nm, showed two peaks of the diastereoisomers with $t_R$ 31.63 min. and $t_R$ 31.89 min. (11%:85%).

5-Fluoro-2'deoxyuridine-5'-O-[1-naphthyl(benzoxy-L-alaninyl)]phosphate (CPF373)

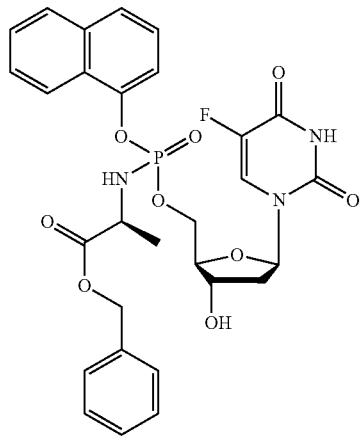

The phosphoramidate was prepared using 5-fluoro-2'-deoxyuridine (0.25 g, 1.01 mmol), N-methylimidazole (NMI) (0.40 mL, 5.07 mmol) and 1-naphthyl(benzoxy-L-alaninyl)phosphorochloridate (0.82 g, 3.04 mmol) according to general procedure D. Purification by gradient column chromatography eluting with $CH_2Cl_2$ until $CH_2Cl_2$-MeOH (95:5) afforded the title compound as a colourless solid (47.0 mg, 8%) [$R_f$=0.19 ($CH_2Cl_2$-MeOH, 95:5)], (Found: MNa$^+$, 636.1520. $C_{29}H_{29}N_3O_9NaPF$ requires [MNa$^+$], 636.1523); $^{31}$P NMR (202 MHz, MeOD): $\mathit{TM}_P$ 4.24, 4.59; $^{19}$F NMR (470 MHz, MeOD): $\mathit{TM}_F$ −167.36, −167.18; $^1$H NMR (500 MHz, MeOD): $\mathit{TM}_H$ 1.34-1.38 (m, 3H, CHCH$_3$), 1.67-1.79 (m, 1H, H-2'), 2.08-2.17 (m, 1H, H-2'), 4.03-4.15 (m, 2H, CHCH$_3$, H-4'), 4.24-4.36 (m, 3H, CH$_2$OP, H-3'), 5.08 (d, 1H, J=12.0 Hz, OCHHPh), 5.13 (d, 1H, J=12.0 Hz, OCHHPh), 6.09-6.16 (m, 1H, H-1'), 7.27-7.45 (m, 6H, ArH), 7.47-7.55 (m, 3H, ArH), 7.67-7.72 (m, 2H, ArH, H-6), 7.86-7.90 (m, 1H, ArH), 8.12-8.18 (m, 1H, ArH); $^{13}$C NMR (125 MHz, MeOD): $\mathit{TM}_C$ 20.3 (d, $^3J_{C-P}$=7.6 Hz, CH$_3$), 20.5 (d, $^3J_{C-P}$=6.5 Hz, CH$_3$), 40.8 (CH$_2$), 40.9 (CH$_2$), 51.8 (CH), 51.9 (CH), 67.6 (d, $^2J_{C-P}$=5.3 Hz, CH$_2$), 67.8 (d, $^2J_{C-P}$=5.2 Hz, CH$_2$), 68.0 (CH$_2$), 68.1 (CH$_2$), 72.0 (CH), 72.1 (CH), 86.7 (d, $^3J_{C-P}$=8.1 Hz, CH), 86.8 (d, $^3J_{C-P}$=8.1 Hz, CH), 86.9 (CH), 87.0 (CH), 116.2 (d, $^3J_{C-P}$=3.3 Hz, CH), 116.5 (d, $^3J_{C-P}$=3.5 Hz, CH), 122.6 (CH), 125.3 (CH), 125.4 (CH), 125.6 (CH), 125.7 (CH), 126.2 (CH), 126.5 (CH), 126.6 (CH), 127.6 (CH), 127.7 (CH), 127.8 (C), 127.9 (C), 128.0 (CH), 128.1 (CH), 128.9 (CH), 129.0 (CH), 129.4 (CH), 129.5 (CH), 129.6 (CH), 129.7 (CH), 136.2 (C), 137.1 (C), 137.2 (C), 141.6 (d, $^1J_{C-F}$=233.8 Hz, C), 141.7 (d, $^1J_{C-F}$=233.9 Hz, C), 147.8 (d, $^2J_{C-P}$=7.7 Hz, C), 147.9 (d, $^2J_{C-P}$=7.4 Hz, C), 150.5 (d, $^4J_{C-F}$=4.0 Hz, C), 159.3 (d, $^2J_{C-F}$=26.1 Hz, C), 174.6 (d, $^3J_{C-P}$=5.0 Hz, C), 174.9 (d, $^3J_{C-P}$=4.3 Hz, C), m/z (ES) 636 (MNa$^+$, 100%); Reverse-phase HPLC eluting with H$_2$O/MeOH from 100/0 to 0/100 in 45 minutes, 1 ml/min, ⌊=275 nm, showed two peaks of the diastereoisomers with $t_R$ 34.23 min. and $t_R$ 34.59 min. (23%:76%).

5-Fluoro-2'deoxyuridine-5'-O-[1-naphthyl(methoxy-L-alaninyl)]phosphate (CPF385)

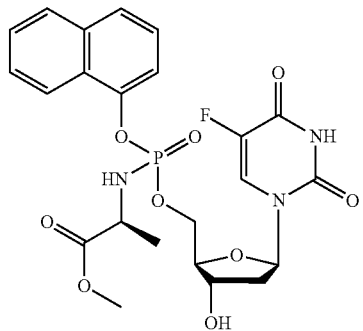

The phosphoramidate was prepared using 5-fluoro-2'-deoxyuridine (0.25 g, 1.01 mmol), N-methylimidazole (NMI) (0.40 mL, 5.07 mmol) and 1-naphthyl(methoxy-L-alaninyl)phosphorochloridate (0.99 g, 3.04 mmol) according to general procedure D. Purification by gradient column chromatography eluting with CH$_2$Cl$_2$ until CH$_2$Cl$_2$-MeOH (95:5) afforded the title compound as a colourless solid (7.0 mg, 1%) [R$_f$=0.23 (CH$_2$Cl$_2$-MeOH, 95:5)], (Found: MNa$^+$, 560.1198. $C_{23}H_{25}N_3O_9NaPF$ requires [MNa$^+$], 560.1210); $^{31}$P NMR (202 MHz, MeOD): $\mathit{TM}_P$ 4.31, 4.56; $^{19}$F NMR (470 MHz, MeOD): $\mathit{TM}_F$ −167.51, −167.37; $^1$H NMR (500 MHz, MeOD): $\mathit{TM}_H$ 1.34 (d, 3H, J=6.7 Hz, CHCH$_3$, one diast.), 1.36 (d, 3H, J=6.7 Hz, CHCH$_3$, one diast.), 1.76-1.87 (m, 1H, H-2'), 2.12-2.22 (m, 1H, H-2'), 3.64 (s, 3H, OCH$_3$, one diast.), 3.65 (s, 3H, OCH$_3$, one diast.), 4.03-4.13 (m, 2H, CHCH$_3$, H-4'), 4.30-4.38 (m, 2H, CH$_2$OP), 4.41 (dd, 1H, J=2.5 Hz, J=5.8 Hz, H-3'), 6.12-6.19 (m, 1H, H-1'), 7.41-7.46 (m, 1H, ArH), 7.50-7.58 (m, 3H, ArH), 7.70-7.76 (m, 2H, H-6, ArH), 7.87-7.91 (m, 1H, ArH), 8.15-8.20 (m, 1H, ArH); $^{13}$C NMR (125 MHz, MeOD): $\mathit{TM}_C$ 20.3 (d, $^3J_{C-P}$=7.1 Hz, CH$_3$), 20.4 (d, $^3J_{C-P}$=6.5 Hz, CH$_3$), 40.7 (CH$_2$), 40.8 (CH$_2$), 51.6 (CH$_3$), 51.7 (CH$_3$), 52.7 (CH), 52.8 (CH), 67.8 (d, $^2J_{C-P}$=5.7 Hz, CH$_2$), 67.5 (d, $^2J_{C-P}$=5.7 Hz, CH$_2$), 72.0 (CH), 72.1 (CH), 86.7 (d, $^3J_{C-P}$=7.9 Hz, CH), 86.9 (d, $^3J_{C-P}$=8.5 Hz, CH), 86.9 (CH), 87.0 (CH), 116.2 (d, $^3J_{C-P}$=3.1 Hz, CH), 116.5 (d, $^3J_{C-P}$=3.5 Hz, CH), 122.5 (CH), 122.6 (CH), 125.4 (CH), 125.5 (CH), 125.6 (CH), 125.7 (CH), 126.1 (CH), 126.2 (CH), 126.5 (CH), 126.6 (CH), 127.6 (CH), 127.7 (C×2), 127.8 (CH), 127.9 (CH), 128.9 (CH), 129.0 (CH), 136.3 (C), 141.6 (d, $^1J_{C-F}$=233.4 Hz, C), 141.7 (d, $^1J_{C-F}$=234.1 Hz, C), 147.8 (d, $^2J_{C-P}$=7.9 Hz, C), 148.0 (d, $^2J_{C-P}$=7.2 Hz, C), 150.6 (C), 159.4 (d, $^2J_{C-F}$=27.0 Hz, C), 175.2 (d, $^3J_{C-P}$=3.9 Hz, C), 175.5 (d, $^3J_{C-P}$=3.9 Hz, C), m/z (ES) 560 (MNa$^+$, 100%); Reverse-phase HPLC eluting with H$_2$O/MeOH from 100/0 to 0/100 in 45 minutes, 1 ml/min, ⌊=275 nm, showed two peaks of the diastereoisomers with $t_R$ 28.45 min. and $t_R$ 28.85 min. (73%:25%).

5-Fluoro-2'deoxyuridine-5'-O-[1-naphthyl(ethoxy-L-alaninyl)]phosphate (CPF386)

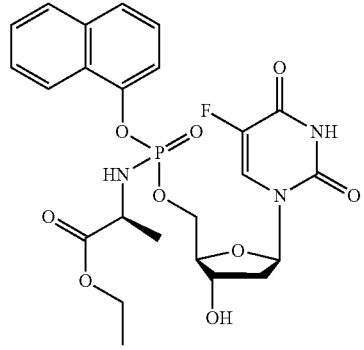

The phosphoramidate was prepared using 5-fluoro-2'-deoxyuridine (0.25 g, 1.01 mmol), N-methylimidazole (NMI) (0.40 mL, 5.07 mmol) and 1-naphthyl(ethoxy-L-alaninyl)phosphorochloridate (1.04 g, 3.04 mmol) according to general procedure D. Purification by gradient column chromatography eluting with CH$_2$Cl$_2$ until CH$_2$Cl$_2$-MeOH (95:5) afforded the title compound as a colourless solid (47.0 mg, 4%) [R$_f$=0.25 (CH$_2$Cl$_2$-MeOH, 95:5)], (Found: MNa$^+$, 574.1360. $C_{24}H_{27}N_3O_9NaPF$ requires [MNa$^+$], 574.1367); $^{31}$P NMR (202 MHz, MeOD): $\mathit{TM}_P$ 4.34, 4.55; $^{19}$F NMR (470 MHz, MeOD): $\mathit{TM}_F$ −167.31, −167.16; $^1$H NMR (500 MHz, MeOD): $\mathit{TM}_H$ 1.20 (t, 3H, J=7.0 Hz, CH$_2$CH$_3$, one diast.), 1.21 (t, 3H, J=7.0 Hz, CH$_2$CH$_3$, one diast.), 1.33-1.37 (m, 3H, CHCH$_3$), 1.73-1.86 (m, 1H, H-2'), 2.12-2.21 (m, 1H, H-2'), 4.01-4.07 (m, 1H, CHCH$_3$), 4.08-4.13 (m, 3H, CH$_2$CH$_3$, H-4'), 4.31-4.43 (m, 3H, CH$_2$OP, H-3'), 6.11-6.19 (m, 1H, H-1'), 7.39-7.46 (m, 1H, ArH), 7.50-7.57 (m, 3H, ArH), 7.68-7.75 (m, 2H, ArH, H-6), 7.86-7.91 (m, 1H, ArH), 8.15-8.20 (m, 1H, ArH); $^{13}$C NMR (125 MHz, MeOD): $\mathit{TM}_C$ 14.4 (CH$_3$), 20.3 (d, $^3J_{C-P}$=7.4 Hz, CH$_3$), 20.5 (d, $^3J_{C-P}$=6.2 Hz, CH$_3$), 40.8 (CH$_2$), 40.9 (CH$_2$), 51.8 (CH), 51.9 (CH), 62.4 (CH$_2$), 62.5 (CH$_2$), 67.8 (d, $^2J_{C-P}$=4.6 Hz, CH$_2$), 67.9 (d, $^2J_{C-P}$=4.6 Hz, CH$_2$), 72.0 (CH), 72.1 (CH), 86.7 (d, $^3J_{C-P}$=8.4 Hz, CH), 86.8 (d, $^3J_{C-P}$=8.4 Hz, CH), 86.9 (CH), 87.0 (CH), 116.1 (d, $^3J_{C-P}$=3.5 Hz, CH), 116.5 (d, $^3J_{C-P}$=3.5 Hz, CH), 122.6 (CH), 125.4 (CH), 125.5 (CH), 125.7 (CH), 125.8 (CH), 126.1 (CH), 126.2 (CH), 126.5 (CH), 126.6 (CH), 127.5 (CH), 127.6 (C), 127.7 (C), 127.8 (CH), 127.9 (CH), 128.9 (CH), 129.0 (CH), 136.3 (C), 141.6 (d, $^1J_{C-F}$=233.3 Hz, C), 141.7 (d, $^1J_{C-F}$=233.4 Hz, C), 147.8 (d, $^2J_{C-P}$=6.9 Hz, C), 148.0 (d, $^2J_{C-P}$=6.9 Hz, C), 150.6 (C), 159.3 (d, $^2J_{C-F}$=26.3 Hz, C), 174.8 (d, $^3J_{C-P}$=4.8 Hz, C), 175.1 (d, $^3J_{C-P}$=4.0 Hz, C); m/z (ES) 574 (MNa$^+$, 100%); Reverse-phase HPLC eluting with H$_2$O/MeOH from 100/0 to 0/100 in 45 minutes, 1 ml/min, ⌊=275 nm, showed two peaks of the diastereoisomers with t$_R$ 30.77 min. and t$_R$ 31.20 min. (51%:48%).

5-Fluoro-2'deoxyuridine-5'-O-[1-naphthyl(isopropoxy-L-alaninyl)]phosphate (CPF387)

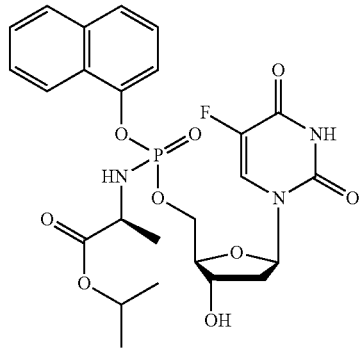

The phosphoramidate was prepared using 5-fluoro-2'-deoxyuridine (0.10 g, 0.40 mmol), tert-butylmagnesium chloride in tetrahydrofuran ($^t$BuMgCl) (1.0 M, 0.61 mL, 0.61 mmol) and 1-naphthyl(isopropoxy-L-alaninyl)phosphorochloridate (0.31 g, 0.89 mmol) according to general procedure E. Purification by gradient column chromatography eluting with CH$_2$Cl$_2$ until CH$_2$Cl$_2$-MeOH (95:5) afforded the title compound as a colourless solid (71.0 mg, 17%) [R$_f$=0.21 (CH$_2$Cl$_2$-MeOH, 95:5)], (Found: MNa$^+$, 588.1521. C$_2$H$_{29}$N$_3$O$_9$NaPF requires [MNa$^+$], 588.1523); $^{31}$P NMR (202 MHz, MeOD): $^{TM}_P$ 4.38, 4.58; $^{19}$F NMR (470 MHz, MeOD): $^{TM}_F$ −167.43, −167.26; $^1$H NMR (500 MHz, MeOD): $^{TM}_H$ 1.19-1.23 (m, 6H, CH(CH$_3$)$_2$), 1.34-1.38 (m, 3H, CHCH$_3$), 1.68-1.84 (m, 1H, H-2'), 2.09-2.20 (m, 1H, H-2'), 3.96-4.05 (m, 1H, CHCH$_3$), 4.07-4.12 (m, 1H, H-4'), 4.29-4.38 (m, 2H, CH$_2$OP), 4.39-4.42 (m, 1H, H-3'), 4.93-5.01 (m, 1H, CH(CH$_3$)$_2$), 5.10-6.18 (m, 1H, H-1'), 7.40-7.46 (m, 1H, ArH), 7.50-7.57 (m, 3H, ArH), 7.70-7.75 (m, 2H, H-6, ArH), 7.87-7.92 (m, 1H, ArH), 8.16-8.20 (m, 1H, ArH); $^{13}$C NMR (125 MHz, MeOD): $^{TM}_C$ 20.3 (d, $^3J_{C-P}$=7.1 Hz, CH$_3$), 20.5 (d, $^3J_{C-P}$=6.6 Hz, CH$_3$), 21.8 (CH$_3$), 21.9 (CH$_3$), 22.0 (CH$_3$), 22.1 (CH$_3$), 40.8 (CH$_2$), 40.9 (CH$_2$), 51.9 (CH), 52.0 (CH), 67.8 (d, $^2J_{C-P}$=4.5 Hz, CH$_2$), 67.9 (d, $^2J_{C-P}$=4.8 Hz, CH$_2$), 70.2 (CH), 70.3 (CH), 72.0 (CH), 72.1 (CH), 86.6 (CH), 86.7 (CH), 86.9 (d, $^3J_{C-P}$=8.6 Hz, CH), 87.0 (d, $^3J_{C-P}$=8.6 Hz, CH), 116.2 (d, $^3J_{C-P}$=2.5 Hz, CH), 116.5 (d, $^3J_{C-P}$=2.7 Hz, CH), 122.6 (CH), 125.5 (CH), 125.7 (CH), 126.1 (CH), 126.2 (CH), 126.5 (CH), 127.5 (CH), 127.6 (C), 127.7 (C), 127.8 (CH), 127.9 (CH), 128.9 (CH), 129.0 (CH), 136.3 (C), 141.6 (d, $^1J_{C-F}$=233.2 Hz, C), 141.7 (d, $^1J_{C-F}$=233.4 Hz, C), 147.7 (d, $^2J_{C-P}$=7.6 Hz, C), 147.9 (d, $^2J_{C-P}$=7.7 Hz, C), 150.5 (C), 159.4 (d, $^2J_{C-F}$=26.2 Hz, C), 174.4 (d, $^3J_{C-P}$=5.0 Hz, C), 174.7 (d, $^3J_{C-P}$=5.1 Hz, C); m/z (ES) 588 (MNa$^+$, 100%); Reverse-phase HPLC eluting with H$_2$O/MeOH from 100/0 to 0/100 in 45 minutes, 1 ml/min, ⌊=275 nm, showed two peaks of the diastereoisomers with t$_R$ 32.20 min. and t$_R$ 32.80 min. (27%:69%).

5-Fluoro-2'deoxyuridine-5'-O-[1-naphthyl(cyclohexoxy-L-alaninyl)]phosphate (CPF509)

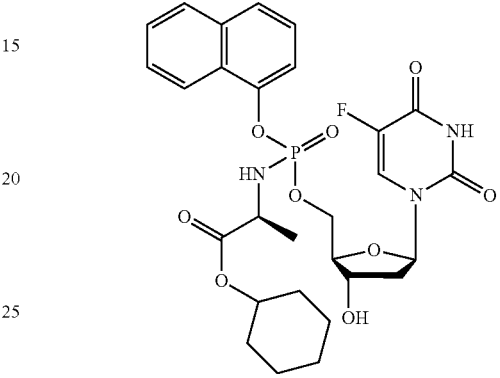

The phosphoramidate was prepared using 5-fluoro-2'-deoxyuridine (0.30 g, 1.21 mmol), N-methylimidazole (NMI) (0.48 mL, 6.09 mmol) and phenyl(cyclohexoxy-L-alaninyl)phosphorochloridate (1.45 g, 3.65 mmol) according to general procedure D. Purification by gradient column chromatography eluting with CH$_2$Cl$_2$ until CH$_2$Cl$_2$-MeOH (95:5) afforded the title compound as a colourless solid (6.7 mg, 3%) [R$_f$=0.47 (CH$_2$Cl$_2$-MeOH, 95:5)]; (Found: MNH$_4^+$, 623.2261. C$_{28}$H$_{37}$N$_4$O$_9$NaPF requires [MNH$_4^+$], 623.2282); $^{31}$P NMR (202 MHz, MeOD): $^{TM}_P$ 4.35, 4.52; $^{19}$F NMR (470 MHz, MeOD): $^{TM}_F$ −167.31, −167.17; $^1$H NMR (500 MHz, MeOD): $^{TM}_H$ 1.30-1.43 (m, 3H, CHCH$_3$), 1.44-1.56 (m, 4H, CH(CH$_2$)$_5$), 1.57-1.66 (m, 1H, CH(CH$_2$)$_5$), 1.67-1.83 (m, 5H, CH(CH$_2$)$_5$), 1.84-1.93 (m, 1H, H-2'), 2.09-2.20 (m, 1H, H-2'), 3.98-4.06 (m, 1H, CHCH$_3$), 4.07-4.15 (m, 1H, H-4'), 4.29-4.38 (m, 2H, CH$_2$OP), 4.39-4.44 (m, 1H, H-3'), 4.67-4.76 (m, 1H, CH(CH$_2$)$_5$), 6.09-6.19 (m, 1H, H-1'), 7.38-7.57 (m, 5H, ArH), 7.68-7.75 (m, 1H, ArH), 7.79-7.92 (m, 1H, ArH), 8.17 (d, 1H, $^3J_{H-F}$=6.6 Hz, H-6); $^{13}$C NMR (125 MHz, MeOD): $^{TM}_C$ 20.4 (d, $^3J_{C-P}$=8.0 Hz, CH$_3$), 20.6 (d, $^3J_{C-P}$=6.5 Hz, CH$_3$), 24.5 (CH$_2$), 26.3 (CH$_2$), 32.3 (CH$_2$), 40.8 (CH$_2$), 51.8 (CH), 51.9 (CH), 67.8 (CH$_2$), 72.0 (CH), 72.2 (CH), 75.0 (CH), 86.7 (d, $^3J_{C-P}$=8.2 Hz, CH), 87.0 (CH), 116.1 (d, $^3J_{C-P}$=2.5 Hz, CH), 116.4 (d, $^3J_{C-P}$=3.0 Hz, CH), 122.6 (CH), 124.8 (CH), 125.9 (CH), 126.1 (CH), 126.2 (CH), 126.4 (CH), 126.5 (CH), 126.6 (CH), 127.6 (CH), 127.7 (C×2), 127.8 (CH), 127.9 (CH), 128.9 (CH), 129.0 (CH), 136.3 (C), 141.6 (C), 148.0 (d, $^2J_{C-P}$=7.2 Hz, C), 150.6 (C), 159.4 (d, $^2J_{C-F}$=27.0 Hz, C), 175.2 (d, $^3J_{C-P}$=3.9 Hz, C), 175.5 (d, $^3J_{C-P}$=3.9 Hz, C); m/z (ES) 623 (MNH$_4^+$, 100%); Reverse-phase HPLC eluting with H$_2$O/MeOH from 100/0 to 0/100 in 45 minutes, 1 ml/min, ⌊=275 nm, showed two peaks of the diastereoisomers with t$_R$ 30.50 min. and t$_R$ 31.48 min. (27%:69%).

5-Fluoro-2'deoxyuridine-5'-O-[phenyl(benzoxy-α,α-dimethylglycine)]phosphate (CPF393)

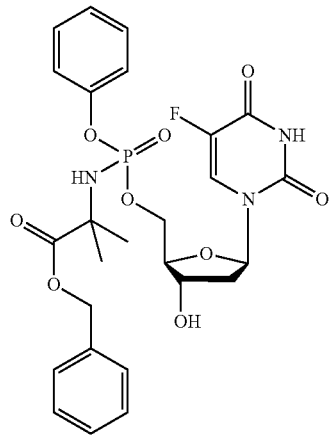

The phosphoramidate was prepared using 5-fluoro-2'-deoxyuridine (0.40 g, 1.62 mmol), tert-butylmagnesium chloride in tetrahydrofuran ($^t$BuMgCl) (1.0 M, 2.43 mL, 2.43 mmol) and phenyl(benzoxy-α,α-dimethylglycine) phosphorochloridate (1.17 g, 3.20 mmol) according to general procedure E. Purification by gradient column chromatography eluting with $CH_2Cl_2$ until $CH_2Cl_2$-MeOH (95:5) afforded the title compound as a colourless solid (69.0 mg, 7%) [$R_f$=0.27 ($CH_2Cl_2$-MeOH, 95:5)], (Found: MNa$^+$, 600.1527. $C_{26}H_{29}N_3O_9$NaPF requires [MNa$^+$], 600.1523); $^{31}$P NMR (202 MHz, MeOD): $^{TM}_P$ 2.42, 2.47; $^{19}$F NMR (470 MHz, MeOD): $^{TM}_F$ −167.80, −167.62; $^1$H NMR (500 MHz, MeOD): $^{TM}_H$ 1.51-1.60 (m, 6H, C(CH$_3$)$_2$), 1.89-1.97 (m, 1H, H-2', one diast.), 2.07-2.15 (m, 1H, H-2', one diast.), 2.21 (ddd, 1H, J=3.4 Hz, 5.9 Hz, 13.5 Hz, H-2', one diast.), 2.29 (ddd, 1H, J=3.2 Hz, 6.1 Hz, 13.5 Hz, H-2', one diast.), 4.00-4.07 (m, 1H, H-4'), 4.22-4.31 (m, 2H, CH$_2$OP), 4.32-4.36 (m, 1H, H-3', one diast.), 4.37-4.41 (m, 1H, H-3', one diast.), 5.08-5.18 (m, 2H, OCH$_2$Ph), 6.19-6.25 (m, 1H, H-1'), 7.20-7.26 (m, 3H, ArH), 7.27-7.39 (m, 7H, ArH), 7.74 (d, $^3J_{H-F}$=6.4 Hz, H-6, one diast.), 7.80 (d, $^3J_{H-F}$=6.4 Hz, H-6, one diast.); $^{13}$C NMR (125 MHz, MeOD): $^{TM}_C$ 27.5 (CH$_3$), 27.7 (d, $^3J_{C-P}$=7.1 Hz, CH$_3$), 27.8 (d, $^3J_{C-P}$=7.1 Hz, CH$_3$), 40.8 (CH$_2$), 40.9 (CH$_2$), 58.2 (C), 58.3 (C), 67.6 (d, $^2J_{C-P}$=5.5 Hz, CH$_2$), 67.7 (d, $^2J_{C-P}$=5.5 Hz, CH$_2$), 68.3 (CH$_2$), 71.9 (CH), 72.0 (CH), 86.6 (d, $^3J_{C-P}$=8.1 Hz, CH), 86.8 (d, $^3J_{C-P}$=7.3 Hz, CH), 86.9 (CH), 121.4 (d, $^3J_{C-P}$=4.8 Hz, CH), 121.6 (d, $^3J_{C-P}$=4.5 Hz, CH), 125.6 (CH), 125.8 (CH), 125.9 (CH), 126.1 (CH), 126.2 (CH), 129.3 (CH), 129.4 (CH), 129.6 (CH), 130.7 (CH), 130.8 (CH), 137.2 (C), 137.3 (C), 141.8 (d, $^1J_{C-F}$=233.7 Hz, C), 150.6 (C), 152.1 (d, $^4J_{C-F}$=7.0 Hz, C), 152.1 (d, $^4J_{C-F}$=7.6 Hz, C), 159.3 (d, $^2J_{C-F}$=26.1 Hz, C), 159.4 (d, $^2J_{C-F}$=26.1 Hz, C), 176.5 (d, $^3J_{C-P}$=4.0 Hz, C), 176.6 (d, $^3J_{C-P}$=3.8 Hz, C), m/z (ES) 600.1 (MNa$^+$, 100%); Reverse-phase HPLC eluting with H$_2$O/MeOH from 100/0 to 0/100 in 35 minutes, 1 ml/min, $\lfloor$=275 nm, showed one peak of the mixture of diastereoisomers with t$_R$ 17.71 (96%).

5-Fluoro-2'deoxyuridine-5'-O-[phenyl(ethoxy-α,α-dimethylglycine)]phosphate (CPF394)

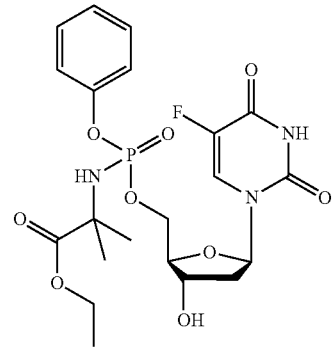

The phosphoramidate was prepared using 5-fluoro-2'-deoxyuridine (0.20 g, 0.80 mmol), N-methylimidazole (NMI) (0.31 mL, 4.0 mmol) and phenyl(ethoxy-α,α-dimethylglycine) phosphorochloridate (0.73 g, 2.40 mmol) according to general procedure D. Purification by gradient column chromatography eluting with $CH_2Cl_2$ until $CH_2Cl_2$-MeOH (95:5) afforded the title compound as a colourless solid (25.0 mg, 6%) [$R_f$=0.24 ($CH_2Cl_2$-MeOH, 95:5)], (Found: MNa$^+$, 538.1367. $C_{21}H_{27}N_3O_9$NaPF requires [MNa$^+$], 538.1367); $^{31}$P NMR (202 MHz, MeOD): $^{TM}_P$ 2.49, 2.52; $^{19}$F NMR (470 MHz, MeOD): $^{TM}_F$ −167.62, −167.58; $^1$H NMR (500 MHz, MeOD): $^{TM}_H$ 1.24 (t, 3H, J=7.1 Hz, CH$_2$CH$_3$, one diast.), 1.26 (t, 3H, J=7.1 Hz, CH$_2$CH$_3$, one diast.), 1.44-1.54 (m, 6H, C(CH$_3$)$_2$), 1.95-2.04 (m, 1H, H-2', one diast.), 2.13-2.21 (m, 1H, H-2', one diast.), 2.24 (ddd, 1H, J=3.1 Hz, J=6.3 Hz, J=13.5 Hz, H-2', one diast.), 2.31 (ddd, 1H, J=3.2 Hz, J=6.1 Hz, J=13.7 Hz, H-2', one diast.), 4.08-4.19 (m, 3H, CH$_2$CH$_3$, H-4'), 4.33-4.49 (m, 3H, CH$_2$OP, H-3'), 6.20-6.30 (m, 1H, H-1'), 7.23-7.28 (m, 3H, ArH), 7.33-7.40 (m, 2H, ArH), 7.80 (d, $^3J_{H-F}$=6.4 Hz, H-6, one diast.), 7.88 (d, $^3J_{H-F}$=6.4 Hz, H-6, one diast.); $^{13}$C NMR (125 MHz, MeOD): $^{TM}_C$ 14.4 (CH$_3$), 14.5 (CH$_3$), 27.5 (d, $^3J_{C-P}$=7.3 Hz, CH$_3$), 27.7 (d, $^3J_{C-P}$=7.6 Hz, CH$_3$), 27.8 (d, $^3J_{C-P}$=7.6 Hz, CH$_3$), 40.8 (CH$_2$), 40.9 (CH$_2$), 58.1 (C), 62.6 (CH$_2$), 62.7 (CH$_2$), 67.6 (d, $^2J_{C-P}$=6.7 Hz, CH$_2$), 67.7 (d, $^2J_{C-P}$=5.8 Hz, CH$_2$), 71.9 (CH), 72.0 (CH), 86.6 (d, $^3J_{C-P}$=8.1 Hz, CH), 86.8 (d, $^3J_{C-P}$=7.6 Hz, CH), 86.9 (CH), 121.4 (d, $^3J_{C-P}$=4.4 Hz, CH), 121.6 (d, $^3J_{C-P}$=4.4 Hz, CH), 125.6 (CH), 125.8 (CH), 125.9 (CH), 126.1 (CH), 126.2 (CH), 130.7 (CH), 130.8 (CH), 130.9 (CH), 141.8 (d, $^1J_{C-F}$=233.5 Hz, C), 150.6 (C), 150.7 (C), 152.2 (d, $^4J_{C-F}$=7.3 Hz, C), 152.3 (d, $^4J_{C-F}$=6.9 Hz, C), 159.2 (d, $^2J_{C-F}$=20.3 Hz, C), 159.4 (d, $^2J_{C-F}$=20.4 Hz, C), 176.6 (d, $^3J_{C-P}$=4.2 Hz, C), 176.8 (d, $^3J_{C-P}$=4.6 Hz, C), m/z (ES) 538.1 (MNa$^+$, 100%); Reverse-phase HPLC eluting with H$_2$O/MeOH from 100/0 to 0/100 in 45 minutes, 1 ml/min, $\lfloor$=275 nm, showed two peaks of the diastereoisomers with t$_R$ 18.76 min. and t$_R$ 20.44 min. (68%:30%).

5-Fluoro-2'deoxyuridine-5'-O-[1-naphthyl(benzoxy-α,α-dimethylglycine)]phosphate (CPF395)

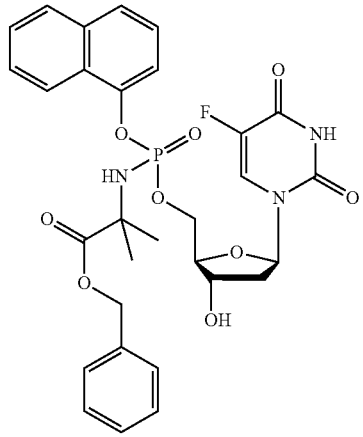

The phosphoramidate was prepared using 5-fluoro-2'-deoxyuridine (0.40 g, 1.62 mmol), N-methylimidazole (NMI) (0.64 mL, 8.0 mmol) and 1-naphthyl(benzoxy-α,α-dimethylglycine) phosphorochloridate (2.00 g, 4.80 mmol) according to general procedure D. Purification by gradient column chromatography eluting with $CH_2Cl_2$ until $CH_2Cl_2$-MeOH (95:5) afforded the title compound as a colourless solid (16.4 mg, 6%) [$R_f$=0.15 ($CH_2Cl_2$-MeOH, 95:5)], (Found: MNa$^+$, 650.1678. $C_{30}H_{31}N_3O_9$NaPF requires [MNa$^+$], 650.1680); $^{31}$P NMR (202 MHz, MeOD): $TM_P$ 2.87, 3.03; $^{19}$F NMR (470 MHz, MeOD): $TM_F$ −167.95, −167.13; $^1$H NMR (500 MHz, MeOD): $TM_H$ 1.37-1.42 (m, 6H, C(CH$_3$)$_2$), 1.61-1.69 (m, 1H, H-2', one diast.), 1.79-1.87 (m, 1H, H-2', one diast.), 2.06 (ddd, 1H, J=3.0 Hz, J=6.1 Hz, J=13.6 Hz, H-2', one diast.), 2.15 (ddd, 1H, J=3.2 Hz, J=5.9 Hz, J=13.7 Hz, H-2', one diast.), 3.98-4.04 (m, 1H, H-4'), 4.19-4.35 (m, 3H, CH$_2$OP, H-3'), 5.09-5.13 (m, 1H, OCHHPh), 5.18-5.19 (m, 1H, OCHHPh), 6.05-6.15 (m, 1H, H-1'), 7.28-7.40 (m, 7H, ArH), 7.48-7.55 (m, 3H, ArH), 7.62 (d, $^3J_{H-F}$=6.4 Hz, H-6, one diast.), 7.70 (d, $^3J_{H-F}$=6.4 Hz, H-6, one diast.), 7.86-7.90 (m, 1H, ArH), 8.17-8.22 (m, 1H, ArH); $^{13}$C NMR (125 MHz, MeOD): $TM_C$ 27.5 (d, $^3J_{C-P}$=4.4 Hz, CH$_3$), 27.9 (d, $^3J_{C-P}$=7.3 Hz, CH$_3$), 28.0 (d, $^3J_{C-P}$=7.3 Hz, CH$_3$), 40.7 (CH$_2$), 40.8 (CH$_2$), 65.2 (C), 67.8 (d, $^2J_{C-P}$=6.5 Hz, CH$_2$), 68.3 (CH$_2$), 72.0 (CH), 72.1 (CH), 86.6 (d, $^3J_{C-P}$=8.2 Hz, CH), 86.8 (d, $^3J_{C-P}$=7.8 Hz, CH), 86.9 (CH), 116.3 (d, $^3J_{C-P}$=3.2 Hz, CH), 116.7 (d, $^3J_{C-P}$=2.9 Hz, CH), 122.8 (CH), 122.9 (CH), 125.4 (CH), 125.5 (CH), 125.6 (CH), 126.0 (CH), 126.1 (CH), 126.4 (CH), 126.5 (CH), 127.4 (CH), 127.5 (CH), 127.7 (CH), 127.8 (CH), 127.9 (C), 128.0 (CH), 128.9 (CH), 129.3 (CH), 129.4 (CH), 129.6 (CH), 136.2 (C), 137.3 (C), 141.8 (d, $^1J_{C-F}$=234.4 Hz, C), 147.9 (d, $^3J_{C-P}$=7.7 Hz, C), 148.0 (d, $^3J_{C-P}$=8.2 Hz, C), 150.7 (d, $^4J_{C-F}$=3.7 Hz, C), 159.5 (d, $^2J_{C-F}$=25.8 Hz, C), 159.6 (d, $^2J_{C-F}$=25.8 Hz, C), 176.5 (C), 176.6 (C), m/z (ES) 650.0 (MNa$^+$, 100%); Reverse-phase HPLC eluting with H$_2$O/MeOH from 100/0 to 0/100 in 45 minutes, 1 ml/min, ⌊=275 nm, showed two peaks of the diastereoisomers with $t_R$ 20.80 min. and $t_R$ 21.00 min. (72%:24%).

5-Fluoro-2'deoxyuridine-5'-O-[1-naphthyl(ethoxy-α,α-dimethylglycine)]phosphate (CPF396)

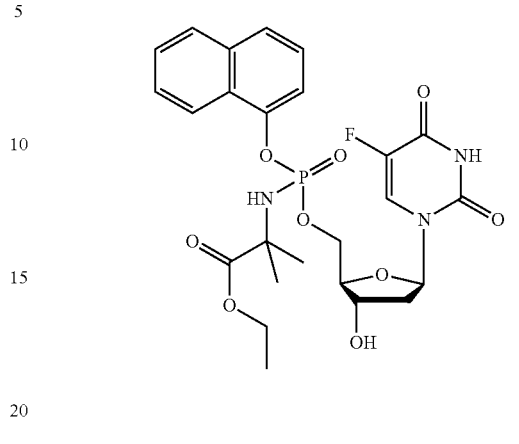

The phosphoramidate was prepared using 5-fluoro-2'-deoxyuridine (0.40 g, 1.62 mmol), tert-butylmagnesium chloride in tetrahydrofuran ($^t$BuMgCl) (1.0 M, 2.43 mL, 2.43 mmol) and 1-naphthyl(ethoxy-α,α-dimethylglycine) phosphorochloridate (1.14 g, 3.20 mmol) according to general procedure E. Purification by gradient column chromatography eluting with $CH_2Cl_2$ until $CH_2Cl_2$-MeOH (95:5) afforded the title compound as a colourless solid (54.0 mg, 2%) [$R_f$=0.10 ($CH_2Cl_2$-MeOH, 95:5)], (Found: MNa$^+$, 588.1528. $C_{25}H_{29}N_3O_9$NaPF requires [MNa$^+$], 588.1523); $^{31}$P NMR (202 MHz, MeOD): $TM_P$ 2.91, 3.03; $^{19}$F NMR (470 MHz, MeOD): $TM_F$ −167.38, −167.21; $^1$H NMR (500 MHz, MeOD): $TM_H$ 1.24 (t, 3H, J=7.1 Hz, CH$_2$CH$_3$, one diast.), 1.25 (t, 3H, J=7.1 Hz, CH$_2$CH$_3$, one diast.), 1.50-1.55 (m, 6H, C(CH$_3$)$_2$), 1.68-1.76 (m, 1H, H-2', one diast.), 1.87-1.94 (m, 1H, H-2', one diast.), 2.09 (ddd, 1H, J=2.9 Hz, J=6.3 Hz, J=13.4 Hz, H-2', one diast.), 2.19 (ddd, 1H, J=3.0 Hz, J=6.3 Hz, J=13.8 Hz, H-2', one diast.), 4.07-4.10 (m, 1H, H-4'), 4.16 (q, 2H, J=7.1 Hz, CH$_2$CH$_3$), 4.36-4.41 (m, 3H, CH$_2$OP, H-3'), 6.10-6.18 (m, 1H, H-1'), 7.40-7.46 (m, 1H, ArH), 7.50-7.59 (m, 3H, ArH), 7.66-7.72 (m, 2H, ArH, H-6), 7.85-7.91 (m, 1H, ArH), 8.18-8.24 (m, 1H, ArH); $^{13}$C NMR (125 MHz, MeOD): $TM_C$ 14.4 (CH$_3$), 27.5 (br s, CH$_3$), 27.9 (d, $^3J_{C-P}$=6.1 Hz, CH$_3$), 28.0 (d, $^3J_{C-P}$=6.1 Hz, CH$_3$), 40.7 (CH$_2$), 40.8 (CH$_2$), 58.2 (C), 58.3 (C), 62.6 (CH$_2$), 67.8 (d, $^2J_{C-P}$=4.9 Hz, CH$_2$), 67.9 (d, $^2J_{C-P}$=4.5 Hz, CH$_2$), 72.0 (CH), 72.1 (CH), 86.7 (d, $^3J_{C-P}$=7.7 Hz, CH), 86.9 (d, $^3J_{C-P}$=7.3 Hz, CH), 87.0 (CH), 116.3 (d, $^3J_{C-P}$=3.2 Hz, CH), 116.6 (d, $^3J_{C-P}$=2.9 Hz, CH), 122.8 (CH), 122.9 (CH), 125.4 (CH), 125.6 (CH), 125.7 (CH), 126.0 (CH), 126.1 (CH), 126.5 (CH), 127.4 (CH), 127.5 (CH), 127.7 (CH), 127.8 (CH), 127.9 (C), 128.0 (C), 128.9 (CH), 136.2 (C), 141.8 (d, 1J$_{C-F}$=233.5 Hz, C), 148.0 (d, $^2J_{C-P}$=7.3 Hz, C), 148.1 (d, $^2J_{C-P}$=7.6 Hz, C), 150.5 (C), 150.6 (C), 159.3 (d, $^2J_{C-F}$=26.2 Hz, C), 159.4 (d, $^2J_{C-F}$=26.6 Hz, C), 176.8 (C), 176.9 (C); m/z (ES) 588.1 (MNa$^+$, 100%); Reverse-phase HPLC eluting with H$_2$O/MeOH from 100/0 to 0/100 in 45 minutes, 1 ml/min, ⌊=275 nm, showed one peak of the mixture of diastereoisomers with $t_R$ 16.05 min. (96%).

5-Fluoro-2'-deoxyuridine-5'-O-[phenyl(benzoxy-L-prolinyl)]phosphate (CPF583)

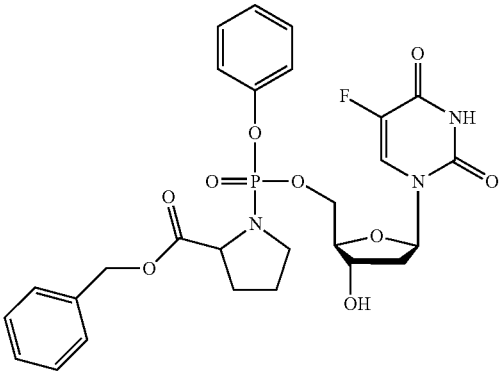

Prepared according to the standard procedure D from 5-Fluoro-2'-deoxyuridine (0.25 g, 1.01 mmol), NMI (0.41 g, 5.07 mmol, 0.40 mL) and phenyl(benzoxy-L-prolinyl)-phosphochloridate (0.77 g, 2.03 mmol) in THF (10 mL). Column purification followed by two preparative TLC purifications gave the product as a white solid (0.010 g, 2%).

$^{31}$P-NMR (MeOD, 202 MHz) δ 1.82

$^{19}$F-NMR (MeOD, 470 MHz) δ −167.91

$^{1}$H-NMR (MeOD, 500 MHz) δ 7.84 (d, J=7.18 Hz, 1H, H-base), 7.39-7.33 (m, 7H, H—Ar), 7.22-7.19 (m, 3H, H—Ar), 6.26-6.23 (m, 1H, H-1'), 5.22-5.13 (m, CH$_2$Ph ester), 4.40-4.35 (m, 3H, NCH, 2×H-5'), 4.33-4.28 (m, 1H, H-3'), 4.06-4.04 (m, 1H, H-4'), 3.36-3.32 (m, 2H, NCH$_2$), 2.26-2.19 (m, 1H, H-2'), 2.18-2.13 (m, 1H, CH$_2$-L-Pro), 2.00-1.81 (m, 4H, 3×H, CH$_2$-L-Pro, 1×H, H-2')

$^{13}$C-NMR (MeOD, 125 MHz) δ 174.81 (C=O, ester), 159.40 (C=O, base), 152.0 (d, $^2J_{C-P}$=6.32 Hz, OC—Ar), 150.71 (C=O, base), 141.88 ($^1J_{C-F}$=232 Hz, CF, base), 137.23 (C—Ar), 131.33, 129.70, 129.48, 129.45, 129.30, 126.45 (CH—Ar), 125.80, 125.53 (2×d, $^2J_{C-F}$=29.0 Hz, CH-base), 121.00, 120.96 (CH—Ar), 87.80 (C-1'), 86.80 (C-4'), 72.02 (C-3'), 68.16 (CH$_2$Ph), 67.64 (d, $^2J_{C-P}$=4.65 Hz, C-5'), 62.40 (d, $^2J_{C-P}$=5.60 Hz, NCH), 48.03 (d, $^2J_{C-P}$=4.80 Hz, NCH$_2$), 41.07 (C-2'), 32.18, 32.11 (CH$_2$-L-Pro), 26.29, 26.21 (CH$_2$-L-Pro).

MS (ES+) m/e: 612 (MNa$^+$, 100%), 590 (MH+, 1%) Accurate mass: C$_{27}$H$_{29}$FN$_3$O$_9$P required 589.51

5-Fluoro-2'-deoxyuridine-5'-O-[1-naphthyl(benzoxy-L-prolinyl)]phosphate (CPF577)

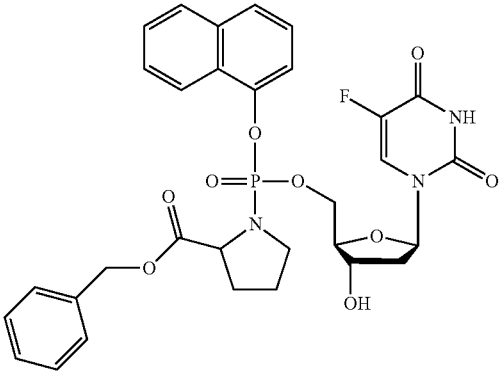

Prepared according to the standard procedure D from 5-Fluoro-2'-deoxyuridine (0.25 g, 1.01 mmol), NMI (0.41 g, 5.07 mmol, 0.40 mL) and 1-naphthyl(benzoxy-L-prolinyl)-phosphochloridate (0.84 g, 2.03 mmol) in THF (10 mL). Column purification followed by two preparative TLC purifications gave the product as a white solid (0.006 g, 1%).

$^{31}$P-NMR (MeOD, 202 MHz) δ 2.27

$^{19}$F-NMR (MeOD, 121 MHz) δ −167.46

$^{1}$H-NMR (MeOD, 500 MHz) δ 8.14-8.12 (m, 1H, H—Ar), 7.90-7.89 (m, 1H, H—Ar), 7.74-7.71 (m, 2H, 1×H—Ar, 1×H-base), 7.56-7.42 (m, 4H, H—Ar), 7.36-7.33 (m, 5H, H—Ar), 6.13 (t, J=6.38 Hz, H-1'), 5.22-5.13 (m, 2H, CH$_2$Ph), 4.49-4.46 (m, 1H, NCH), 4.42-4.33 (m, 2H, H-5'), 4.25-4.23 (m, 1H, H-3'), 4.06-4.04 (m, 1H, H-4'), 3.36-3.34 (m, 2H, NCH$_2$), 2.23-2.15 (m, 1H, CH$_2$-L-Pro), 2.10-2.02 (m, 2H, 1×H, CH$_2$-L-Pro, 1×H, H-2'), 1.97-1.77 (m, 2H, CH$_2$-L-Pro), 1.63-1.57 (m, 1H, H-2') $^{13}$C-NMR (MeOD, 125 MHz) δ 174.82 (C=O, ester), 159.52 (C=O, base), 150.54 (C=O, base), 147.84, 147.78 (d, $^2J_{C-P}$=6.03 Hz, OC—Ar), 141.75, 139.97 (2×d, $^1J_{C-F}$=232 Hz, CF, base), 137.20, 136.34 (C—Ar), 129.76, 129.65, 129.44, 129.36, 129.27, 129.06, 128.95, 128.04, 128.75, 126.56 (CH—Ar), 125.41 (d, $^2J_{C-F}$=30.0 Hz, CH-base), 122.13 (CH—Ar), 115.76 (d, $^3J_{C-P}$=3.3 Hz, CH—Ar), 87.06 (C-1'), 86.79 (C-4'), 72.23 (C-3'), 68.15 (d, $^2J_{C-P}$=5.46 Hz, C-5'), 68.08 (CH$_2$Ph), 62.53 (d, $^2J_{C-P}$=5.60 Hz, NCH), 48.26 (d, $^2J_{C-P}$=5.34 Hz, NCH$_2$), 40.97 (C-2'), 32.16, 32.09 (CH$_2$-L-Pro), 26.22, 26.15 (CH$_2$-L-Pro).

5-Fluoro-2'-deoxyuridine-5'-O-[1-naphthyl(3,3-dimethyl-1-butoxy-L-alaninyl)]phosphate (CPF585)

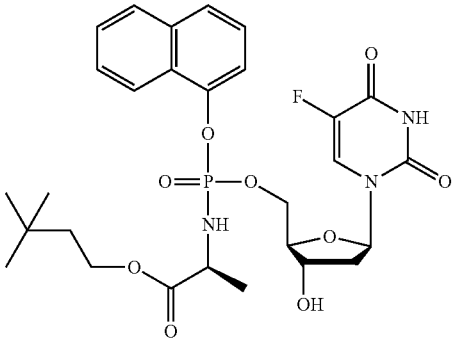

Prepared according to the standard procedure D from 5-Fluoro-2'-deoxyuridine (0.25 g, 1.01 mmol), NMI (0.41 g, 5.07 mmol, 0.40 mL) and 1-naphthyl-(3,3-dimethyl-1-butoxy-L-alaninyl)-phosphochloridate (1.21 g, 3.04 mmol) in THF (10 mL). Column purification followed by two preparative TLC purifications gave the product as a white solid (0.010 g, 2%).

$^{31}$P-NMR (MeOD, 202 MHz) δ 4.48, 4.33

$^{19}$F-NMR (MeOD, 470 MHz) δ −167.30, −167.47

$^{1}$H-NMR (MeOD, 500 MHz) δ 8.20-8.17 (m, 1H, H—Ar), 7.91-7.89 (m, 1H, H—Ar), 7.77-7.72 (m, 2H, H—Ar), 7.58-7.51 (m, 3H, H-base, 2×H—Ar), 7.46-7.41 (2×t, 1H, J=7.8 Hz, H—Ar), 6.19-6.13 (m, 1H, H-1'), 4.42-4.40 (m, 1H, 1×H-5'), 4.38-4.32 (m, 2H, H-3', 1×H-5'), 4.14-4.00 (m, 4H, H-4', CHCH$_3$, OCH$_2$CH$_2$(CH$_3$)$_3$), 2.21-2.13 (m, 1H, 1×H-2'), 1.91-1.76 (m, 1H, 1×H-2'), 1.52-1.48 (m, 2H, OCH$_2$CH$_2$(CH$_3$)$_3$), 1.37-1.35 (m, 3H, CHCH$_3$), 0.92, 0.91 (2×s, 9H, OCH$_2$CH$_2$(CH$_3$)$_3$) $^{13}$C-NMR (MeOD, 125 MHz) δ 175.16, 174.84 (2×d, $^3J_{C-P}$=4.75 Hz, C=O, ester), 159.56, 159.35 (C=O, ester), 150.61 (C=O, ester), 148.00, 147.86 (2×d, $^2J_{C-P}$=6.25 Hz, OC—Ar), 141.78, 141.73 (2×d, $^1J_{C-F}$=232

Hz, CF, base), 136.28 (C—Ar), 128.98, 128.95, 127.92, 127.90, 127.58, 126.57, 126.20, 126.14 (CH—Ar), 125.63, 125.55 (2×d, $^2J_{C-F}$=34 Hz, CH, base), 122.65, 122.63 (CH—Ar), 116.48, 116.15 (2×d, $^3J_{C-P}$=3.0 Hz, CH—Ar), 87.01, 86.94 (C-1'), 86.73, 86.68 (d, $^3J_{C-P}$=7.75 Hz, C-4'), 72.18, 72.07 (C-3'), 67.87, 67.85 (2×d, $^2J_{C-P}$=5.0 Hz, C-5'), 64.08, 64.05 (OCH$_2$CH$_2$(CH$_3$)$_3$), 51.86 (d, $^3J_{C-P}$=5.5 Hz, CHCH$_3$), 42.74 (OCH$_2$CH$_2$(CH$_3$)$_3$), 40.91, 40.83 (C-2'), 29.96 (OCH$_2$CH$_2$(CH$_3$)$_3$), 20.50, 20.34 (2×d, $^3J_{C-P}$=6.5 Hz, CHCH$_3$).

MS (ES+) m/e: 630 (MNa$^+$, 100%), 608 (MH+, 10%)
Accurate mass: C$_{28}$H$_{35}$FN$_3$O$_9$P required 607.56

5-Fluoro-2'-deoxyuridine-5'-O-[1-naphthyl-(cyclobutoxy-L-alaninyl)]phosphate (CPF578)

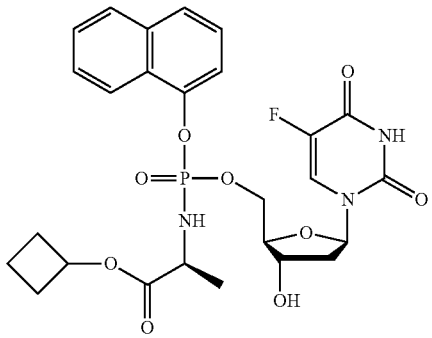

Prepared according to the standard procedure D from 5-Fluoro-2'-deoxyuridine (0.23 g, 0.93 mmol), NMI (0.38 g, 4.67 mmol, 0.37 mL) and 1-naphthyl-(cyclobutoxy-L-alaninyl)-phosphochloridate (0.85 g, 2.33 mmol) in THF (10 mL). Column purification followed by preparative TLC purification gave the product as a white solid (0.010 g, 2%).

$^{31}$P-NMR (MeOD, 202 MHz) δ 4.54, 4.36

$^{19}$F-NMR (MeOD, 470 MHz) δ −167.12, −167.29

$^1$H-NMR (MeOD, 500 MHz) δ 8.18-8.17 (m, 1H, H—Ar), 7.81-7.87 (m, 1H, H—Ar), 7.74-7.71 (m, 2H, 1×H—Ar, 1×H-base), 7.60-7.53 (m, 3H, H—Ar), 7.46-7.43 (2×t, J=8.0 Hz, 1H, H—Ar), 6.18-6.12 (m, 1H, H-1'), 5.00-4.95 (m, 1H, OCH ester), 4.41-4.36 (m, 3H, 2×H-5', H-3'), 4.11-4.00 (m, 2H, H-4', CHCH$_3$), 2.36-2.27 (m, 2H, CH$_2$), 2.18-1.98 (m, 3H, CH$_2$ ester, 1×H-2'), 1.82-1.56 (m, 3H, CH$_2$ ester, 1×H-2'), 1.36-1.34 (m, 3H, CHCH$_3$)

$^{13}$C-NMR (MeOD, 125 MHz) δ 175.97, 173.34 (C=O, ester), 159.88 (C=O, base), 151.64 (C=O, base), 146.58 (OC—Ar), 141.15 (d, J$_{C-F}$=220 Hz, CF, base), 136.28 (C—Ar), 128.93, 127.89, 127.54, 126.52, 126.18, 126.14 (CH—Ar), 125.53, 125.44 (2×d, $^2J_{C-F}$=32.5 Hz, CH-base), 122.63 (CH—Ar), 116.46, 116.44 (2×d, $^3J_{C-P}$=2.5 Hz, CH—Ar), 86.98 (d, $^3J_{C-P}$=6.25 Hz, C-4'), 86.71 (C-1'), 72.14, 72.04 (C-3'), 71.07 (OCH ester), 67.83 (d, $^2J_{C-P}$=7.38 Hz, C-5'), 51.66 (d, $^2J_{C-P}$=8.75 Hz, CHCH$_3$), 40.89, 40.83 (C-2'), 31.03 (OCHCH$_2$), 20.43 (CHCH$_3$), 14.23 (CH$_2$ ester).

MS (ES+) m/e: 600 (MNa$^+$, 100%), 578 (MH+, 10%)
Accurate mass: C$_{26}$H$_{29}$FN$_3$O$_9$P required 577.50

5-Fluoro-2'-deoxyuridine-5'-O-[1-naphthyl-(cyclopropylmethanoxy-L-alaninyl)]phosphate (CPF579)

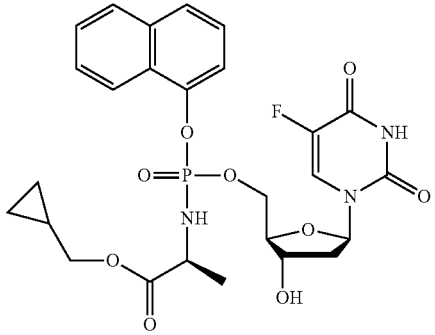

Prepared according to the standard procedure D from 5-Fluoro-2'-deoxyuridine (0.25 g, 1.01 mmol), NMI (0.41 g, 5.07 mmol, 0.40 mL) and 1-naphthyl-(cyclopropylmethanoxy-L-alaninyl)-phosphochloridate (0.93 g, 2.54 mmol) in THF (10 mL). Column purification gave the product as a white solid (0.056 g, 10%).

$^{31}$P-NMR (MeOD, 202 MHz) δ 4.58, 4.30

$^{19}$F-NMR (MeOD, 470 MHz) δ −167.18, −167.22

$^1$H-NMR (MeOD, 500 MHz) δ 8.18 (d, J=7.0 Hz, 1H, H—Ar), 7.89-7.87 (m, 1H, H—Ar), 7.73-7.70 (m, 2H, H—Ar), 7.58-7.53 (m, 3H, H—Ar), 7.45-7.40 (2×t, J=8.0 Hz, 1H, H—Ar), 6.17-6.11 (m, 1H, H-1'), 4.43-4.41 (m, 1H, H-5'), 4.38-4.32 (m, 2H, H-5', H-3'), 4.11-4.04 (m, 2H, H-4', CHCH$_3$), 3.95-3.85 (m, 2H, OCH$_2$ ester), 2.19-2.11 (m, 1H, H-2'), 1.84-1.72 (m, 1H, H-2'), 1.38, 1.36 (2×d, J=5.0 Hz, 3H, CHCH$_3$), 1.15-1.07 (m, 1H, OCH$_2$CH ester), 0.59-0.50 (m, 2H, CH$_2$ ester), 0.30-0.24 (m, 2H, CH$_2$ ester)

$^{13}$C-NMR (MeOD, 125 MHz) δ 175.25, 174.94 (2×d, $^3J_{C-P}$=4.75 Hz, C=O, ester), 159.54, 159.35 (C=O, base), 150.60, 150.56 (C=O, base), 148.05, 147.86 (2×d, $^2J_{C-P}$=7.5 Hz, OC—Ar), 141.79, 141.73 (2×d, $^1J_{C-F}$=232 Hz, CF, base), 136.29 (C—Ar), 128.94 (d, $^3J_{C-P}$=4.4 Hz, CH—Ar), 127.89 (d, $^4J_{C-P}$=3.7 Hz, CH—Ar), 127.56, 126.55, 126.52, 126.19, 126.16 (CH—Ar), 125.64, 125.53 ($^2J_{C-F}$=34 Hz, CH-base), 122.65 (CH—Ar), 116.54, 116.24 (2×d, $^4J_{C-P}$=2.6 Hz, CH—Ar), 87.04, 86.99 (C-1'), 86.90, 86.73 (2×d, $^3J_{C-P}$=7.1 Hz, C-4'), 72.18, 72.07 (C-3'), 71.21, 71.18 (OCH$_2$, ester), 67.87, 67.84 (apparent t, $^2J_{C-P}$=5.0 Hz, C-5'), 51.88 (d, $^2J_{C-P}$=10.0 Hz, CHCH$_3$), 40.91, 40.83 (C-2'), 20.60, 20.46 (2×d, $^3J_{C-P}$=6.5 Hz, CHCH$_3$), 10.69 (OCH$_2$CH ester), 3.70, 3.65 (2×CH$_2$, ester).

MS (ES+) m/e: 600 (MNa$^+$, 100%), 578 (MH+, 15%)
Accurate mass: C$_{26}$H$_{29}$FN$_3$O$_9$P required 577.50

HPLC$_b$ (H$_2$O/Acetonitrile from 100/0 to 0/100 in 35 min) Rt 12.91 min.

5-Fluoro-2'-deoxyuridine-5'-O-[1-naphthyl-(tetrahydropyroxy-L-alaninyl)]phosphate (CPF580)

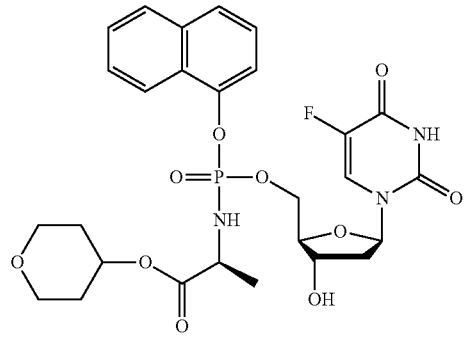

Prepared according to the standard procedure E from 5-Fluoro-2'-deoxyuridine (0.25 g, 1.01 mmol), tBuMgCl (1.1 mL, 1.1 mmol) and 1-naphthyl-(tetrahydropyroxy-L-alaninyl)-phosphochloridate (0.80 g, 2.03 mmol) in THF (10 mL). Column purification followed by two preparative TLC purifications gave the product as a white solid (0.010 g, 1.6%).

$^{31}$P-NMR (MeOD, 202 MHz) δ 3.77, 3.22

$^{19}$F-NMR (MeOD, 470 MHz) δ −168.27, −168.35

$^1$H-NMR (MeOD, 500 MHz) δ 8.60 (d, J=7.0 Hz, 2H, H—Ar), 8.22-8.19 (m, 1H, H—Ar), 7.92-7.91 (d, J=5.50 Hz, 1H, H—Ar), 7.60-7.45 (m, 4H, H—Ar, H-base), 6.29-6.25 (m, 1H, H-1'), 5.25-5.17 (m, 1H, H-3'), 4.96-4.87 (m, 1H, CH-ester), 4.28-4.26 (m, 1H, H-4'), 4.11-4.03 (m, 1H, CHCH$_3$), 3.88-3.66 (m, 4H, 2×OCH$_{2a}$, ester, 2×H-5'), 3.55-3.50 (m, 2H, 2×OCH$_{2a''}$ ester), 2.63-2.30 (m, 2H, H-2'), 1.91-1.85 (m, 2H, 2×CH$_{2b'}$ ester), 1.65-1.54 (m, 2H, CH$_{2b''}$ ester), 1.39-1.35 (m, 3H, CHCH$_3$).

$^{13}$C-NMR (MeOD, 125 MHz) δ 174.34 (C=O, ester), 159.24 (C=O, base), 150.76 (C=O, base), 148.03 (OC—Ar), 141.97 (d, $^1J_{C-F}$=238 Hz, CF, base), 136.37 (C—Ar), 128.97, 128.56, 127.61, 127.57, 126.58, 126.23, 126.16, 126.12, 125.84 (CH—Ar), 122.70 (d, $^2J_{C-F}$=24.0 Hz, CH-base), 116.62, 116.37 (CH—Ar), 87.54 (d, $^3J_{C-P}$=5.40 Hz, C-4'), 86.60, 86.57 (C-1'), 79.82, 79.47 (C-3'), 71.45 (CH-ester), 66.12, 66.08 (2×OCH$_{2a}$ ester), 66.02 (C-5'), 51.83 (CHCH$_3$), 39.97, 39.94 (C-2'), 32.65, 32.57 (2×CH$_{2b}$ ester), 20.45, 20.30 (CHCH$_3$).

MS (ES+) m/e: 630 (MNa$^+$, 100%), 608 (MH+, 10%) Accurate mass: $C_{27}H_{31}FN_3O_{10}P$ required 607.52.

5-Fluoro-2'-deoxyuridine-5'-O-[1-naphthyl-(pentoxy-L-alaninyl)]phosphate (CPF581)

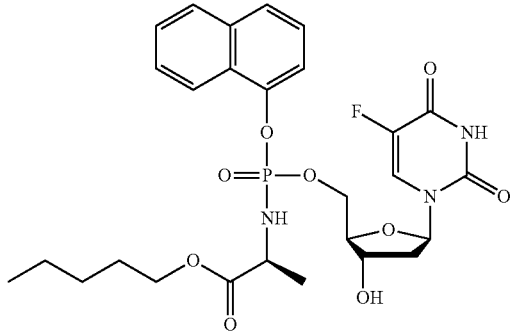

Prepared according to the standard procedure E from 5-Fluoro-2'-deoxyuridine (0.25 g, 1.01 mmol), tBuMgCl (1.1 mL, 1.1 mmol) and 1-naphthyl-(pentoxy-L-alaninyl)-phosphochloridate (0.78 g, 2.03 mmol) in THF (10 mL). Column purification gave the product as a white solid (0.047 g, 8%).

$^{31}$P-NMR (MeOD, 202 MHz) δ 4.48, 4.32

$^{19}$F-NMR (MeOD, 470 MHz) δ −167.18, −167.29

$^1$H-NMR (MeOD, 500 MHz) δ 8.25-8.17 (m, 1H, H—Ar), 8.05-7.95 (m, 2H, H—Ar), 7.85-7.60 (m, 2H, H—Ar, H-base), 7.65-7.48 (m, 3H, H—Ar), 6.30-6.18 (m, 1H, H-1'), 4.60-4.37 (m, 3H, 2×H-5', H-3'), 4.28-4.00 (m, 4H, H-4', CHCH$_3$, OCH$_2$CH$_2$CH$_2$CH$_2$CH$_3$), 2.32-2.12 (m, 1H, H-2'), 1.95-1.75 (m, 1H, H-2'), 1.70-1.55 (m, 2H, OCH$_2$CH$_2$CH$_2$CH$_2$CH$_3$), 1.50-1.28 (m, 7H, 4×H OCH$_2$CH$_2$CH$_2$CH$_2$CH$_3$, CHCH$_3$), 0.83, 0.82 (2×d, J=7.9 Hz, 3H, OCH$_2$CH$_2$CH$_2$CH$_2$CH$_3$)

$^{13}$C-NMR (MeOD, 125 MHz) δ 175.22, 174.91 (C=O, ester), 159.5 (C=O, base), 150.54 (C=O, base), 147.90, 147.88 (OC—Ar), 141.75 (d, $^1J_{C-F}$=225 Hz, CF, base), 136.37 (C—Ar), 128.95, 127.90, 127.56, 126.55, 126.19 (CH—Ar), 125.64, 125.53 (2×d, $^2J_{C-F}$=34.0 Hz, CH-base), 122.65 (CH—Ar), 116.51, 116.21 (CH—Ar), 87.03, 86.96 (C-1'), 86.85, 86.74 (C-4'), 72.16, 72.05 (C-3'), 67.87 (d, $^2J_{C-P}$=5.0 Hz, C-5'), 66.54 (OCH$_2$), 51.87, 51.81 (d, $^2J_{C-P}$=7.5 Hz, CHCH$_3$), 40.87, 40.80 (C-2'), 29.35, 29.10 (CH$_2$ ester), 23.33 (CH$_2$ ester), 20.60, 20.43 (2×d, $^3J_{C-P}$=6.5 Hz, CHCH$_3$), 14.28 (CH$_3$, ester).

MS (ES+) m/e: 616 (MNa$^+$, 100%), 594 (MH+, 10%) Accurate mass: $C_{27}H_{33}FN_3O_9P$ required 593.54.

HPLC$_b$ (H$_2$O/Acetonitrile from 100/0 to 0/100 in 35 min) Rt 15.56 min.

5-Fluoro-2'-deoxyuridine-5'-O-[1-naphthyl-(cyclopentoxy-L-alaninyl)]phosphate (CPF582)

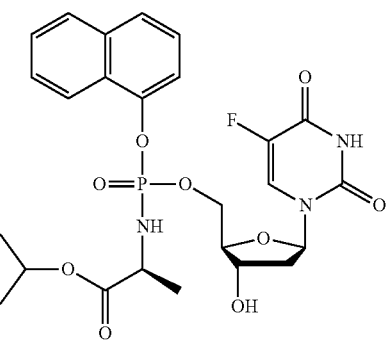

Prepared according to the standard procedure E from 5-Fluoro-2'-deoxyuridine (0.25 g, 1.01 mmol), tBuMgCl (1.1 mL, 1.1 mmol) and 1-naphthyl-(cyclopentoxy-L-alaninyl)-phosphochloridate (0.77 g, 2.03 mmol) in THF (10 mL). Column purification gave the product as a white solid (0.030 g, 5%).

$^{31}$P-NMR (MeOD, 202 MHz) δ 4.53, 4.37

$^{19}$F-NMR (MeOD, 470 MHz) δ −167.07, −167.19

$^1$H-NMR (MeOD, 500 MHz) δ 8.18-8.16 (m, 1H, H—Ar), 7.89-7.85 (m, 1H, H—Ar), 7.70 (apparent t, J=6.50 Hz, 2H, H—Ar), 7.57-7.50 (m, 3H, 2×H—Ar, H-base), 7.45-7.40 (m, 1H, H—Ar), 6.16-6.11 (m, 1H, H-1'), 5.15-5.09 (m, 1H, OCH ester), 4.41-4.30 (m, 3H, 2×H-5', H-3'), 4.11-4.08 (m, 1H, H-4'), 4.04-3.98 (m, 1H, CHCH$_3$), 2.19-2.10 (m, 1H, H-2'), 1.86-1.73 (m, 3H, OCHCH$_2$ ester), 1.73-1.56 (m, 6H, H-2', CH$_2$ ester), 1.35, 1.34 (2×d, J=6.57 Hz, CHCH$_3$)

$^{13}$C-NMR (MeOD, 125 MHz) δ 174.68, 174.64 (C=O, ester), 159.27 (C=O, base), 150.51 (C=O, base), 147.86 (d, $^2J_{C-P}$=7.5 Hz, OC—Ar), 141.78, 141.72 (2×d, $^1J_{C-F}$=232 Hz, CF-base), 136.30 (C—Ar), 128.95, 128.54, 127.94, 127.80, 127.60, 127.56, 127.17, 126.80, 126.54, 126.19, 126.16 (CH—Ar), 125.66, 125.53 (2×d, $^2J_{C-F}$=34 Hz, CH-base), 122.65, 122.61 (CH—Ar), 116.53, 116.22 (2×d, $^4J_{C-P}$=3.75 Hz, CH—Ar), 86.99, 86.96 (C-1'), 86.70 (d, $^3J_{C-P}$=7.50 Hz, C-4'), 79.64, 79.61 (OCH ester), 72.21, 72.07 (C-3'), 67.89, 67.85 (2×d, $^2J_{C-P}$=5.0 Hz, C-5'), 51.92 (d, $^2J_{C-P}$=5.0 Hz, CHCH$_3$), 40.92, 40.86 (C-2'), 33.65, 33.61, 33.52, 33.47 (2×CH$_2$ ester), 24.68, 24.66 (CH$_2$ ester), 20.45, 20.30 (2×d, $^3J_{C-P}$=6.25 Hz, CHCH$_3$).

MS (ES+) m/e: 614 (MNa$^+$, 100%), 592 (MH+, 30%) Accurate mass: $C_{27}H_{31}FN_3O_9P$ required 591.52

HPLC$_b$ (H$_2$O/Acetonitrile from 100/0 to 0/100 in 35 min) Rt 14.03 min.

5-Fluoro-2'-deoxyuridine-5'-O-[1-naphthyl-(2-indanoxy-L-alaninyl)]phosphate (CPF597)

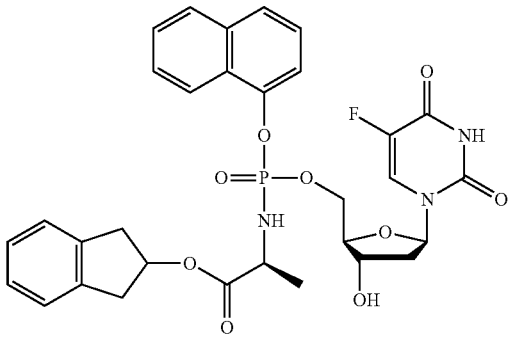

Prepared according to the standard procedure E from 5-Fluoro-2'-deoxyuridine (0.30 g, 1.22 mmol), tBuMgCl (1.34 mL, 1.34 mmol) and 1-naphthyl-(2-indanoxy-L-alaninyl)-phosphochloridate (1.06 g, 2.43 mmol) in THF (mL). Column purification gave the product as a white solid (0.045 g, 6%).

$^{31}$P-NMR (MeOD, 202 MHz) δ 4.62, 4.30

$^{19}$F-NMR (MeOD, 470 MHz) δ −167.14, −167.34

$^{1}$H-NMR (MeOD, 500 MHz) δ 8.15-8.12 (m, 1H, H—Ar, Naph), 7.89-7.87 (m, 1H, H—Ar, Naph), 7.72-7.67 (m, 2H, H—Ar, Naph), 7.56-7.46 (m, 3H, 2×H—Ar, H-base), 7.40-7.37 (m, 1H, H—Ar), 7.20-7.12 (m, 4H, H—Ar, Ph), 6.14-6.08 (m, 1H, H-1'), 5.49-5.46 (m, 1H, OCH ester), 4.32-4.26 (m, 3H, 2×H-5', H-3'), 4.04-3.98 (m, 1H, H-4', CHCH$_3$), 3.30-3.24 (m, 2H, 2×CH ester), 2.99-2.91 (m, 2H, 2×CH ester), 2.14-2.07 (m, 1H, H-2'), 1.75-1.64 (m, 1H, H-2'), 1.33-1.29 (m, 3H, CHCH$_3$)

$^{13}$C-NMR (MeOD, 125 MHz) δ 175.02, 174.66 (2×d, $^{3}J_{C-P}$=3.75 Hz, C=O, ester), 159.48 ($^{2}J_{C-F}$=25.0 Hz, C=O, base), 150.57 (C=O, base), 147.97, 147.80 (2×d, $^{2}J_{C-P}$=7.5 Hz, OC—Ar), 141.73, 141.68 (2×d, $^{1}J_{C-F}$=232.5 Hz, CF-base), 141.54, 141.49, 141.48, 139.10, 136.27, 136.26 (C—Ar), 129.01, 128.94, 128.91, 127.91, 127.87, 128.85, 127.80, 127.77, 127.60, 127.57, 127.50, 126.20, 126.18, 125.69 (CH—Ar), 125.50, 125.43 (2×d, $^{2}J_{C-F}$=25 Hz, CH-base), 122.64, 122.60, 121.85 (CH—Ar), 116.57, 116.26 (2×d, $^{4}J_{C-P}$=2.5 Hz, CH—Ar), 86.96 (C-1'), 86.87, 86.66 (2×d, $^{3}J_{C-P}$=7.50 Hz, C-4'), 77.85, 79. (OCH ester), 72.21, 72.07 (C-3'), 67.77, 67.75 (2×d, $^{2}J_{C-P}$=6.25 Hz, C-5'), 51.97, 51.82 (CHCH$_3$), 40.91, 40.86 (C-2'), 40.44, 40.43, 40.38, 40.34 (2×CH$_2$ ester), 20.30, 20.16 (2×d, $^{3}J_{C-P}$=6.25 Hz, CHCH$_3$)

5-Fluoro-2'-deoxyuridine-5'-O-[phenyl-(benzoxy-L-methioninyl)]phosphate

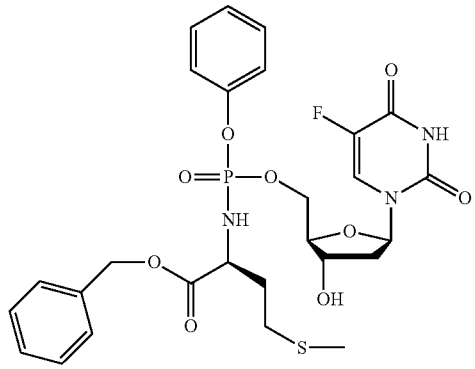

Prepared according to the standard procedure D from 5-Fluoro-2'-deoxyuridine (0.25 g, 1.01 mmol), NMI (0.41 g, 5.07 mmol, 0.40 mL) and phenyl-(benzoxy-L-methioninyl)-phosphochloridate (0.7 g, mmol) in THF (10 mL). Column purification gave the product as a yellowish solid (0.014 g, 2%).

$^{31}$P-NMR (MeOD, 202 MHz) δ 4.34, 3.94

$^{19}$F-NMR (MeOD, 470 MHz) δ −167.40, −167.69

$^{1}$H-NMR (MeOD, 500 MHz) δ 7.83-7.80 (m, 1H, H—Ar), 7.74-7.72 (m, 1H, H—Ar), 7.64-7.62 (m, 1H, H—Ar), 7.37-7.32 (m, 6H, H—Ar, H-base), 7.26-7.17 (m, 2H, H—Ar), 6.25-6.17 (m, 1H, H-1'), 5.18, 5.13 (AB system, $J_{AB}$=12.0 Hz, 2H, CH$_2$Ph), 4.40-4.35 (m, 1H, H-3'), 4.32-4.22 (m, 2H, H-5'), 4.16-4.03 (m, 2H, NHCH, H-4'), 2.44, 2.36 (2×t, J=7.50 Hz, CH$_2$S), 2.16-2.08 (m, 1H, 1×H-2'), 1.98-1.82 (m, 6H, 1×H-2', NHCHCH$_2$CH$_2$SCH$_3$), MS (ES+) m/e: 646 (MNa$^+$, 100%), 624 (MH+, 10%) Accurate mass: C$_{27}$H$_{31}$FN$_3$O$_9$PS required 623.56

5-Fluoro-2'-deoxyuridine-5'-O-[1-naphthyl-(benzoxy-L-phenylalaninyl)]phosphate (CPF587)

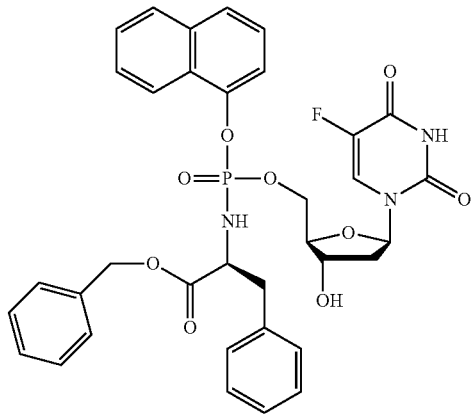

Prepared according to the standard procedure D from 5-Fluoro-2'-deoxyuridine (0.25 g, 1.01 mmol), NMI (0.41 g, 5.07 mmol, 0.40 mL) and 1-naphthyl-(benzoxy-L-phenylalaninyl)-phosphochloridate (1.45 g, mmol) in THF (10 mL). Column purification gave the product as a white solid (0.007 g, 1%).

$^{31}$P-NMR (MeOD, 202 MHz) δ 4.27, 4.14

$^{19}$F-NMR (MeOD, 470 MHz) δ −166.99, −167.18

$^{1}$H-NMR (MeOD, 500 MHz) δ 8.11-8.00 (m, 1H, H—Ar, Ar), 7.89-7.85 (m, 1H, H—Ar), 7.69-7.67 (m, 1H, H—Ar), 7.60-7.49 (m, 3H, 2×H—Ar, H-base), 7.37-7.33 (m, 2H, H—Ar), 7.25-7.12 (m, 10H, H—Ar), 6.09-6.04 (m, 1H, H-1'), 5.11-5.01 (m, 2H, CH$_2$Ph), 4.29-4.18 (m, 1H, CHCH$_3$), 4.15-4.08 (m, 1H, H-3'), 4.02-3.95 (m, 2H, H-5'), 3.86-3.67 (m, 1H, H-4'), 3.14-3.10 (m, 1H, 1×NHCHCH$_2$Ph), 2.91-2.82 (m, 1H, 1×NHCHCH$_2$Ph), 2.12-2.06, 2.00-1.95 (2×m, 1H, H-2'), 1.68-1.62, 1.42-1.36 (2×m, 1H, H-2')

5-Fluoro-2'-deoxyuridine-5'-O-[1-naphthyl-(2,2-dimethylpropoxy-L-alaninyl)]phosphate (CPF588)

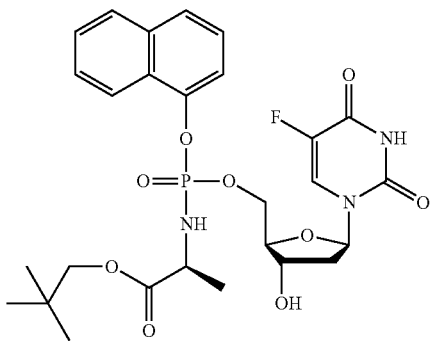

Prepared according to the standard procedure D from 5-Fluoro-2'-deoxyuridine (0.25 g, 1.01 mmol), NMI (0.41 g, 5.07 mmol, 0.40 mL) and 1-naphthyl-(2,2-dimethylpropoxy-L-alaninyl)-phosphochloridate (0.77 g, mmol) in THF (10 mL).

Column purification gave the product as a white solid (0.006 g, 1%).

$^{31}$P-NMR (MeOD, 202 MHz) δ 4.56, 4.33
$^{19}$F-NMR (MeOD, 470 MHz) δ −167.32, −167.43
$^{1}$H-NMR (MeOD, 500 MHz) δ 8.19-8.16 (m, 1H, H—Ar, Ar), 7.91-7.89 (m, 1H, H—Ar), 7.74-7.71 (m, 2H, H—Ar), 7.57-7.51 (m, 3H, 2×H—Ar, H-base), 7.46-7.41 (m, 1H, H—Ar), 6.17-6.10 (m, 1H, H-1'), 4.42-4.30 (m, 3H, H-3', 2×H-5'), 4.13-4.07 (m, 2H, H-4', CHCH$_3$), 3.86, 3.75 (AB system, J$_{AB}$=10.50 Hz, 2H, CH$_2$C(CH$_3$)$_3$), 2.18-2.10 (m, 1H, H-2'), 1.81-1.70 (m, 1H, H-2'), 1.41-1.38 (m, 3H, CHCH$_3$), 0.95, 0.94 (2×s, 9H, CH$_2$C(CH$_3$)$_3$)

5-Fluoro-2'-deoxyuridine-5'-O-[1-naphthyl-(butoxy-L-alaninyl)]phosphate (CPF589)

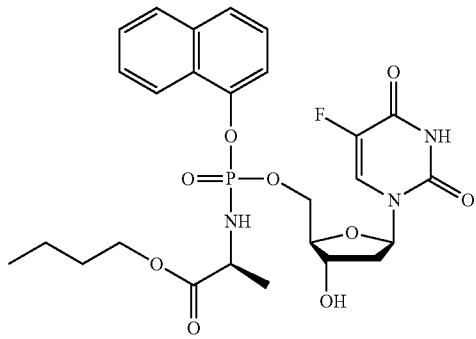

Prepared according to the standard procedure D from 5-Fluoro-2'-deoxyuridine (0.25 g, 1.01 mmol), NMI (0.41 g, 5.07 mmol, 0.40 mL) and 1-naphthyl-(butoxy-L-alaninyl)-phosphochloridate (0.75 g, mmol) in THF (10 mL). Column purification gave the product as a white solid (0.006 g, 1%).

$^{31}$P-NMR (MeOD, 202 MHz) δ 4.52, 4.35
$^{19}$F-NMR (MeOD, 470 MHz) δ −167.36, −167.49
$^{1}$H-NMR (MeOD, 500 MHz) δ 8.19-8.16 (m, 1H, H—Ar, Naph), 7.1-7.89 (m, 1H, H—Ar, Naph), 7.75-7.72 (m, 2H, H—Ar, Naph), 7.58-7.51 (m, 3H, 2×H—Ar, H-base), 7.46-7.41 (m, 1H, H—Ar), 6.18-6.11 (m, 1H, H-1'), 4.42-4.40 (m, 1H, 1×H-5'), 4.37-4.32 (m, 2H, 1×H-5', H-3'), 4.12-4.01 (m, 4H, H-4', CHCH$_3$, OCH$_2$CH$_2$CH$_2$CH$_3$), 2.20-2.12 (m, 1H, H-2'), 1.85-1.73 (m, 1H, H-2'), 1.61-1.54 (m, 2H, OCH$_2$CH$_2$CH$_2$CH$_3$), 1.39-1.31 (m, 5H, OCH$_2$CH$_2$CH$_2$CH$_3$, CHCH$_3$), 0.93-0.89 (m, 3H, OCH$_2$CH$_2$CH$_2$CH$_3$)

Biological Assays

Experimental data having regard to compounds embodying the present invention are described below.

Cell Cultures

Murine leukaemia L1210/0 and human T-lymphocyte CEM/0 cells were obtained from the American Type Culture Collection (ATCC) (Rockville, Md.). Human glioblastoma U87 cells were kindly provided by Dr. E. Menue (Institut Pasteur, Paris, France). Thymidine kinase-deficient CEM/TK$^-$ cells were a kind gift from Prof. S. Eriksson (currently at Uppsala University, Uppsala, Sweden) and Prof. A. Karlsson (Karolinska Institute, Stockholm, Sweden). Thymidine kinase-deficient L1210/TK$^-$ were derived from L1210/0 cells after selection for resistance against 5-bromo-2'-dUrd (Balzarini et al., 1982). Infection of relevant cell lines with *Mycoplasma hyorhinis* (ATCC) resulted in chronically-infected cell lines further referred to as L1210.Hyor and U87.Hyor. All cells were maintained in Dulbecco's modified Eagle's medium (DMEM) (Invitrogen, Carlsbad, Calif.) with 10% foetal bovine serum (FBS) (Biochrom AG, Berlin, Germany), 10 mM Hepes and 1 mM Sodium Pyruvate (Invitrogen). Cells were grown at 37° C. in a humidified incubator with a gas phase of 5% CO$_2$.

Cytostatic Assays

Monolayer cells (U87 and U87.Hyor) were seeded in 48-well microtiter plates (Nunc™, Roskilde, Denmark) at 10,000 cells/well. After 24 hours, an equal volume of fresh medium containing the test compounds was added. On day 5, cells were trypsinized and counted in a Coulter counter (Analis, Suarlée, Belgium). Suspension cells (L1210/0, L1210/TK$^-$, L1210.Hyor, CEM/O, CEM/TK$^-$) were seeded in 96-well microtiter plates (Nunc™) at 60,000 cells/well in the presence of a given amount of the test compounds. The cells were allowed to proliferate for 48 h (L1210) or 72 hours (CEM) and were then counted in a Coulter counter. The 50% inhibitory concentration (IC$_{50}$) was defined as the compound concentration required to reduce the number of viable cells by 50%.

Assay 1.

The samples were assayed for biological activity versus a range of tumour cell lines with data recorded in Table 1 below. Data are expressed as CC$_{50}$ in μM, i.e. cytostatic concentration required to inhibit cell proliferation by 50%. The cell lines employed were L1210/0 (a leukemia cell line), FM3A/0 (a breast cancer cell line), Cem/0 (an acute lymphoblastic leukemia cell line) and HeLa (a cervical cell line).

Table 1 also contains comparative data for 5FU, 5-FdUrd and reference compounds CPF 382, CPF 437 and CPF 438. The structure of CPF 382 is given above. The structure of each of CPF 437 and CPF 438 is as follows:

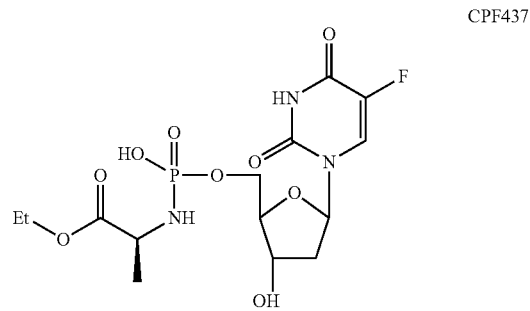

CPF437

CPF438

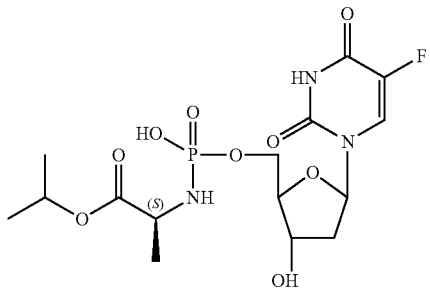

As can be seen from the data in Table 1, compounds of the present invention can exhibit cytostatic activity that is comparable to or better than that of 5-FU, whilst exhibiting marked cytostatic activity in nucleoside kinase-deficient cells. Such a cytostatic activity in nucleotide kinase-deficient cells is in direct contrast to that of 5-FdUrd.

As can also be seen from Table 1, the activity in TK⁻ cells of compounds embodying the present invention can be markedly greater than that of reference compounds CPF 382, CPF 437 and CPF 438.

nucleosides in mycoplasma infected cells provides a potential benefit in patients that are mycoplasma infected.

TABLE 2

CC50 values in μM for 5-FdUrd and compounds embodying the present invention in mycoplasma negative and positive cells, and % retention of activity on mycoplasma infection. "% retention" is a measure of the ratio of the CC50 values measured with respect to L1210 with respect to those for L1210/Hyor and is calculated as $CC50_{L1210} \times 100 \div CC50_{L1210/Hyor}$

| Cpd | L1210 | L1210/Hyor | % Retention |
|---|---|---|---|
| 5-FdUrd | 0.00051 | 0.278 | 0.2 |
| CPF 373 | 0.011 | 0.025 | 44 |
| CPF 381 | 0.026 | 0.15 | 18 |
| CPF 393 | 0.029 | 0.02 | 145 |
| CPF 394 | 0.030 | 0.26 | 12 |
| CPF 395 | 0.019 | 0.045 | 42 |
| CPF 396 | 0.056 | 0.17 | 33 |
| CPF 576 | 1.4 | 2.73 | 51 |
| CPF 577 | 0.23 | 0.63 | 36 |
| CPF 578 | 0.015 | 0.048 | 31 |
| CPF 579 | 0.019 | 0.045 | 42 |
| CPF 580 | 0.048 | 0.41 | 12 |

TABLE 1

| | L1210/0 | L1210/TK⁻ | FM3A/0 | FM3A/TK⁻ | Cem/0 | Cem/TK⁻ | HeLa | HeLa/TK⁻ |
|---|---|---|---|---|---|---|---|---|
| 5-FdUrd | 0.00082 ± 0.00008 | 3.1 ± 0.2 | | | 0.028 ± 0.002 | 1.5 ± 0.1 | | |
| 5-FdUrd (2) | 0.0010 ± 0.0001 | 4.8 ± 4.0 | 0.0065 ± 0.0055 | 0.70 ± 0.02 | 0.026 ± 0.000 | 4.4 ± 2.9 | 0.029 ± 0.007 | 1.4 ± 0.5 |
| 5-FdUrd (3) | 0.0011 ± 0.0002 | 3.0 ± 0.1 | | | 0.022 ± 0.006 | 3.0 ± 0.4 | 0.050 ± 0.011 | 1.4 ± 0.4 |
| FU | 0.33 ± 0.17 | 0.32 ± 0.31 | 0.18 ± 0.02 | | 18 ± 5 | | 0.54 ± 0.12 | |
| CPF 382(1) | 0.0255 | 37.8 | | | 0.346 | 32.7 | | |
| CPF 382(2) | 0.0271 | 39.3 | | | 0.21 | 29.2 | | |
| CPF 437 | 36 ± 5 | >100 | | | >100 | >100 | >100 | >100 |
| CPF 438 | 0.12 ± 0.02 | 51 ± 9 | | | 2.1 ± 0.6 | 32 ± 2 | 3.7 ± 0.5 | 72 ± 0 |
| CPF 373 | 0.015 ± 0.007 | 0.027 ± 0.004 | | | 0.089 ± 0.043 | 0.32 ± 0.07 | | |
| CPF 373(2) | 0.0061 ± 0.0043 | 0.064 ± 0.028 | 0.059 ± 0.046 | 0.74 ± 0.18 | 0.046 ± 0.010 | 0.74 ± 0.63 | 0.065 ± 0.013 | 2.5 ± 1.3 |
| CPF 381 | 0.028 ± 0.007 | 13 ± 8 | | | 0.18 ± 0.03 | 22 ± 7 | | |
| CPF 383 | 0.13 ± 0.04 | 0.94 ± 0.18 | 0.64 ± 0.57 | 4.1 ± 2.0 | 0.92 ± 0.11 | 14 ± 0 | 0.48 ± 0.19 | 9.8 ± 1.4 |
| CPF 384 | 0.076 ± 0.022 | 1.1 ± 0.1 | 0.36 ± 0.25 | 13 ± 1 | 1.0 ± 0.1 | 30 ± 10 | 0.71 ± 0.15 | 25 ± 11 |
| CPF 386 | 0.031 ± 0.005 | 0.36 ± 0.01 | | | 0.25 ± 0.04 | 1.6 ± 0.2 | 0.22 ± 0.04 | 2.8 ± 0.0 |
| CPF 393 | 0.017 ± 0.003 | 0.18 ± 0.05 | | | 0.23 ± 0.04 | 4.8 ± 0.7 | | |
| CPF 394 | 0.039 ± 0.001 | 4.6 ± 0.0 | | | 0.65 ± 0.16 | 22 ± 1 | | |
| CPF 395 | 0.011 ± 0.005 | 0.13 ± 0.04 | | | 0.16 ± 0.02 | 2.4 ± 0.8 | | |
| CPF 396 | 0.064 ± 0.008 | 0.82 ± 0.16 | | | 0.36 ± 0.05 | 6.9 ± 1.8 | | |
| CPF 508 | 0.039 ± 0.001 | 0.14 ± 0.02 | 0.18 ± 0.00 | | 0.17 ± 0.07 | | 0.18 ± 0.05 | |
| CPF 509 | 0.043 ± 0.023 | 0.15 ± 0.00 | 0.31 ± 0.06 | | 0.057 ± 0.055 | | 0.090 ± 0.014 | |
| CPF 576 | 1.1 ± 0.5 | 35 ± 8 | | | 0.80 ± 0.28 | 46 ± 14 | 0.67 ± 0.03 | 27 ± 6 |
| CPF 577 | 0.21 ± 0.08 | 25 ± 8 | | | 0.89 ± 0.35 | 32 ± 9 | 1.2 ± 0.0 | 26 ± 1 |
| CPF 578 | 0.014 ± 0.003 | 0.088 ± 0.038 | | | 0.073 ± 0.018 | 1.5 ± 0.3 | 0.069 ± 0.003 | 1.5 ± 0.6 |
| CPF 579 | 0.017 ± 0.007 | 0.12 ± 0.06 | | | 0.059 ± 0.017 | 1.1 ± 0.2 | 0.068 ± 0.001 | 1.4 ± 0.4 |
| CPF 580 | 0.038 ± 0.014 | 27 ± 6 | | | 0.11 ± 0.02 | 43 ± 12 | 0.13 ± 0.04 | 15 ± 7 |
| CPF 581 | 0.0028 ± 0.0010 | 0.13 ± 0.13 | | | 0.015 ± 0.006 | 0.28 ± 0.04 | 0.029 ± 0.023 | 0.44 ± 0.35 |
| CPF 582 | 0.031 ± 0.010 | 0.13 ± 0.02 | | | 0.035 ± 0.025 | 0.92 ± 0.007 | 0.071 ± 0.036 | 2.2 ± 1.3 |
| CPF 583 | 0.35 ± 0.07 | 31 ± 5 | | | 0.98 ± 0.40 | 28 ± 8 | 1.1 ± 0.4 | 20 ± 11 |
| CPF 585 | 0.016 ± 0.006 | 0.062 ± 0.009 | | | 0.053 ± 0.021 | 0.19 ± 0.04 | 0.078 ± 0.018 | 1.3 ± 0.9 |
| CPF 586 | 0.073 ± 0.035 | 4.1 ± 1.2 | | | 0.28 ± 0.03 | 25 ± 0 | 0.15 ± 0.02 | 11 ± 7 |
| CPF 587 | 0.012 ± 0.007 | 5.6 ± 1.3 | | | 0.10 ± 0.03 | 7.2 ± 0.1 | 0.16 ± 0.08 | 6.8 ± 1.5 |
| CPF 588 | 0.27 ± 0.11 | 1.2 ± 0.7 | | | 0.49 ± 0.05 | 6.7 ± 1.0 | 0.70 ± 0.11 | 32 ± 26 |
| CPF 589 | 0.022 ± 0.004 | 0.11 ± 0.06 | | | 0.064 ± 0.007 | 0.84 ± 0.60 | 0.12 ± 0.02 | 2.7 ± 1.5 |

Assay 2.

Samples were also assayed for their % retention of activity in mycoplasma infected cells. The results are set out in Table 2 below. The results show that compounds of the present invention can retain high activity in mycoplasma infected cells, in contrast to the activity shown by 5-FdUrd. Administration of a Thymidine Phosphorylase (TP) inhibitor restores the cytostatic activity of 5-FdUrd in myocoplasma infected cell cultures, providing evidence of the deteriorating role of TP in the eventual cytostatic activity of 5-FdUrd. As mycoplasma infection of cells is known to greatly reduce the activity of nucleosides, including 5-FdUrd, the activity of some

TABLE 2-continued

CC50 values in μM for 5-FdUrd and compounds embodying the present invention in mycoplasma negative and positive cells, and % retention of activity on mycoplasma infection. "% retention" is a measure of the ratio of the CC50 values measured with respect to L1210 with respect to those for L1210/Hyor and is calculated as $CC50_{L1210} \times 100 \div CC50_{L1210/Hyor}$

| Cpd | L1210 | L1210/Hyor | % Retention |
|---|---|---|---|
| CPF 581 | 0.0037 | 0.017 | 22 |
| CPF 582 | 0.035 | 0.042 | 83 |

TABLE 2-continued

CC50 values in μM for 5-FdUrd and compounds embodying the present invention in mycoplasma negative and positive cells, and % retention of activity on mycoplasma infection. "% retention" is a measure of the ratio of the CC50 values measured with respect to L1210 with respect to those for L1210/Hyor and is calculated as
$CC50_{L1210} \times 100 \div CC50_{L1210/Hyor}$.

| Cpd | L1210 | L1210/Hyor | % Retention |
|---|---|---|---|
| CPF 583 | 0.387 | 11.9 | 3.3 |
| CPF 585 | 0.021 | 0.051 | 41 |
| CPF 586 | 0.1 | 0.87 | 11 |
| CPF 587 | 0.022 | 4.2 | 0.5 |
| CPF 588 | 0.237 | 0.39 | 61 |
| CPF 589 | 0.02 | 0.063 | 32 |

Further experiments (Assays 3 to 8 below) were carried out with respect to the compound CPF 373 embodying the present invention.

Assay 3. Cytostatic Activity of 5-FdUrd and its Prodrug CPF-373 Against TK-Competent and TK-Deficient Tumour Cell Lines The cytostatic activity of 5-FdUrd and CPF-373 was determined in different TK-expressing and TK-deficient tumour cell lines. As shown in Table 3, 5-FdUrd is strongly dependent on the expression of TK for its cytostatic activity. Its $IC_{50}$ increased by 4,000-fold for L1210/TK⁻ cells ($IC_{50}$: 3.1 μM) versus wild-type L1210/0 cells ($IC_{50}$: 0.0008 μM) and by 50-fold for CEM/TK⁻ cells ($IC_{50}$: 1.5 μM) versus CEM/0 cells ($IC_{50}$: 0.028 μM). In contrast, the cytostatic activity of the 5-FdUrd prodrug CPF-373 remained virtually unchanged in TK-deficient cells when compared with wild-type cells ($IC_{50}$: 0.027 and 0.011 μM for L1210/TK⁻ and L1210/0, and 0.32 and 0.089 μM for CEM/TK⁻ and CEM/0 cells, respectively). Although the cytostatic activity of CPF-373 was 3- to 10-fold inferior to 5-FdUrd against wild-type L1210/0 and CEM/0 cells, it proved 5- to 100-fold superior to 5-FdUrd in the TK-deficient tumour cell lines (see Table 3).

TABLE 3

Cytostatic activity of 5-FdUrd and CPF-373 as represented by the $IC_{50}$ value in different cell lines

| | $IC_{50}{}^a$ (μM) | |
|---|---|---|
| Cell lines | 5-FdUrd | CPF-373 |
| L1210/0 | 0.0008 ± 0.000095 | 0.011 ± 0.0065 |
| L1210/TK⁻ | 3.1 ± 0.14 | 0.027 ± 0.0028 |
| L1210.Hyor | 0.24 ± 0.054 | 0.025 ± 0.0073 |
| CEM/0 | 0.028 ± 0.0014 | 0.089 ± 0.030 |
| CEM/TK⁻ | 1.5 ± 0.071 | 0.32 ± 0.049 |
| U87 | 0.007 ± 0.001 | 0.035 ± 0.0005 |
| U87.Hyor | 3.0 ± 0.55 | 0.039 ± 0.0025 |

$^a$50% Inhibitory concentration or compound concentration required to inhibit tumour cell proliferation by 50%

Assay 4. Effect of Mycoplasma Infection of Tumour Cell Cultures on the Cytostatic Activity of 5-FdUrd and its Prodrug CPF-373

The L1210/0 cell cultures were infected with the mycoplasma species M. hyorhinis (cells designated: L1210.Hyor). 5-FdUrd markedly lost its cytostatic activity against the mycoplasma-infected L1210.Hyor cells by 300-fold ($IC_{50}$: 0.24 μM). Also, 5-FdUrd lost its cytostatic activity by 400-fold in U87.Hyor cell cultures when compared with uninfected U87 cells (see Table 3). In sharp contrast, the 5-FdUrd prodrug CPF-373 kept a similar cytostatic potential in both L1210/0 and L1210.Hyor cell cultures ($IC_{50}$: 0.011 and 0.025 μM, respectively). A similar observation was made for this prodrug when evaluated for its cytostatic activity in U87 and U87.Hyor cell cultures ($IC_{50}$: 0.035 and 0.039 μM, respectively). Thus, whereas the free nucleoside 5-FdUrd markedly lost its cytostatic potential against Mycoplasma hyorhinis-infected tumour cell lines, the antiproliferative potential of its prodrug CPF-373 was independent of the mycoplasma infection.

Assay 5.

Experiments were carried out to assess the stability of CPF 373 in the presence of Thymidine Phosphorylase (TP). The experiments are illustrated with reference to FIGS. 9 to 11, each of which comprises NMR spectra, as discussed below. The present assay shows that the insensitivity of compounds embodying the present invention to the action of the catabolic enzyme TP, which is often upregulated in tumours, renders the compounds of the present invention more independent of the catabolic enzyme TP than 5-FdUrd.

Phosphorylase Assay on 5-FdUrd and its ProTide Compound CPF 373 by Thymidine Phosphorylase (TP) Purified from *Escherichia Coli*.

Nucleoside 5-FdUrd can be degraded to its relative base 5FU by a phosphorolytic reaction, using thymidine phosphorylase purified from *Escherichia coli* as well as uridine phosphorylase purified from Ehrlich ascite tumor. This breakdown has been suggested to be one of the reasons for the limited therapeutic effectiveness of 5-FdUrd according to the following scheme:

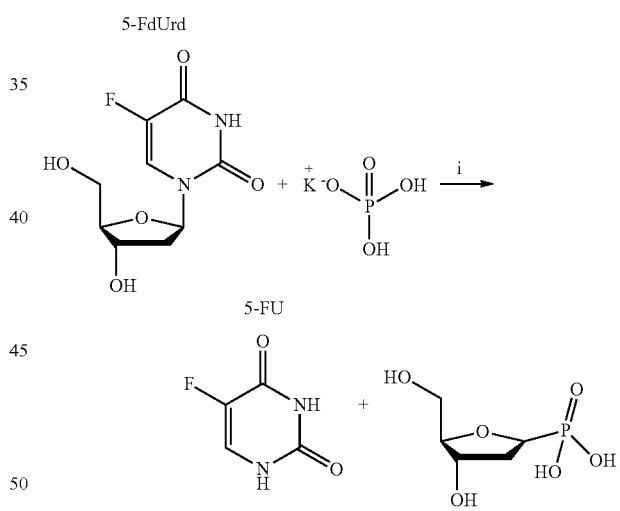

Scheme

The phosphorylase assay was carried out towards phosphorolysis by Thymidine Phosphorylase purified from *Escherichia coli* using in situ ¹⁹F NMR. The application to the ProTide compound CPF 373 was an attempt to prevent the cleavage of the structure and thus circumvent the action of the enzyme.

Two potassium phosphate buffers at pH=7.4, 200 nM solution and 300 nM solution respectively, were used as phosphate donor. Units of enzyme were defined as the amount of enzyme required to hydrolyse about 0.25 mg of inosine per min used as standard. Assays were conducted for 30 minutes.

Phosphorylase Assay on 5-FdUrd

Figure 9A:
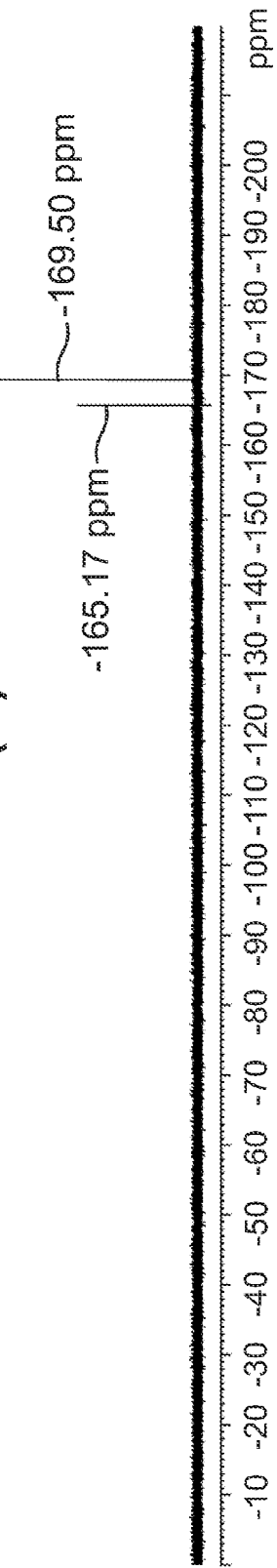
FIG. 9 shows spectra of nucleoside and relative base by $^{19}$F NMR: a) 5-FdUrd submitted to the phosphorylase assay (A); b) 5-FdUrd and the base 5FU under condition of the assay in absence of the enzyme (TP) (B)
Figure 9B:
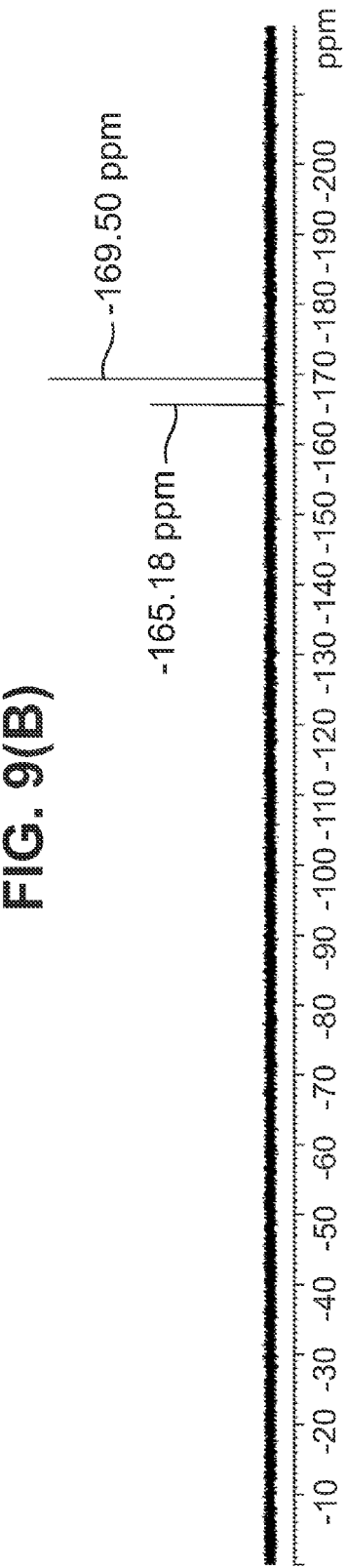

Initially, ¹⁹F NMR (470 MHz) spectra of 5-FdUrd and 5FU previously dissolved in deuterated methanol, were recorded. 5-FdUrd showed a singlet at ~δ−167.21 ppm and 5FU at ~δ–169.30 ppm. Thus, the phosphorylase assay was carried out by dissolving 5-FdUrd in deuterated methanol, in the presence of potassium phosphate buffer (200 nM solution; pH=7.4), recording the blank before of the addition of the enzyme thymidine phosphorylase (TP) (20.7 UNI). $^{19}$F NMR spectra, recorded at 25° C., showed the singlet of 5-FdUrd at ~δ–165.17 ppm and a new peak at ~δ–169.50 ppm, attributed to 5FU, as shown in FIG. 9 at spectrum A.

Then, to prove the cleavage of the nucleoside into the relative base, a new experiment was performed by dissolving equal moles of the nucleoside analogue 5-FdUrd and the relative base 5FU, at the same condition described above without the TS enzyme, as shown in FIG. 9 at spectrum B. This spectrum showed two singlets with the same chemical shifts previously observed in FIG. 9 spectrum A. These data confirmed that the 5FU has a chemical shift at ~δ–169.50 ppm and thus the phosphorolytic action of enzyme (TP). Conversion of nucleoside 5-FdURd into the free base 5FU was 66%.

When the initial concentration of potassium phosphate buffer was increased from 200 nM up to 205 nM, substrate 5-FdUrd was fully converted into the base 5-FU as shown in the FIG. 10.

Phosphorylase Assay on ProTide Compound CPF 373

Phosphorylase assay was applied to benzyl L-alanine phenyl derivative CPF 373 in order to investigate the stability, following the procedure and the conditions above described. ProTide compound CPF 373 proved to be completely stable as showed by comparing chemical shifts of sample analysed without TP enzyme, as shown in FIG. 11 spectrum A, and in the presence of TP, as shown in FIG. 11 spectrum B. $^{19}$F NMR was repeated after 4 days and the ProTide compound CPF 373 was shown once again to be stable.

These experiments confirmed that the nucleoside 5-FdUrd is rapidly degraded into its relative base 5FU by a phosphorolytic reaction, in the presence of thymidine phosphorylase, with a half-life of less than 30 minutes, while prodrug compound CPF 373 showed an evident stability against TP enzymatic activity, at longer time exposure up to 3 days. This important result showed that 5-FdUrd ProTides derivatives embodying the present invention could favor the therapeutic effect of 5-FdUrd.

Assay 6. Exposure of 5-FdUrd and CPF-373 to *E. Coli*-Encoded TP and Human-Encoded TP and UP The substrate specificity of thymidine phosphorylase towards natural thymidine (dThd), uridine (Urd), 5-FdUrd and CPF-373 was investigated by high pressure liquid chromatography (HPLC). Reaction mixtures containing 100 M test compound and recombinant TP or UP (human TP: 8.6 ng/μL; *E. coli* TP: 3.0 ng/μL; human UP: 4 ng/mL) in a total volume of 500 μL reaction buffer (10 mM TrisHCl; 300 μM NaCl; 1 mM EDTA; 2 mM $KH_2PO_4/K_2HPO_4$) were incubated at room temperature. At different time points (i.e. 0, 20, 40 min) 100 μL aliquots of the reaction mixtures were withdrawn and heated at 95° C. for 3 min to inactivate the enzyme. The resulting reaction products were separated on a reverse-phase RP-8 column (Merck, Darmstadt, Germany) and quantified by HPLC analysis (Alliance 2690, Waters, Milford, Mass.). The separation of dThd from thymine was performed by a linear gradient from 98% separation buffer (50 mM $NaH_2PO_4$ and 5 mM heptane sulfonic acid, pH 3.2) and 2% acetonitrile, to 20% separation buffer+80% acetonitrile (8 min 98% separation buffer+2% acetonitrile; 5 min linear gradient of 98% separation buffer+2% acetonitrile to 20% separation buffer+80% acetonitrile; 10 min 20% separation buffer+80% acetonitrile, followed by equilibration at 98% separation buffer+2% acetonitrile). UV-based detection was performed at 267 nm. The separation of Urd from uracil was performed by a linear gradient from 100% separation buffer (see above) to 60% separation buffer+40% acetonitrile (3 min 100% separation buffer; 6 min linear gradient of 100% separation buffer to 60% separation buffer+40% acetonitrile; 6 min 60% separation buffer+40% acetonitrile, followed by equilibration at 100% separation buffer). UV-based detection was performed at 258 nm.

Phosphorolysis of 5-FdUrd and CPF-373 by Thymidine and Uridine Phosphorylases

Figure 2A:
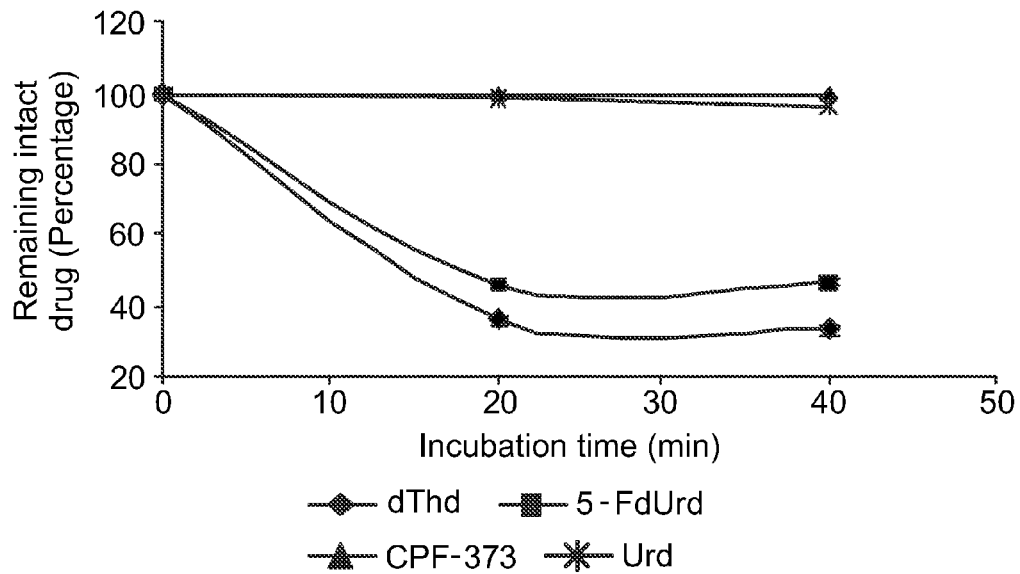
FIG. 2 shows the effect of thymidine phosphorylase and uridine phosphorylase on dThd, Urd, 5-FdUrd and CPF-373, where data are the mean of at least 2 independent experiments (±S.D.)
Figure 2B:
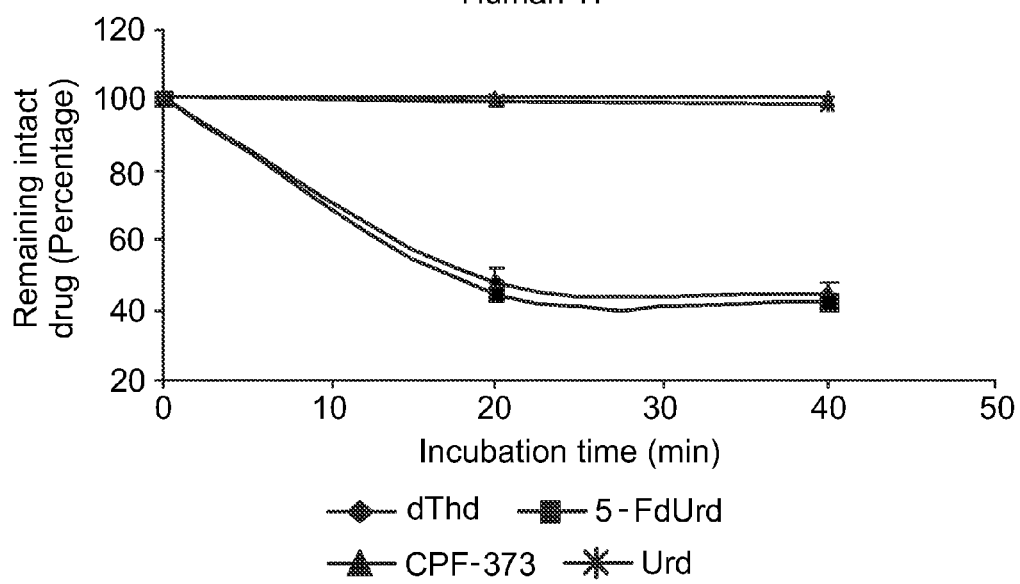
Figure 3A:
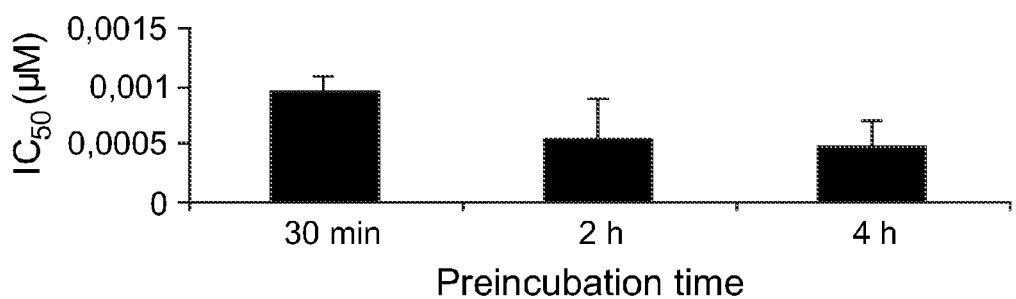
FIG. 3 shows the inhibition of TS by 5-FdUrd and CPF-373 as measured by tritium release from [5-$^3$H]dUrd (panels A and B) and [5-$^3$H]dCyd (panels C and D) in L1210/0 cell cultures and by tritium release from [5-$^3$H]dCyd (panels E and F) in L1210/TK-cell cultures, where data are the mean of 2 independent experiments (±S.E.M.)
Figure 3B:
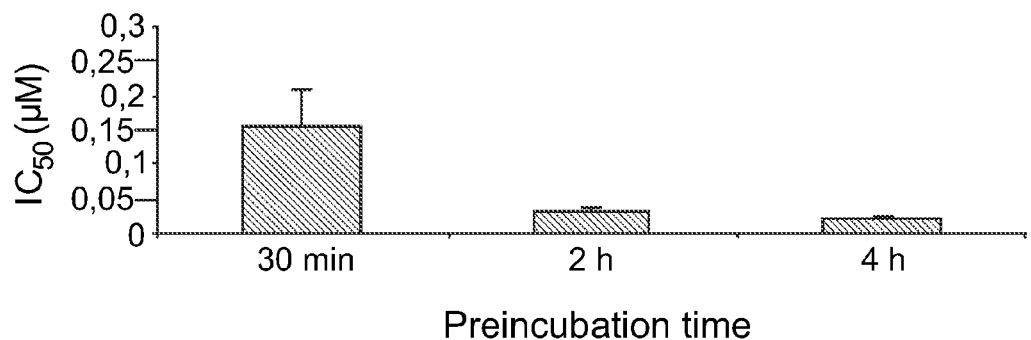
Figure 3C:
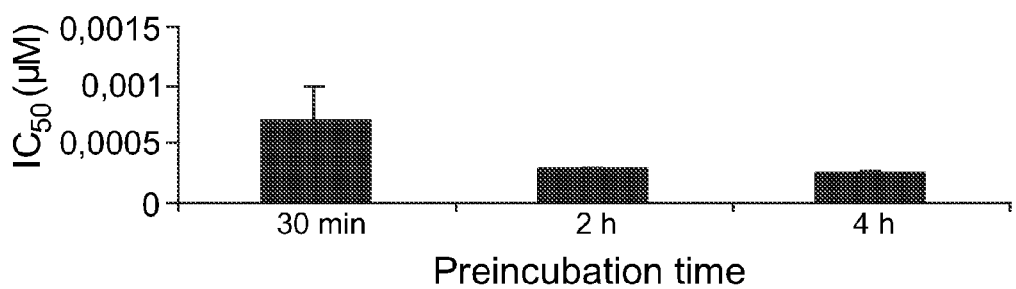
Figure 3D:
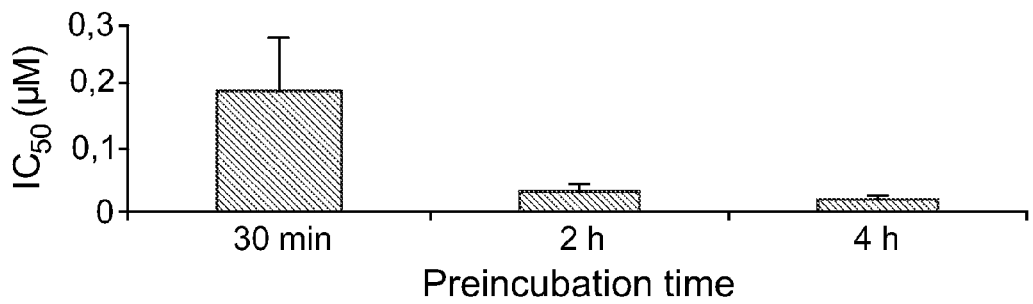
Figure 3E:
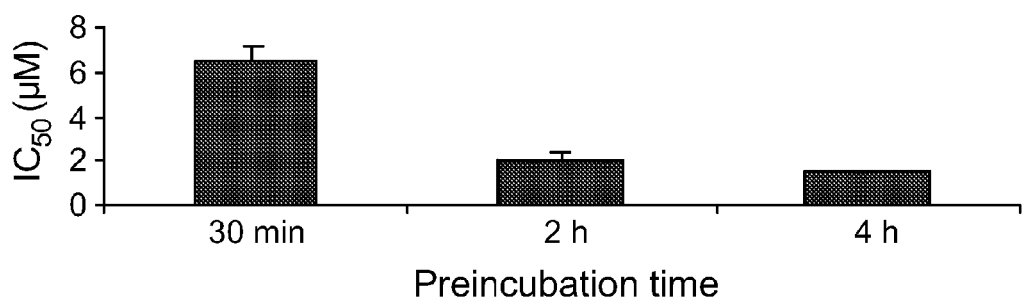
Figure 3F:
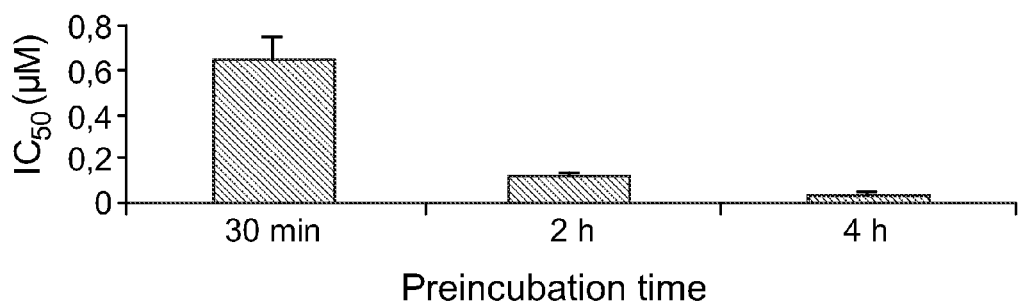

5-FdUrd and its prodrug CPF-373 were exposed to purified thymidine phosphorylase derived from *E. coli* or human erythrocytes, and to purified uridine phosphorylase derived from human tumors. Whereas *E. coli* and human TP rapidly converted dThd and 5-FdUrd to their free bases, CPF-373 kept fully stable in the presence of these enzymes (FIG. 2). Under similar experimental conditions, uridine was converted to uracil by human UP, but not by *E. coli* TP, or human TP. When both compounds were exposed to UP, dThd and CPF-373 were not affected by the enzyme, whereas 5-FdUrd was slightly hydrolysed (FIG. 2, panel C).

Assay 7. Thymidylate Synthase (TS) Activity Measurements

The activity of TS in intact L1210/0 and L1210/TK-cells was measured by evaluation of tritium release from [5-$^3$H] dUMP (formed in the cells from [5-$^3$H]dUrd or [5-$^3$H]dCyd) in the reaction catalysed by TS. This method has been described in detail by Balzarini & De Clercq (1984). Shortly, cell cultures (500 L DMEM culture medium) were prepared containing ~3×10$^6$ L1210 cells and appropriate amounts of the test compounds (5-FdUrd and CPF-373). After 30 min, 2 h and 4 h preincubation of the cells with the compounds at 37° C., 1 μCi of [5-$^3$H]dUrd or [5-$^3$H]dCyd was added to the cell cultures. After 30 min incubation, 100 μL of the cell suspensions were withdrawn and added to a cold suspension of 500 μL activated charcoal (VWR, Haasrode, Belgium) (100 mg/ml in TCA 5%). After 10 min, the suspension was centrifuged at 13,000 rpm for 10 min, after which the radioactivity in 400 μL supernatant was counted in a liquid sinctillator using OptiPhase HiSafe (Perkin Elmer, Waldham, Mass.).

Inhibition of Thymidylate Synthase (TS) by 5-FdUrd and CPF-373

The major target for the cytostatic activity of 5-FdUrd is thymidylate synthase (TS). The activity of TS in intact tumour cells can be directly monitored by measuring the tritium release in intact L1210/0 cell cultures that were exposed to [5-$^3$H]deoxyuridine ([5-$^3$H]dUrd) or [5-$^3$H] deoxycytidine ([5-$^3$H]dCyd). Indeed, after intracellular conversion of [5-$^3$H]dUrd or [5-$^3$H]dCyd to [5-$^3$H]dUMP, the C-5 tritium atom on the pyrimidine base is released during the TS-catalysed reductive methylation. The ability of 5-FdUrd and its prodrug CPF-373 to inhibit tritium release from [5-$^3$H] dUrd and [5-$^3$H]dCyd was therefore evaluated in L1210/0 cell cultures at a variety of compound concentrations. 5-FdUrd proved to be a potent inhibitor of TS in situ. Its $IC_{50}$ for tritium release from [5-$^3$H]dCyd and [5-$^3$H]dUrd was around 0.0007-0.0009 μM (see Table 4).

TABLE 4

$IC_{50}$ values of 5-FdUrd and CPF-373 against TS in intact L1210/0 tumour cells (as determined by tritium release from [5-$^3$H]dUrd and [5-$^3$H]dCyd after 30 min exposure to the drugs).

| Compound | $IC_{50}{}^a$ (μM) | |
|---|---|---|
| | Tritium release from dUrd* | Tritium release from dCyd* |
| 5-FdUrd | 0.0009 ± 0.0002 | 0.0007 ± 0.003 |
| CPF-373 | 0.16 ± 0.05 | 0.19 ± 0.08 |

$^a$50% Inhibitory concentration or compound concentration required to inhibit tritium release from [5-$^3$H]dUrd or [5-$^3$H]dCyd in drug-exposed L1210/0 cell cultures by 50%.

The inhibitory activity of CPF-373 on tritium release was much less (~200-fold) pronounced than that of 5-FdUrd, especially after only 30 min preincubation of the cells with the drugs ($IC_{50}$: 0.16-0.19 μM). However, longer preincubation times of the cells (up to 4 hr) with 5-FdUrd and CPF-373 before measuring TS activity in the intact tumour cells revealed a much more pronounced inhibitory activity of the prodrug against TS in situ (FIG. 3). Indeed, whereas the inhibition of $^3$H release was only 2-fold increased upon longer preincubation times of 5-FdUrd, the inhibitory potential of CPF-373 increased 10-fold (FIG. 3, panels A and B, and C and D).

Preincubation of the tumour cells with 5-FdUrd and CPF-373 for at least 4 hrs results in TS inhibition in the intact tumour cells at drug concentrations that are very comparable with the 50% cytostatic activity concentrations of these drugs.

The present observations thus indicate that the 5-FdUrd prodrug needs several metabolic conversion steps before reaching TS as the target enzyme for inhibition, and support the view that CPF-373 acts as an efficient prodrug of 5-FdUrd to exert its eventual cytostatic activity.

The activity of TS in the presence of 5-FdUrd and CPF-373 was also measured in intact L1210/TK$^-$ cells using [5-$^3$H] dCyd as an externally supplied substrate (due to TK deficiency, [5-$^3$H]dUrd cannot be used). As demonstrated in Table 5 and FIG. 3 (panels E and F), the concentration of 5-FdUrd required to cause 50% inhibition of TS decreased by a factor 5,700 in TK-deficient L1210/TK$^-$ cells ($IC_{50}$: 1.4 μM) when compared to wild-type L1210/0 cells ($IC_{50}$: 0.0003 μM). In contrast, the inhibitory activity of CPF-373 against TS remained virtually unchanged in L1210/TK$^-$ cells ($IC_{50}$: 0.053 μM in L1210/TK$^-$ cells versus 0.013 M in L1210/0 cells).

TABLE 5

$IC_{50}$ values of 5-FdUrd and CPF-373 against TS in intact L1210/0 and L1210/TK$^-$ cells (as determined by tritium release from [5-$^3$H]dCyd after 4 hours of preincubation with the products)

| Compound | $IC_{50}{}^a$ (μM) | |
| --- | --- | --- |
|  | L1210/0 | L1210/TK$^-$ |
| 5-FdUrd | 0.0003 ± 0.00003 | 1.42 ± 0.09 |
| CPF-373 | 0.013 ± 0.008 | 0.053 ± 0.0009 |

$^a$50% Inhibitory concentration or compound concentration required to inhibit tritium release from [5-$^3$H]dCyd in drug-exposed L1210 cells by 50% upon pre-exposure of the tumour cells for 4 hrs to the drugs.

Assay 8. Stability Assays
Carboxypeptidase Y (EC 3.4.16.1) Assay

The enzymatic stability of the prodrug CPF-373 towards carboxypeptidase Y was studied using in situ $^{31}$P NMR (202 MHz). The experiment was carried out by dissolving CPF-373 (3.0 mg) in $d_6$-acetone (150 μL) and adding TRIZMA buffer pH 7.6 (300 μL). The resulting solution was placed in an NMR tube and a $^{31}$P-NMR experiment at 25° C. was recorded as the blank experiment. The enzyme Carboxypeptidase Y (0.2 mg) was solubilised in TRIZMA (150 μL) and added to the solution of the phosphoramidate derivative in the NMR tube. Next, the tube was placed in the NMR machine, which was set to run a $^{31}$P-NMR experiment (64 scans) every 4 minutes for 14 hours at 25° C. Data were processed and analysed with the Bruker Topspin 2.1 program. Carboxypeptidase Y and TRIZMA buffer were purchased from Sigma-Aldrich.

Human Serum

The stability of the prodrug CPF-373 in the presence of human serum was studied using in situ $^{31}$P NMR (202 MHz). The ProTide CPF-373 (1) (5.0 mg) was dissolved in DMSO (0.05 mL) and $D_2O$ (0.15 mL). Then the sample was transferred into an NMR tube, which was inserted in the NMR chamber at 37° C. (with enough solvent to obtain a control NMR reading of the blank). Then 0.3 ml human serum was quickly added to the sample in the NMR tube. NMR experiments were programmed to record data every 15 minutes for 12 hours and minutes. Because of excess noise and poor shimming profiles (most likely due to the biological media and concentration), individual spectra were further processed. After normal Fourier transform processing, each spectrum was deconvoluted (Lorentz-Gauss deconvolution) to reveal solely the frequency and area of spectral peaks without the baseline. Data recorded were processed and analysed with the Bruker Topspin 2.1 program.

Buffer at pH 1

The stability of the prodrug CPF-373 towards hydrolysis at pH=1 was studied using in situ $^{31}$P NMR (202 MHz). The ProTide CPF-373 (1) (2.6 mg) was dissolved in MeOD (0.1 mL) after which 0.5 mL buffer (pH=1) (prepared from equal parts of 0.2 M HCl and 0.2 M KCl) was added. Then the sample was transferred into an NMR tube, and a $^{31}$P NMR experiment was performed at 37° C. recording the data every 12 minutes for 14 hours. Data were processed and analysed with the Bruker Topspin 2.1 program.

Buffer at pH 8

The stability of the prodrug CPF-373 towards hydrolysis at pH=8 was studied using in situ $^{31}$P NMR (202 MHz). The ProTide CPF-373 (1) (4.9 mg) was dissolved in MeOD (0.1 mL) after which 0.5 mL buffer (pH=8) (prepared from a solution of 0.1 M $Na_2HPO_4$, which was adjusted by 0.1 M HCl) was added. Then the sample was transferred into an NMR tube, and a $^{31}$P NMR experiment was performed at 37° C. recording the data every 12 minutes for 14 hours. Data were processed and analysed with the Bruker Topspin 2.1 program.

Stability Studies

Figure 6:
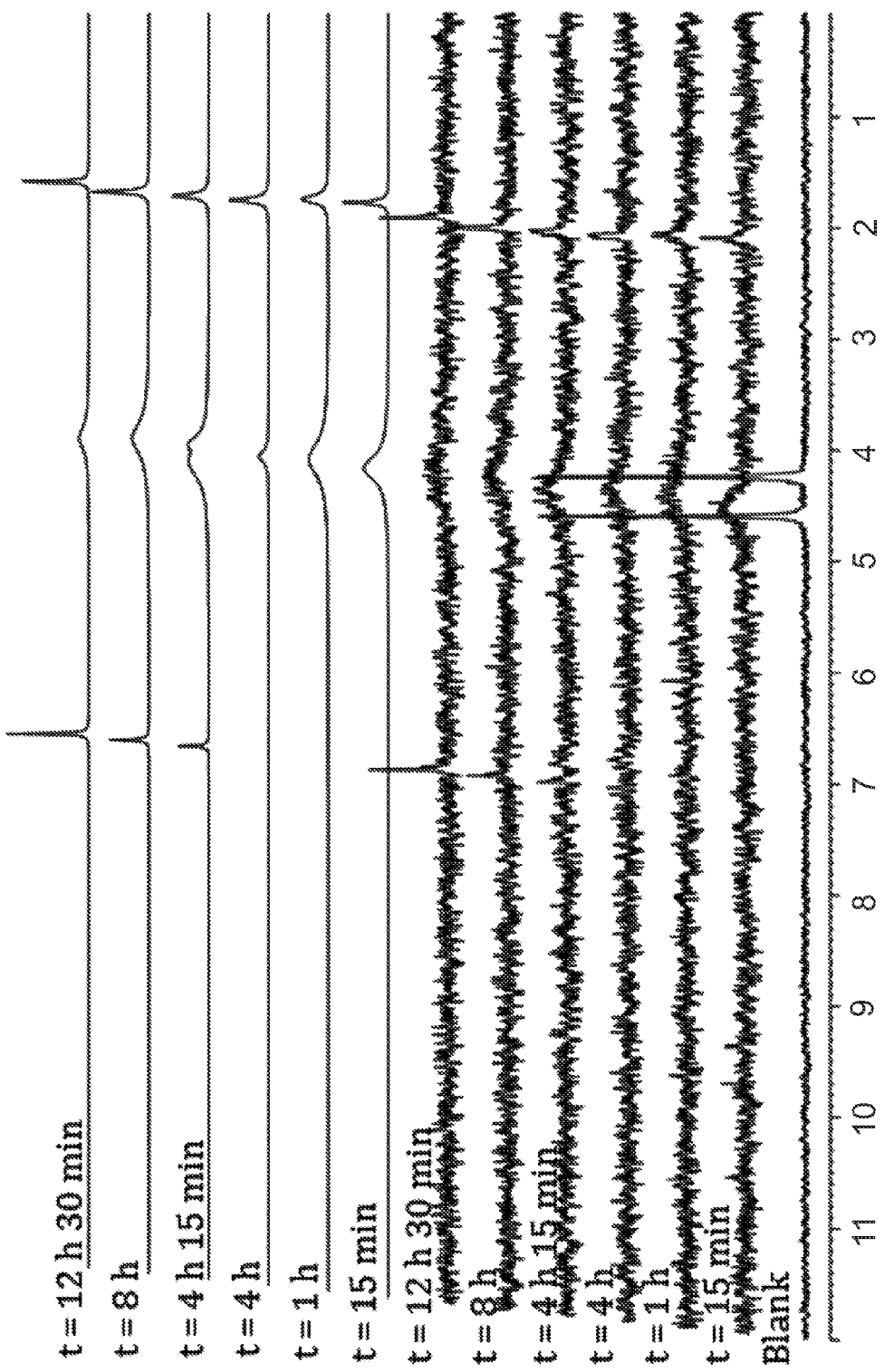
FIG. 6 shows $^{31}$P NMR spectrum of compound CPF-373 in serum.

Chemical stability studies on the prodrug CPF-373 (1) have been performed by exposing the compound to human serum and to aqueous buffers (pH 1.0 and 8.0) using in situ $^{31}$P NMR. Each experiment has been carried out dissolving the ProTide in the suitable deuterated solvent and analysing the samples at 37° C. for about 14 hours, acquiring scans at the regular time intervals. For a better resolution original spectra (lower graphs) and deconvoluted ones (upper graphs) are reported. The stability assay of the phosphoramidate CPF-373 (1), after incubation in human serum, showed 73% of unchanged compound after 12 hours and 30 minutes as shown in FIG. 6.

The spectra displayed a singlet peak inherent to the human serum at ~δ 2.00 and the double peak of the parent at ~δ 4.50 which after 4 hours and minutes was hydrolyzed to the aminoacyl phosphoramidate intermediate shown as a singlet peak at δ7.20.

Figure 7:
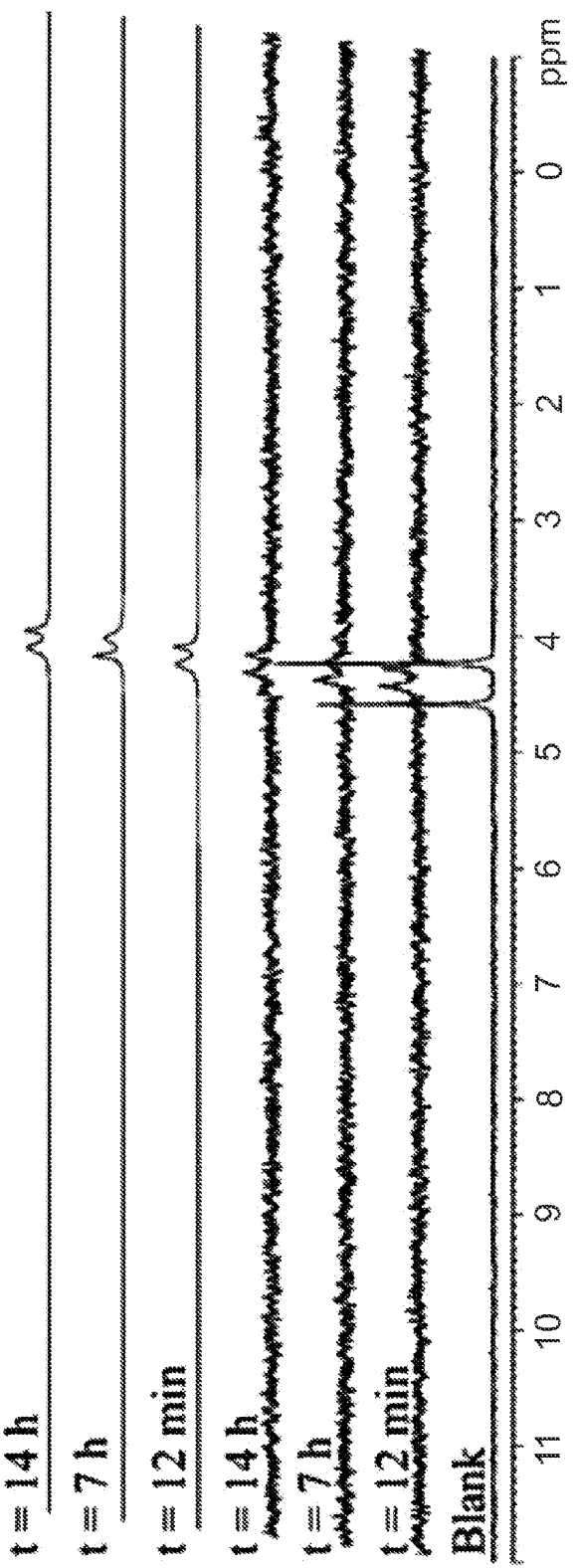
FIG. 7 shows $^{31}$P NMR spectrum of compound CPF-373 in buffer pH=1.
Figure 8:
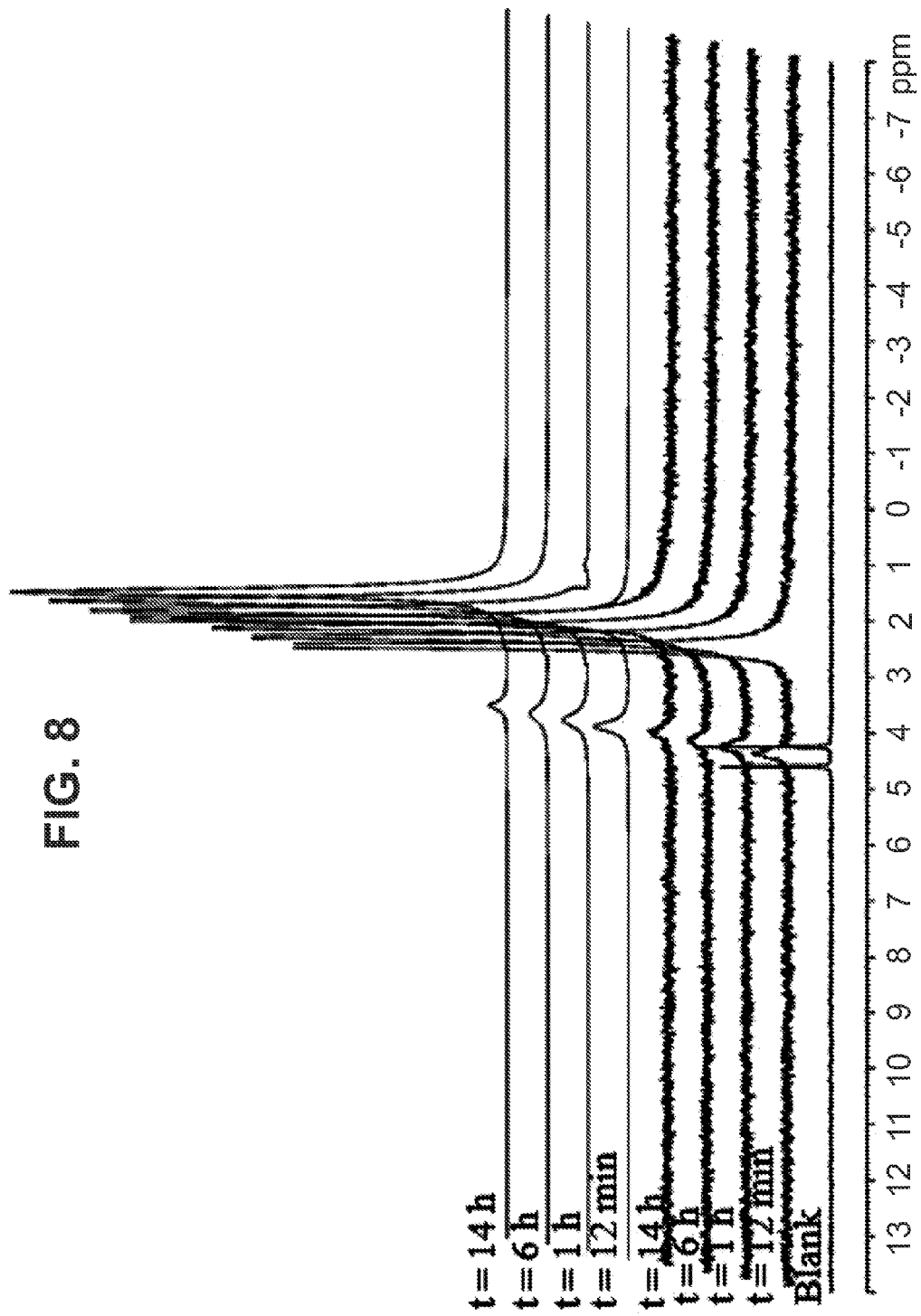
FIG. 8 shows $^{31}$P NMR spectrum of compound CPF-373 in buffer pH=8.

When chemical hydrolysis was evaluated at extreme experimental conditions, i.e. at pH 1.0 and pH 8.0 at 37° C., a full stability of prodrug CPF-373 (1) in both acidic and basic buffer conditions was observed. Spectra were recorded for 14 hours acquiring scans every 12 minutes at regular intervals as shown in the FIGS. 7 and 8. The ProTide (1) examined at pH 1.0 showed constant doublet peaks of diastereoisomers at δ4.35; 4.50 throughout the time of the assay (FIG. 7). Also, at pH 8.0 the spectra displayed a persistent peak of the prodrug (1) at δ4.48 and a singlet peak at 62.55 corresponding to a buffer peak (FIG. 8).

Metabolism of 5-FdUrd Phosphoramidates

Figure 4:
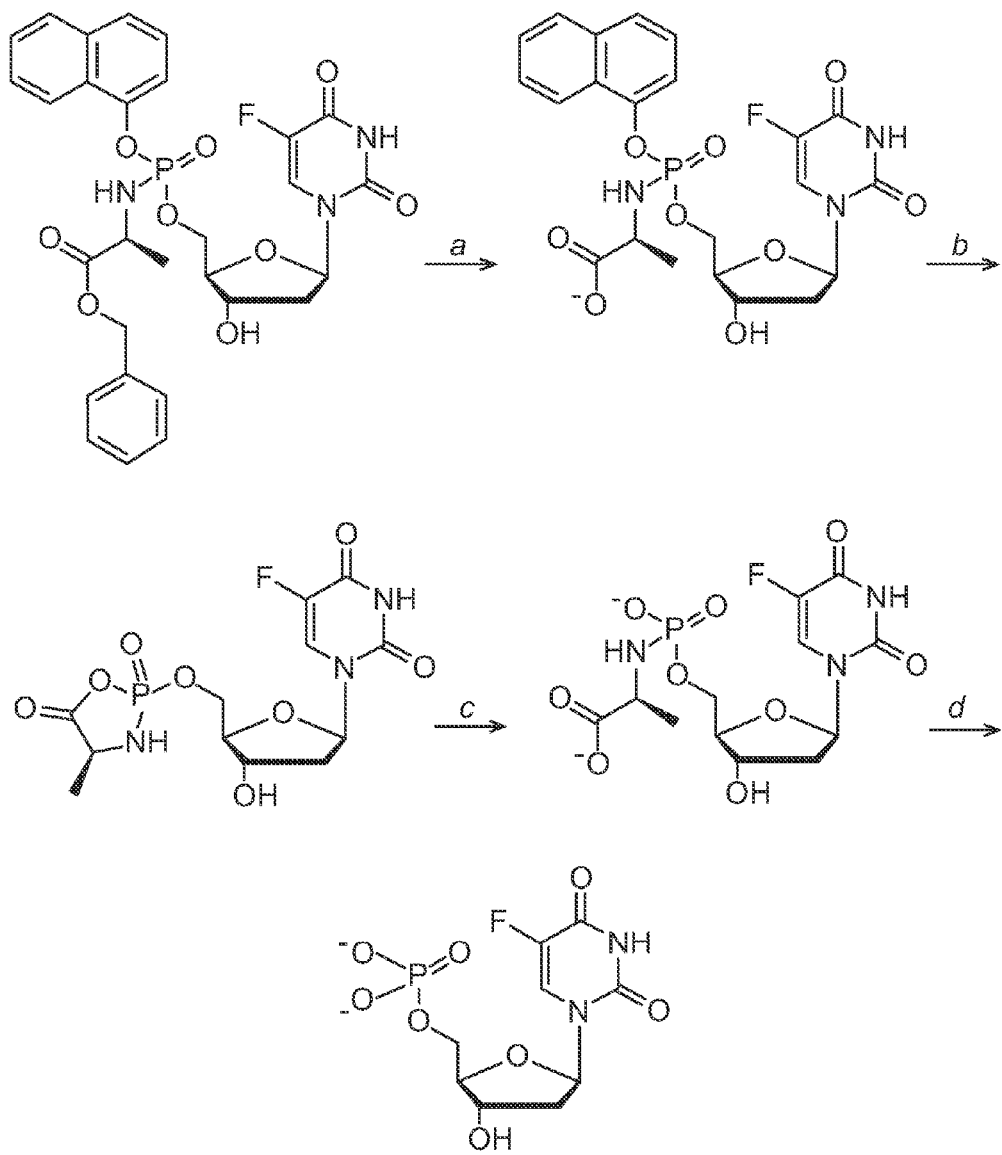
FIG. 4 shows a proposed putative mechanism of activation of 5-FdUrd ProTides.

As shown in FIG. 4, the putative mechanism of activation of the ProTides inside the cell, after uptake, involves a first enzymatic activation step mediated by a carboxypeptidase-type enzyme which hydrolyzes the ester of the aminoacyl moiety (step a) followed by spontaneous cyclization and subsequent spontaneous displacement of the aryl group (step b) and opening of the unstable ring mediated by water (step c). The last step involves a hydrolysis of the P—N bond mediated by a phosphoramidase-type enzyme (step d) with release of the nucleoside monophosphate in the intact cell (FIG. 4) (McGuigan et al., 2009; Mehellou et al., 2010).

Figure 5:
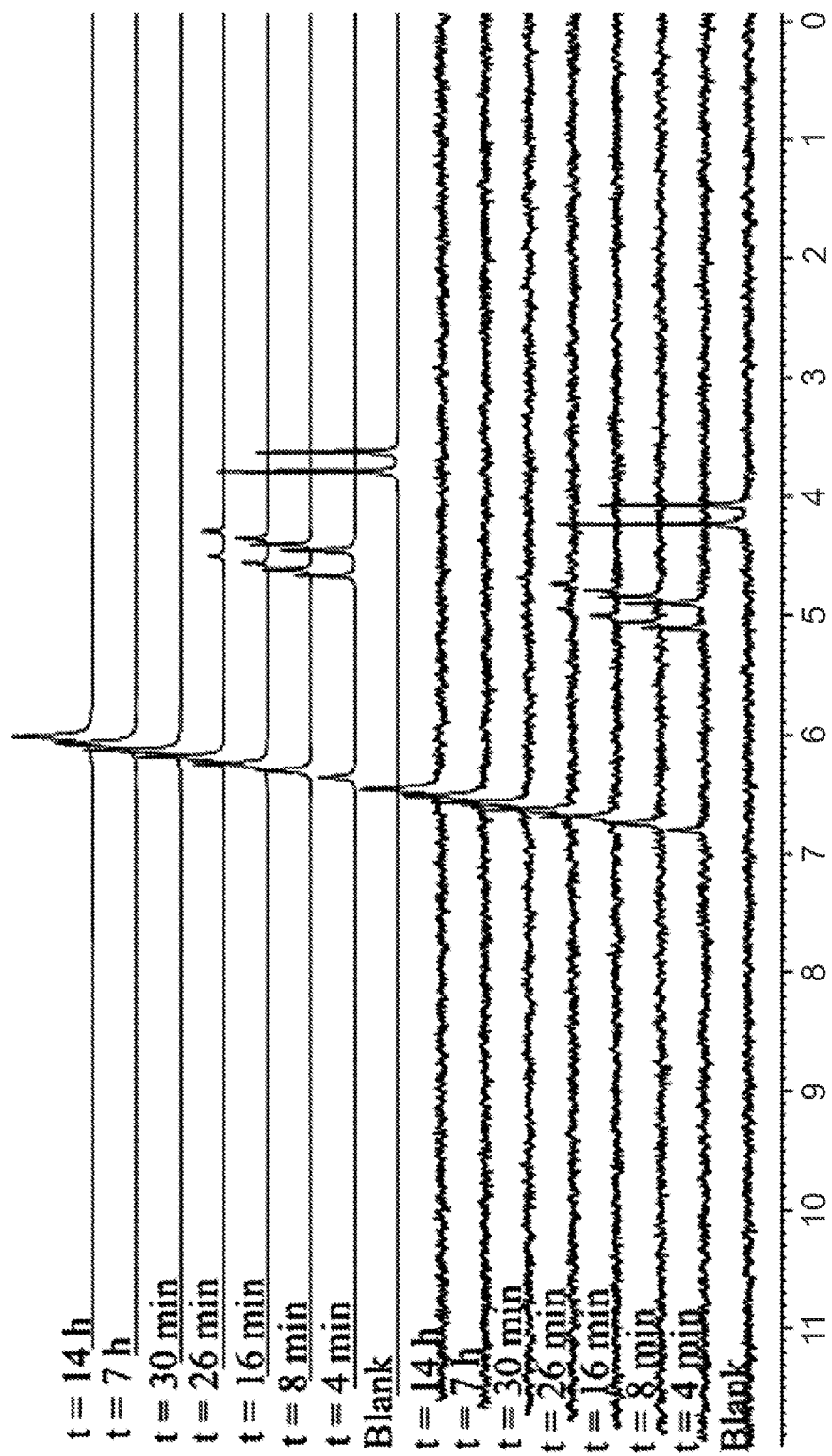
FIG. 5 shows carboxypeptidase-mediated cleavage of prodrug CPF-373 monitored by $^{31}$P NMR.

To prove the proposed metabolic scheme for CPF-373 (1) and whether the ester motif of the 5-FdUrd phosphoramidate derivative is cleaved-off or not, an enzyme incubation experiment was carried out that was designed to mimic the first stages of the putative activation in the intact tumour cells. The compound (I) was incubated with carboxypeptidase Y (also known as cathepsin A) in TRIZMA buffer and the conversion of (1) was monitored by $^{31}$P NMR. Spectra were recorded for 14 h acquiring scans at the periodic intervals every 4 minutes as shown in FIG. 5. For a better resolution original spectra (lower graphs) and deconvoluted ones (upper graphs) are shown.

At the $^{31}$P NMR the prodrug CPF-373 (1) appeared as two peaks δ4.07; 4.23 corresponding with the two diastereoisomers noted as parent with the characteristic doubling-up of the chiral phosphate centre of the phosphoramidate. After the addition of cathepsin A the compound was quickly hydrolyzed after 4 minutes to intermediates δ4.95; 5.16 which lack the ester motif and this intermediate did not persist as it was in turn quickly metabolized to the aminoacyl phosphoramidate intermediate, the final product in this assay, via the loss of the aryl group (steps a to c in FIG. 4). The intermediate appeared as a singlet peak at δ6.85 due to the achiral phosphate centre. Thus, the enzymatic assay spectra showed a fast metabolism of the parent ~δ4.00 with complete conversion to the putative intermediate within 26 minutes, which further stayed consistently present throughout the 14 h of the assay. The cleavage of the P—N bond releasing the nucleoside monophosphate was not detected in the enzyme experiment, as expected. This experiment indicates that the first activation step of ProTide CPF-373 (1) may be sufficiently efficient, and therefore, may allow the eventual delivery of the nucleoside monophosphate metabolite in the intact tumour cells.

CONCLUSION

In conclusion, the present invention provides novel phosphoramidate nucleotide prodrugs of the anticancer nucleoside analogue 5-fluoro-2'-deoxyuridine (5-FdUrd), which were synthesized and evaluated for their cytostatic activity. Whereas 5-FdUrd substantially lost its cytostatic potential in thymidine kinase (TK)-deficient murine leukaemia L1210 and human lymphocyte CEM cell cultures, compounds of the present invention, for example CPF-373, markedly kept their antiproliferative activity in both the wild-type and TK-deficient tumour cells and are thus largely independent of intracellular TK activity to exert their cytostatic action. CPF-373, for example, was found to inhibit thymidylate synthase (TS) in the TK-deficient and wild-type cell lines at drug concentrations that correlated well with its cytostatic activity in these cells. CPF-373 does not seem to be susceptible to inactivation by catabolic enzymes such as thymidine phosphorylase (TP) and uridine phosphorylase (UP). These findings are in line with the observations that 5-FdUrd, but not CPF-373, substantially loses its cytostatic potential in the presence of TP-expressing mycoplasmas in the tumour cell cultures. Therefore, compounds of the present invention such as CPF-373 are novel 5-FdUrd phosphoramidate prodrugs that (i) may circumvent potential resistance mechanisms of tumour cells (e.g. decreased TK activity) and (ii) is not degraded by catabolic enzymes such as TP whose activity is often upregulated in tumour cells or expressed in mycoplasma-infected tumour tissue. Incorporated in by reference in its entirety is Vande Voorde, J. et al Biochemical Pharmacology 82 (2011) 441-452.

Embodiments of the present invention, as set out below, are disclosed in McGuigan, C. et al J. Med. Chem. 2011, 54 7247-7258 (published Sep. 5, 2011), the contents of which in their entirety are hereby incorporated by reference.

Table 6 below records the cytostatic activity of 5-FU, 5-FdUrd, reference example CPF382 and compounds embodying the present invention against tumour cell lines in terms of $IC_{50}$ or compound concentration required to inhibit tumour cell proliferation by 50%. Data are the mean (±SD) of at least two to four independent experiments. Table 6 identifies the phosphoramidate motif of reference example CPF382 and of compounds embodying the present invention with respect to: "aryl", which corresponds to Ar of Formula I and is either phenyl (Ph) or 1-naphthyl (Nap); "ester", which corresponds to $R_3$ of Formula I; and "AA", which sets out the amino acid whose alpha C atom and substituents on the alpha C atom correspond to $CR_1R_2$ of Formula I. Table 6 discloses compounds embodying the present invention not previously mentioned above in Table 1, as well as additional data for some of the compounds mentioned in Table 1.

TABLE 6

| Compd | aryl | Ester | AA | $IC_{50}$ (μM) | | | | | |
|---|---|---|---|---|---|---|---|---|---|
| | | | | L1210/0 | L1210/TK⁻ | Cem/0 | Cem/TK⁻ | HeLa | HeLa/TK⁻ |
| 5-FU | | | | 0.33 ± 0.17 | 0.32 ± 0.31 | 18 ± 5 | 12 ± 1 | 0.54 ± 0.12 | 0.23 ± 0.01 |
| 5-FdUrd | | | | 0.0011 ± 0.0002 | 3.0 ± 0.1 | 0.022 ± 0.006 | 3.0 ± 0.4 | 0.050 ± 0.011 | 1.4 ± 0.4 |
| | Ph | Me | Ala | 0.022 ± 0.007 | 41 ± 3 | 0.70 ± 0.37 | 35 ± 12 | 0.28 ± 0.14 | 4.7 ± 0.4 |
| | Ph | Et | Ala | 0.13 ± 0.04 | 0.94 ± 0.18 | 0.92 ± 0.11 | 14 ± 0 | 0.48 ± 0.19 | 9.8 ± 1.4 |
| | Ph | i-Pr | Ala | 0.076 ± 0.022 | 1.1 ± 0.1 | 1.0 ± 0.1 | 30 ± 10 | 0.71 ± 0.15 | 25 ± 11 |
| | Ph | c-Hex | Ala | 0.039 ± 0.001 | 0.14 ± 0.02 | 0.17 ± 0.07 | 1.2 ± 0.01 | 0.18 ± 0.05 | 5.9 ± 0.4 |
| | Ph | Bn | Ala | 0.028 ± 0.007 | 13 ± 8 | 0.18 ± 0.03 | 22 ± 7 | 0.13 ± 0.01 | 19 ± 2 |
| | Ph | Et | Val | 0.16 ± 0.05 | 42 ± 2 | 1.0 ± 0.1 | >250 | 1.2 ± 0.3 | 27 ± 7 |
| | Ph | Bn | Leu | 0.044 ± 0.025 | 2.0 ± 0.3 | 0.24 ± 0.04 | 16 ± 1 | 0.067 ± 0.042 | 5.6 ± 0.3 |
| | Ph | Bn | Ile | 0.076 ± 0.022 | 1.1 ± 0.1 | 1.0 ± 0.1 | 30 ± 10 | 0.71 ± 0.15 | 25 ± 11 |
| | Ph | Bn | Phe | 0.036 ± 0.010 | 39 ± 4 | 0.25 ± 0.02 | 11 ± 3 | 0.014 ± 0.007 | 12 ± 2 |
| | Ph | Pnt | Met | 0.11 ± 0.06 | 2.2 ± 0.5 | 0.35 ± 0.13 | 13 ± 1 | 0.15 ± 0.00 | 7.1 ± 1.2 |
| | Ph | Bn | Met | 0.073 ± 0.035 | 4.1 ± 1.2 | 0.28 ± 0.03 | 25 ± 0 | 0.15 ± 0.02 | 11 ± 7 |
| | Ph | Bn | Pro | 0.35 ± 0.07 | 31 ± 5 | 0.98 ± 0.40 | 28 ± 8 | 1.1 ± 0.4 | 20 ± 11 |
| | Ph | Et | DMG | 0.039 ± 0.001 | 4.6 ± 0.0 | 0.65 ± 0.16 | 22 ± 1 | 0.59 ± 0.09 | 17 ± 2 |
| | Ph | Bn | DMG | 0.017 ± 0.003 | 0.18 ± 0.05 | 0.23 ± 0.04 | 4.8 ± 0.7 | 0.24 ± 0.07 | 3.7 ± 0.1 |

TABLE 6-continued

| Compd | aryl | Ester | AA | IC$_{50}$ (μM) | | | | | |
| --- | --- | --- | --- | --- | --- | --- | --- | --- | --- |
| | | | | L1210/0 | L1210/TK$^-$ | Cem/0 | Cem/TK$^-$ | HeLa | HeLa/TK$^-$ |
| | Nap | Et | Ala | 0.031 ± 0.005 | 0.36 ± 0.01 | 0.25 ± 0.04 | 1.6 ± 0.2 | 0.22 ± 0.04 | 2.8 ± 0.0 |
| | Nap | Pr | Ala | 0.021 ± 0.012 | 0.16 ± 0.07 | 0.14 ± 0.01 | 1.1 ± 0.2 | 0.11 ± 0.03 | 2.5 ± 0.1 |
| | Nap | Butyl | Ala | 0.022 ± 0.004 | 0.11 ± 0.06 | 0.064 ± 0.007 | 0.84 ± 0.60 | 0.12 ± 0.02 | 2.7 ± 1.5 |
| | Nap | Pnt | Ala | 0.0028 ± 0.0010 | 0.13 ± 0.13 | 0.015 ± 0.006 | 0.28 ± 0.04 | 0.029 ± 0.023 | 0.44 ± 0.35 |
| | Nap | Hex | Ala | 0.0072 ± 0.0000 | 0.076 ± 0.015 | 0.080 ± 0.020 | 0.65 ± 0.34 | 0.039 ± 0.018 | 1.8 ± 0.1 |
| | Nap | c-Bu | Ala | 0.014 ± 0.003 | 0.088 ± 0.038 | 0.073 ± 0.018 | 1.5 ± 0.3 | 0.069 ± 0.003 | 1.5 ± 0.6 |
| | Nap | c-Pnt | Ala | 0.031 ± 0.010 | 0.13 ± 0.02 | 0.35 ± 0.025 | 0.92 ± 0.007 | 0.071 ± 0.036 | 2.2 ± 1.3 |
| | Nap | c-Hex | Ala | 0.043 ± 0.023 | 0.15 ± 0.00 | 0.057 ± 0.055 | 1.0 ± 0.1 | 0.090 ± 0.014 | ND |
| | Nap | CH$_2$-t-Bu | Ala | 0.27 ± 0.11 | 1.2 ± 0.7 | 0.49 ± 0.05 | 6.7 ± 1.0 | 0.70 ± 0.11 | 32 ± 26 |
| | Nap | CH$_2$CH$_2$-t-Bu | Ala | 0.016 ± 0.006 | 0.062 ± 0.009 | 0.053 ± 0.021 | 0.19 ± 0.04 | 0.078 ± 0.018 | 1.3 ± 0.9 |
| | Nap | CH$_2$-c-Pr | Ala | 0.017 ± 0.007 | 0.12 ± 0.06 | 0.059 ± 0.017 | 1.1 ± 0.2 | 0.068 ± 0.001 | 1.4 ± 0.4 |
| | Nap | 2-Ind | Ala | 0.021 ± 0.002 | 40 ± 0 | 0.079 ± 0.018 | 1.0 ± 0.2 | 0.10 ± 0.06 | 7.1 ± 2.1 |
| | Nap | Bn | Ala | 0.011 ± 0.005 | 0.045 ± 0.027 | 0.068 ± 0.035 | 0.31 ± 0.06 | 0.065 ± 0.013 | 2.5 ± 1.3 |
| | Nap | THP | Ala | 0.038 ± 0.014 | 27 ± 6 | 0.11 ± 0.02 | 43 ± 12 | 0.13 ± 0.04 | 15 ± 7 |
| | Nap | c-Hex | Val | 1.1 ± 0.5 | 35 ± 8 | 0.80 ± 0.28 | 46 ± 14 | 0.67 ± 0.03 | 27 ± 6 |
| | Nap | Pnt | Leu | 0.017 ± 0.001 | 1.2 ± 0.4 | 0.071 ± 0.008 | 15 ± 4 | 0.039 ± 0.014 | 7.5 ± 0.4 |
| | Nap | Bn | Leu | 0.028 ± 0.004 | 1.5 ± 0.6 | 0.13 ± 0.00 | 30 ± 6 | 0.080 ± 0.022 | 9.4 ± 1.4 |
| | Nap | Pnt | Ile | 0.22 ± 0.12 | 12 ± 2 | 0.46 ± 0.11 | 17 ± 1 | 0.30 ± 0.02 | 11 ± 1 |
| | Nap | Pnt | Phe | 0.026 ± 0.001 | 2.9 ± 1.2 | 0.10 ± 0.00 | 8.3 ± 1.0 | 0.040 ± 0.000 | 6.6 ± 0.5 |
| | Nap | Bn | Phe | 0.012 ± 0.007 | 5.6 ± 1.3 | 0.10 ± 0.03 | 7.2 ± 0.1 | 0.16 ± 0.08 | 6.8 ± 1.5 |
| | Nap | Bn | Met | 0.072 ± 0.001 | 1.9 ± 0.2 | 0.19 ± 0.10 | 11 ± 1 | 0.087 ± 0.017 | 8.3 ± 0.0 |
| | Nap | Bn | Pro | 0.21 ± 0.08 | 25 ± 8 | 0.89 ± 0.35 | 35 ± 9 | 1.2 ± 0.0 | 26 ± 1 |
| | Nap | Et | DMG | 0.064 ± 0.008 | 0.82 ± 0.16 | 0.36 ± 0.05 | 6.9 ± 1.8 | 0.20 ± 0.12 | 3.2 ± 0.0 |
| | Nap | Pnt | DMG | 0.037 ± 0.010 | 0.30 ± 0.13 | 0.14 ± 0.00 | 5.4 ± 1.1 | 0.12 ± 0.03 | 2.3 ± 0.1 |
| | Nap | Bn | DMG | 0.011 ± 0.005 | 0.13 ± 0.04 | 0.16 ± 0.02 | 2.4 ± 0.8 | 0.078 ± 0.020 | 3.1 ± 0.6 |

Table 7 below records the cytostatic activity of 5-FdUrd, reference example CPF382 and compounds embodying the present invention in wild type murine leukemia L1210 cell cultures (L1210/0) and L1210 cell cultures, infected with *Mycoplasma hyorhinis* (L1210.Hyor) in terms of IC$_{50}$ or compound concentration to inhibit cell proliferation by 50%. Data are mean (±SD) of at least two to four independent experiments. Table 7 identifies the phosphoramidate motif of reference example CPF382 and of compounds embodying the present invention, as discussed above with respect to Table 6, but with "Naph" standing for 1-naphthyl. Table 7 discloses compounds embodying the present invention not previously mentioned above in Table 2, as well as additional data for some of the compounds mentioned in Table 2.

TABLE 7

| Compd | aryl | ester | AA | IC$_{50}$ (μM) | | IC$_{50}$(L1210.Hyor)/IC$_{50}$(L1210/0) |
| --- | --- | --- | --- | --- | --- | --- |
| | | | | L1210/0 | L1210.Hyor | |
| 5-FdUrd | | | | 0.0009 ± 0.0003 | 0.34 ± 0.13 | 378 |
| | Ph | Me | Ala | 0.040 ± 0.016 | 0.87 ± 0.28 | 22 |
| | Ph | Et | Ala | 0.11 ± 0.0021 | 0.54 ± 0.12 | 5 |
| | Ph | i-Pr | Ala | 0.050 ± 0.013 | 0.70 ± 0.10 | 14 |
| | Ph | c-Hex | Ala | 0.032 ± 0.0050 | 0.040 ± 0.016 | 1.25 |
| | Ph | Bn | Ala | 0.026 ± 0.008 | 0.15 ± 0.006 | 5.8 |
| | Ph | Et | Val | 0.20 ± 0.033 | 4.4 ± 1.1 | 22 |
| | Ph | Bn | Leu | 0.054 ± 0.0021 | 0.17 ± 0.047 | 3.2 |
| | Ph | Bn | Ile | 0.98 ± 0.39 | 2.2 ± 0.031 | 2.2 |
| | Ph | Bn | Phe | 0.016 ± 0.0014 | 0.56 ± 0.023 | 35 |
| | Ph | Pnt | Met | 0.13 ± 0.0078 | 0.41 ± 0.21 | 3.2 |
| | Ph | Bn | Met | 0.058 ± 0.035 | 0.76 ± 0.18 | 13 |
| | Ph | Bn | Pro | 0.35 ± 0.022 | 18 ± 0.71 | 51 |
| | Ph | Et | DMG | 0.030 ± 0.0005 | 0.26 ± 0.01 | 8.7 |
| | Ph | Bn | DMG | 0.029 ± 0.001 | 0.02 ± 0.002 | 0.69 |
| | Naph | Et | Ala | 0.028 ± 0.0021 | 0.095 ± 0.0028 | 3.4 |
| | Naph | Pr | Ala | 0.030 ± 0.00035 | 0.036 ± 0.0064 | 1.2 |
| | Naph | butyl | Ala | 0.0095 ± 0.0021 | 0.021 ± 0.0071 | 2.2 |
| | Naph | Pnt | Ala | 0.0021 ± 0.00007 | 0.006 ± 0.0014 | 2.9 |
| | Naph | Hex | Ala | 0.0032 ± 0.00035 | 0.0022 ± 0.00028 | 0.69 |
| | Naph | c-Bu | Ala | 0.011 ± 0.0014 | 0.024 ± 0.00014 | 2.2 |
| | Naph | c-Pnt | Ala | 0.016 ± 0.0007 | 0.024 ± 0.005 | 1.5 |
| | Naph | c-Hex | Ala | 0.036 ± 0.017 | 0.049 ± 0.004 | 1.4 |
| | Naph | CH$_2$—t-Bu | Ala | 0.093 ± 0.033 | 0.18 ± 0.069 | 1.9 |
| | Naph | CH$_2$CH$_2$—t-Bu | Ala | 0.012 ± 0.0018 | 0.032 ± 0.0088 | 2.7 |
| | Naph | CH$_2$—c-Pr | Ala | 0.014 v 0.0042 | 0.031 ± 0.0064 | 2.2 |
| | Naph | 2-Ind | Ala | 0.039 ± 0.019 | 0.042 ± 0.040 | 1.08 |
| | Naph | Bu | Ala | 0.011 ± 0.009 | 0.025 ± 0.01 | 2.27 |
| | Naph | THP | Ala | 0.041 ± 0.0028 | 0.48 ± 0.11 | 11.7 |
| | Naph | c-Hex | Val | 1.2 ± 0.17 | 1.29 ± 0.29 | 1.08 |
| | Naph | Pnt | Leu | 0.031 ± 0.0020 | 0.035 ± 0.010 | 1.13 |
| | Naph | Bn | Leu | 0.029 ± 0.0021 | 0.048 ± 0.020 | 1.7 |

TABLE 7-continued

| | | | | IC$_{50}$ (μM) | | |
|---|---|---|---|---|---|---|
| Compd | aryl | ester | AA | L1210/0 | L1210.Hyor | IC$_{50}$(L1210.Hyor)/IC$_{50}$(L1210/0) |
| | Naph | Pnt | Ile | 0.42 ± 0.021 | 0.70 ± 0.074 | 1.67 |
| | Naph | Pnt | Phe | 0.030 ± 0.0039 | 0.14 ± 0.007 | 4.67 |
| | Naph | Bn | Phe | 0.021 ± 0.0061 | 0.23 ± 0.078 | 11 |
| | Naph | Bn | Met | 0.054 ± 0.013 | 0.20 ± 0.098 | 3.7 |
| | Naph | Bn | Pro | 0.26 ± 0.055 | 0.65 ± 0.070 | 2.5 |
| | Naph | Et | DMG | 0.056 ± 0.04 | 0.17 ± 0.03 | 3 |
| | Naph | Pnt | DMG | 0.045 ± 0.0021 | 0.019 ± 0.0028 | 0.42 |
| | Naph | Bn | DMG | 0.019 ± 0.004 | 0.045 ± 0.004 | 2.4 |

Table 8 below records the cytostatic activity of 5-FdUrd and compounds embodying the present invention in CEM cell cultures containing (Cem/hEnt-1) or lacking (Cem/hEnt-0) the hEnt1 transporter in terms of IC$_{50}$ or compound concentration required to inhibit tumour cell proliferation by 50%. Data are mean (±SD) of at least two to four independent experiments. Table 8 identifies the phosphoramidate motif of compounds embodying the present invention, as discussed above with respect to Table 6, but with "Naph" standing for 1-naphthyl. The data of Table 8 show that compounds embodying the present invention are less dependent on the presence of the hENT1 transporter, than 5-FdUrd, since they lose only 7- to 15-fold antiproliferative activity against the hENT1-deficient CEM cells. These observations are in agreement with an only 2- to 7-fold decreased cytostatic activity of compounds embodying the present invention in the presence of transport inhibitors (i.e. dipyridamole and NBMPR), compared to a 20- to 60-fold loss of antiproliferative activity of 5-FdUrd and FdUMP under similar experimental conditions.

$^{31}$P NMR spectrum (202 MHz) spectra were recorded at regular intervals (every 7 min) over 14 h. Compound CPF 581 was rapidly hydrolyzed to a first metabolite lacking the ester (R$_3$) moiety, both diastereoisomers being processed at roughly similar rate. Further processing of the first metabolite led to the formation of an anionic second metabolite, lacking Ar, within about 45 min with an estimated half life of less than 5 min. The rate of the initial activation step might thus be considered in general as one of requirments for good biological actrivity of phosphoramidates. Chemical hydrolysis of compound CPF 373 in the presence of triethylamine and water produced the diammonium salt of the anionic second metabolite, which was added to the final assay sample derived from compound CPF 373, i.e. containing only the enzymatic second metabolite derived from compound CPF 581 in Trizma. The sample had a $^{31}$P NMR spectrum showing only a single peak at δ$_P$ 6.85 ppm, strongly supporting this part of

TABLE 8

| | | | | IC$_{50}$ (μM) | | | |
|---|---|---|---|---|---|---|---|
| compd | aryl | Ester | AA | Cem/hEnt-1 | Cem/hEnt-0 | Cem/hEnt-1 + dipyridamole | Cem/hEnt-1 + NBMPR |
| 5-FdUMP | | | | 0.05 ± 0.02 | 3.6 ± 0.69 | 1.74 | 1.06 |
| 5-FdUrd | | | | 0.04 ± 0.02 | 2.5 ± 0.65 | 1.36 | 0.80 |
| | Ph | Bn | Ala | 0.13 ± 0.05 | 1.4 ± 0.65 | 0.66 | 0.72 |
| | Ph | Et | DMG | 0.37 ± 0.14 | 5.8 ± 0.50 | 2.35 | 2.56 |
| | Ph | Bn | DMG | 0.17 ± 0.06 | 1.2 ± 0.11 | 0.26 | 0.61 |
| | Naph | Bn | Ala | 0.05 ± 0.02 | 0.6 ± 0.11 | 0.13 | 0.26 |
| | Naph | Et | DMG | 0.21 ± 0.07 | 1.4 ± 0.20 | 0.52 | 0.62 |
| | Naph | Bn | DMG | 0.05 ± 0.03 | 0.4 ± 0.13 | 0.16 | 0.28 |

Studies were performed on compound CPF 381 as follows: An enzymatic phosphorylase assay was carried out using thymidine phosphorylase (TP, purified from *Esherichia coli*) in the presence of potassium phosphate buffer (300 nM solution, pH 7.4). The $^{19}$F NMR spectrum after 5 min, 14 h and 72 h did not show any evidence of phosphorolysis. In contrast to 5-FdUrd, CPF 381 is at best a very poor, if any, substrate for thymidine phosphorylase.

A chemical hydrolysis was evaluated under experimental conditions at pH 1 and pH 8 and monitored by $^{31}$P NMR. During the assay (14 h) under acidic conditions (pH 1) only two peaks representing the two diastereoisomers were recorded. Lack of formation of new signals in the $^{31}$P NMR spectrum indicates that compound CPF 381 is highly stable in acidic medium. The same result was observed when compound CPF 381 was subjected to the assay under mild basic conditions (pH 8).

Studies were performed on compound CPF 581 as follows: A enzymatic study using a carboxypeptidase Y assay was performed in which compound CPF 581, carboxypeptidase Y, and Trizma buffer (pH 7.6) were dissolved in acetone-d$_6$ and the metabolic pathway and activation of the phosphoramidate compounds of the present invention.

Studies were performed on compound CPF 386 as follows: The stability of compound CPF 386 in the presence of human serum was investigated using in situ $^{31}$P NMR. A control $^{31}$P NMR data of compound CPF 386 in DMSO and D$_2$O were recorded. The NMR sample was then treated with human serum and immediately subjected to further $^{31}$P NMR experiments at 37° C. The $^{31}$P NMR data were recorded every 15 minutes over 14 h. The spectra displayed a single peak inherent to human serum at ~δ 2.00 ppm and two peaks corresponding to compound CPF 386 at ~δ$_P$ 4.59 and 4.84 ppm. After about 6 h and 45 min the compound was hydrolyzed partly to an intermediate, lacking R$_3$ (Et), as a single peak at δ$_P$ 5.79 ppm. After 11 h and min, the formation of the second metabolite, lacking Ar (1-naphthyl), shown as single peak at δ$_P$ 7.09 ppm was observed. After 13 h and 30 min the reaction mixture contained 96% of the parent compound CPF 386 together with the proposed first metabolite (3%) and second metabolite (1%).

REFERENCES

Agarwal R P, Han T, Fernandez M, Collateral resistance of a dideoxycytidine-resistant cell line to 5-fluoro-2'-deoxyuridine. Biochem Biophys Res Commun 1999; 262:657-60.

Ayusawa D, Koyama H, Iwata K, Seno T, Single-step selection of mouse FM3A cell mutants defective in thymidylate synthetase. Somatic Cell Genet. 1980; 6:261-70.

Ayusawa D, Koyama H, Seno T, Resistance to methotrexate in thymidylate synthetase-deficient mutants of cultured mouse mammary tumor FM3A cells. Cancer Res 1981; 41:1497-501.

Balzarini J, De Clercq E, Torrence P F, Mertes M P, Park J S, Schmidt C L, Shugar D, Barr P J, Jones A S, Verhelst G, Walker R T, Role of thymidine kinase in the inhibitory activity of 5-substituted-2'-deoxyuridines on the growth of human and murine tumor cell lines. Biohcem Pharmacol 1982:31:1089-1095

Balzarini J and De Clercq E, Strategies for the measurement of the inhibitory effects of thymidine analogs on the activity of thymidylate synthase in intact murine leukemia L1210 cells. Biochim Biophys Acta 1984; 785:36-45.

Beck A, Etienne M C, Cheradame S, Fischel J L, Formento P, Renee N, Milano G, A role for dihydropyrimidine dehydrogenase and thymidylate synthase in tumour sensitivity to fluorouracil. Eur J Cancer 1994; 30A:1517-22.

Bronckaers A, Balzarini J, Liekens S, The cytostatic activity of pyrimidine nucleosides is strongly modulated by *Mycoplasma* hyorhinis infection: Implications for cancer therapy. Biochem Pharmacol 2008; 76:188-97.

Bronckaers A, Gago F, Balzarini J, Liekens S, The dual role of thymidine phosphorylase in cancer development and chemotherapy. Med Res Rev 2009; 29:903-53.

Chan P J, Seraj I M, Kalugdan T H, King A, Prevalence of mycoplasma conserved DNA in malignant ovarian cancer detected using sensitive PCR-ELISA. Gynecol Oncol 1996; 63:258-60.

Charron J and Langelier Y, Analysis of deoxycytidine (dC) deaminase activity in herpes simplex virus-infected or HSV TK-transformed cells: association with mycoplasma contamination but not with virus infection. J Gen Virol 1981; 57:245-50.

Ciaparrone M, Quirino M, Schinzari G, Zannoni G, Corsi D C, Vecchio F M, Cassano A, La Torre G, Barone C. Predictive role of thymidylate synthase, dihydropyrimidine dehydrogenase and thymidine phosphorylase expression in colorectal cancer patients receiving adjuvant 5-fluorouracil. *Oncology* 2006; 70:366-77.

Ciccolini J, Evrard A, Cug P. Thymidine phosphorylase and fluoropyrimidines efficacy: a Jekyll and Hyde story. *Curr Med Chem Anticancer Agents* 2004; 4:71-81.

Congiatu C, Brancale A, Mason M D, Jiang W G, McGuigan C, Novel potential anticancer naphthyl phosphoramidates of BVdU: separation of diastereoisomers and assignment of the absolute configuration of the phosphorus center. J Med Chem 2006; 49:452-5.

de Bruin M, van Capel T, Smid K, van der Born K, Fukushima M, Hoekman K, Pinedo H M, Peters G J, Role of platelet derived endothelial cell growth factor/thymidine phosphorylase in fluoropyrimidine sensitivity and potential role of deoxyribose-1-phosphate. Nucleosides Nucleotides Nucleic Acids 2004; 23:1485-90.

Galmarini C M, Mackey J R, Dumontet C, Nucleoside analogues and nucleobases in cancer treatment. Lancet Oncol 2002; 3:415-24.

Harris S A, McGuigan C, Andrei G, Snoeck R, De C E, Balzarini J, Synthesis and antiviral evaluation of phosphoramidate derivatives of (E)-5-(2-bromovinyl)-2'-deoxyuridine. Antivir Chem Chemother 2001; 12:293-300.

Hatse S, De C E, Balzarini J, Role of antimetabolites of purine and pyrimidine nucleotide metabolism in tumor cell differentiation. Biochem Pharmacol 1999; 58:539-55.

Hecker S J and Erion M D, Prodrugs of phosphates and phosphonates. J Med Chem 2008; 51:2328-45.

Huang S, Li J Y, Wu i, Meng L, Shou C C, *Mycoplasma* infections and different human carcinomas. World J Gastroenterol 2001; 7:266-9.

Ishikawa T, Utoh M, Sawada N, Nishida M, Fukase Y, Sekiguchi F, Ishitsuka H, Tumor selective delivery of 5-fluorouracil by capecitabine, a new oral fluoropyrimidine carbamate, in human cancer xenografts. Biochem Pharmacol 1998; 55:1091-7.

Jetté L, Bissoon-Haqqani S, Le F B, Maroun J A, Birnboim H C, Resistance of colorectal cancer cells to 5-FUdR and 5-FU caused by *Mycoplasma* infection. Anticancer Res 2008; 28:2175-80.

Kamoshida S, Shiogama K, Shimomura R, Inada K, Sakurai Y, Ochiai M, Matuoka H, Maeda K, Tsutsumi Y. Immunohistochemical demonstration of fluoropyrimidine-metabolizing enzymes in various types of cancer. Oncol Rep. 2005. 14:1223-30.

Kidder M, Chan P J, Seraj I M, Patton W C, King A. Assessment of archived paraffin-embedded cervical condyloma tissues for mycoplasma-conserved DNA using sensitive PCR-ELISA. Gynecol Oncol 1998; 71:254-257.

Kinsella A R and Smith D, Tumor resistance to antimetabolites. Gen Pharmacol 1998; 30:623-6.

Koopman M, Venderbosch S, Nagtegaal I D, van Krieken J H, Punt C J. A review on the use of molecular markers of cytotoxic therapy for colorectal cancer, what have we learned? *Eur J Cancer* 2009; 45: 1935-49.

Kosaka T, Usami K, Ueshige N, Sugaya J. Nakano Y. Takashima S. Effects of thymidine phosphorylase levels in cancer, background mucosa, and regional lymph nodes on survival of advanced gastric cancer patients receiving postoperative fluoropyrimidine therapy. *Oncol Rep* 2004; 12:1279-86.

Liekens S, Bronckaers A, Balzarini J, Improvement of purine and pyrimidine antimetabolite-based anticancer treatment by selective suppression of mycoplasma-encoded catabolic enzymes. Lancet Oncol 2009; 10:628-35.

Longley D B, Harkin D P, Johnston P G, 5-fluorouracil: mechanisms of action and clinical strategies. Nat Rev Cancer 2003; 3:330-8.

McGuigan, C.; Pathirana, R. N.; Balzarini, J.; De Clercq, E. Intracellular delivery of bioactive AZT nucleotides by aryl phosphate derivatives of AZT. *J. Med. Chem.* 1993, 36, 1048.

McGuigan, C.; Cahard, D.; Hendrika, D.; Sheeka, M.; De Clercq, E.; Balzarini, J. *Aryl phosphoramidate derivatives of d4T have improved anti-HIV efficacy in tissue vulture and may act by the generation of a novel intracellular metabolite.* J. Med. Chem. 1996, 39, 1748.

McGuigan, C.; Tsang, H. W.; Cahardr, D. Turner, K.; Velazquez, S.; Salgado, A.; Bidois, L.; Naesens, L.; De Clercq, E.; Balzarini, J. *Phosphoramidate derivatives of d4T as inhibitors of HIV: The effect of amino acid variation.* Antiviral Res. 1997, 35, 195.

McGuigan, C.; Mehellou, J.; Balzarini, J. Aryloxy phosphoramidate triesters: a technology for delivering mono-phosphorylated nucleosides and sugars into cells. Chem. Med. Chem., 2009, 4, 11, 1779.

McGuigan C, Gilles A, Madela K, Aljarah M, Holl S, Jones S, Vernachio J, Hutchins J, Ames B, Bryant K D, Gorovits E, Ganguly B, Hunley D, Hall A, Kolykhalov A, Liu Y, Muhammad J, Raja N, Walters R, Wang J, Chamberlain S, Henson G, Phosphoramidate ProTides of 2'-C-methylguanosine as highly potent inhibitors of hepatitis C virus. Study of their in vitro and in vivo properties. J Med Chem 2010; 53:4949-57.

Mehellou Y, Balzarini J, McGuigan C, Aryloxy phosphoramidate triesters: a technology for delivering monophosphorylated nucleosides and sugars into cells. ChemMedChem 2009; 4:1779-91.

Mehellou, Y.; Valente, R.; Mottram, H.; Walsby, E.; Mills, K. I.; Balzarini, J.; Mcgugan, C. *Phosphoramidates of 2'-β-d-arabinouridine (AraU) as phosphate prodrugs; design, synthesis, in vitro activity and metabolism*. Bioorg. Med. Chem. 2010, 18, 2439

Moertel C G, Chemotherapy for colorectal cancer. N Engl J Med 1994; 330:1136-42.

Murakami Y, Kazuno H, Emura T, Tsujimoto H, Suzuki N, Fukushima M, Different mechanisms of acquired resistance to fluorinated pyrimidines in human colorectal cancer cells. Int J Oncol 2000; 17:277-83.

Neale G A, Mitchell A, Finch L R, Enzymes of pyrimidine deoxyribonucleotide metabolism in *Mycoplasma mycoides* subsp. mycoides. J Bacteriol 1983; 156:1001-5.

Pehlivan M, Pehlivan S, Onay H, Koyuncuoglu M, Kirkali Z, Can mycoplasma-mediated oncogenesis be responsible for formation of conventional renal cell carcinoma? Urology 2005; 65:411-414

Peters G J and Kohne C H, Resistance to antimetabolites. In: Fluoropyrimidines as Antifolate Drugs in Cancer Therapy. Jackman A L (ed). Humana Press Inc. 1999; pp 101-145.

Razin S, The mycoplasmas. Microbiol. Rev 1978; 42:414-70.

Razin S, Yogev D, Naot Y, Molecular biology and pathogenicity of mycoplasmas. Microbiol Mol Biol Rev 1998; 62:1094-156.

Sasaki H, Igaki H, Ishizuka T, Kogoma Y, Sugimura T, Terada M, Presence of *Streptococcus* DNA sequence in surgical specimens of gastric cancer. Jpn J Cancer Res 1995; 86:791-4.

Seno T, Ayusawa D, Shimizu K, Koyama H, Takeishi K, Hori T, Thymineless death and genetic events in mammalian cells. Basic Life Sci 1985; 31:241-63.

Seno T, Ayusawa D, Shimizu K, Koyama H, Takeishi K, Hori T, Thymineless death and genetic events in mammalian cells. Basic Life Sci 1985; 31:241-63.

Sinigaglia F and Talmadge K W, Inhibition of [3H]thymidine incorporation by *Mycoplasma arginini*-infected cells due to enzymatic cleavage of the nucleoside. Eur J Immunol 1985; 15:692-6.

Sotos G A, Grogan L, Allegra C J, Preclinical and clinical aspects of biomodulation of 5-fluorouracil. Cancer Treat Rev 1994; 20:11-49.

Tanaka F, Fukuse T, Wada H, Fukushima M, The history, mechanism and clinical use of oral 5-fluorouracil derivative chemotherapeutic agents. Curr Pharm Biotechnol 2000; 1:137-64.

Tham T N, Ferris S, Kovacic R, Montagnier L, Blanchard A, Identification of *Mycoplasma pirum* genes involved in the salvage pathways for nucleosides. J Bacteriol 1993; 175: 5281-5.

Walko C M and Lindley C, Capecitabine: a review. Clin Ther 2005; 27:23-44.

Yang H, Qu L, Ma H, Chen L, Liu W, Liu C, Meng L, Wu J, Shou C, *Mycoplasma hyorhinis* infection in gastric carcinoma and its effects on the malignant phenotypes of gastric cancer cells. BMC Gastroenterol 2010; 10:132

The invention claimed is:

1. A compound which is 5-fluoro-2'-deoxyuridine-5'-O-[1-naphthyl(benzoxy-L-alaninyl)]phosphate (CPF373), or a pharmaceutically acceptable salt or metabolite thereof.

2. A compound which is 5-fluoro-2'-deoxyuridine-5'-O-[1-naphthyl(benzoxy-L-alaninyl)]phosphate (CPF373), or a pharmaceutically acceptable salt thereof.

3. A compound which is 5-fluoro-2'-deoxyuridine-5'-O-[1-naphthyl(benzoxy-L-alaninyl)]phosphate (CPF373), or a metabolite thereof.

4. A compound which is 5-fluoro-2'-deoxyuridine-5'-O-[1-naphthyl(benzoxy-L-alaninyl)]phosphate (CPF373).

5. A pharmaceutical composition comprising the compound according to claim 1, or a pharmaceutically acceptable salt or metabolite thereof, in combination with a pharmaceutically acceptable carrier, diluent or excipient.

6. A pharmaceutical composition comprising the compound according to claim 2, or a pharmaceutically acceptable salt thereof, in combination with a pharmaceutically acceptable carrier, diluent or excipient.

7. A pharmaceutical composition comprising the compound according to claim 3, or a metabolite thereof, in combination with a pharmaceutically acceptable carrier, diluent or excipient.

8. A pharmaceutical composition comprising the compound according to claim 4 in combination with a pharmaceutically acceptable carrier, diluent or excipient.

9. A method of treating a cancer selected from leukemia, pancreatic cancer, prostate cancer, lung cancer, breast cancer, and cervical cancer, comprising administering to a *Homo sapiens* patient in need of such treatment an effective dose of the compound according to claim 1, or a pharmaceutically acceptable salt or metabolite thereof.

10. The method of claim 9 wherein said cancer is breast cancer.

11. The method of claim 9 wherein said cancer is lung cancer.

12. A method of treating a cancer selected from oesophageal cancer, gastrointestinal cancer, head and neck cancer, and ovarian cancer, comprising administering to a *Homo sapiens* patient in need of such treatment an effective dose of the compound according to claim 1, or a pharmaceutically acceptable salt or metabolite thereof.

13. The method of claim 12 wherein said gastrointestinal cancer is selected from gastric cancer, small intestine cancer, and colon and rectum cancer.

14. The method of claim 12 wherein said cancer is colon and rectum cancer.

15. A method of treating a cancer selected from leukemia, pancreatic cancer, prostate cancer, lung cancer, breast cancer, and cervical cancer, comprising administering to a *Homo sapiens* patient in need of such treatment an effective dose of the compound according to claim 2, or a pharmaceutically acceptable salt thereof.

16. The method of claim 15 wherein said cancer is breast cancer.

17. The method of claim 15 wherein said cancer is lung cancer.

18. A method of treating a cancer selected from oesophageal cancer, gastrointestinal cancer, head and neck cancer, and ovarian cancer, comprising administering to a *Homo sapiens* patient in need of such treatment an effective dose of the compound according to claim 2, or a pharmaceutically acceptable salt thereof.

19. The method of claim 18 wherein said gastrointestinal cancer is selected from gastric cancer, small intestine cancer, and colon and rectum cancer.

20. The method of claim 18 wherein said cancer is colon and rectum cancer.

21. A method of treating a cancer selected from leukemia, pancreatic cancer, prostate cancer, lung cancer, breast cancer, and cervical cancer, comprising administering to a *Homo sapiens* patient in need of such treatment an effective dose of the compound according to claim 3, or a metabolite thereof.

22. The method of claim 21 wherein said cancer is breast cancer.

23. The method of claim 21 wherein said cancer is lung cancer.

24. A method of treating a cancer selected from oesophageal cancer, gastrointestinal cancer, head and neck cancer, and ovarian cancer, comprising administering to a *Homo sapiens* patient in need of such treatment an effective dose of the compound according to claim 3, or a metabolite thereof.

25. The method of claim 24 wherein said gastrointestinal cancer is selected from gastric cancer, small intestine cancer, and colon and rectum cancer.

26. The method of claim 24 wherein said cancer is colon and rectum cancer.

27. A method of treating a cancer selected from leukemia, pancreatic cancer, prostate cancer, lung cancer, breast cancer, and cervical cancer, comprising administering to a *Homo sapiens* patient in need of such treatment an effective dose of the compound according to claim 4.

28. The method of claim 27 wherein said cancer is breast cancer.

29. The method of claim 27 wherein said cancer is lung cancer.

30. A method of treating a cancer selected from oesophageal cancer, gastrointestinal cancer, head and neck cancer, and ovarian cancer, comprising administering to a *Homo sapiens* patient in need of such treatment an effective dose of the compound according to claim 4.

31. The method of claim 30 wherein said gastrointestinal cancer is selected from gastric cancer, small intestine cancer, and colon and rectum cancer.

32. The method of claim 30 wherein said cancer is colon and rectum cancer.

* * * * *

UNITED STATES PATENT AND TRADEMARK OFFICE
CERTIFICATE OF CORRECTION

PATENT NO.         : 8,933,053 B2                                    Page 1 of 1
APPLICATION NO.    : 14/000682
DATED              : January 13, 2015
INVENTOR(S)        : Christopher McGuigan et al.

It is certified that error appears in the above-identified patent and that said Letters Patent is hereby corrected as shown below:

Title page Under (56) References Cited (Other Publications)

Page 2, Col. 1, line 35, delete "Tone" and insert -- Torre --;

Page 2, Col. 2, line 39, delete "phosphora' midate" and insert -- phosphoramidate --;

Page 2, Col. 2, line 65, delete "chern." and insert -- chem. --;

Page 3, Col. 1, line 21, delete "Immunoll" and insert -- Immunol --;

Page 3, Col. 2, line 20, delete "et aI," and insert -- et al, --;

Page 3, Col. 2, line 22, delete "et aI," and insert -- et al, --;

Page 3, Col. 2, line 23, delete "et aI," and insert -- et al, --;

Page 3, Col. 2, line 24, delete "et aI," and insert -- et al, --;

Page 3, Col. 2, line 26, delete "et aI," and insert -- et al, --;

Page 3, Col. 2, line 34, delete "et aI," and insert -- et al, --;

Page 3, Col. 2, line 35, delete "et aI," and insert -- et al, --;

Page 3, Col. 2, line 36, delete "et aI," and insert -- et al, --;

Page 3, Col. 2, line 37, delete "et aI," and insert -- et al, --;

Page 3, Col. 2, line 47, delete "et aI," and insert -- et al, --;

Page 3, Col. 2, line 51, delete "et aI," and insert -- et al, --.

Signed and Sealed this
Tenth Day of November, 2015

Michelle K. Lee
*Director of the United States Patent and Trademark Office*